United States Patent
Carson et al.

(10) Patent No.: US 6,923,817 B2
(45) Date of Patent: *Aug. 2, 2005

(54) TOTAL KNEE ARTHROPLASTY SYSTEMS AND PROCESSES

(75) Inventors: Christopher Patrick Carson, Collierville, TN (US); Christopher M. Lyons, Hernando, MS (US)

(73) Assignee: Smith & Nephew, Inc., Memphis, TN (US)

(*) Notice: Subject to any disclaimer, the term of this patent is extended or adjusted under 35 U.S.C. 154(b) by 362 days.

This patent is subject to a terminal disclaimer.

(21) Appl. No.: 10/084,012

(22) Filed: Feb. 27, 2002

(65) Prior Publication Data

US 2002/0147455 A1 Oct. 10, 2002

Related U.S. Application Data

(60) Provisional application No. 60/355,899, filed on Feb. 11, 2002, and provisional application No. 60/271,818, filed on Feb. 27, 2001.

(51) Int. Cl.$^7$ ............................................. A61B 19/00
(52) U.S. Cl. ..................................... 606/130; 128/898
(58) Field of Search .................. 600/424, 426; 606/64, 86, 96, 102, 130

(56) References Cited

U.S. PATENT DOCUMENTS

| | | |
|---|---|---|
| 4,952,213 A | 8/1990 | Bowman et al. |
| 5,190,547 A | 3/1993 | Barber, Jr. et al. |
| 5,383,454 A | 1/1995 | Bucholz |
| 5,389,101 A | 2/1995 | Helibrun et al. |
| 5,395,376 A | 3/1995 | Caspari et al. |
| 5,603,318 A | 2/1997 | Heilbrun et al. |

(Continued)

FOREIGN PATENT DOCUMENTS

| | | |
|---|---|---|
| DE | 42 25 112 C | 12/1993 |
| DE | 100 31 887 A1 | 1/2002 |
| EP | 0 676 178 A | 10/1995 |
| WO | WO 97/23172 | 7/1997 |
| WO | WO 99/60939 | 12/1999 |
| WO | WO 00/47103 | 8/2000 |
| WO | WO 01/91647 A1 | 12/2001 |

OTHER PUBLICATIONS

BrainLAB Brochure entitled "Ortho . . . Your Partner for the Future" pp. 1–28 (2002).

Delp, et al., "Computer–Assisted Knee Replacement," *Clinical Orthopaedics and Related Research*, 354:49–56 (1998).

Ellis, et al., "A Surgical Planning and Guidance System for High Tibial Osteotomy," *Journal of Computer–Assisted Surgery*, 4(5):264–274 (1999).

(Continued)

*Primary Examiner*—Julian W. Woo
*Assistant Examiner*—Sarah K. Webb
(74) *Attorney, Agent, or Firm*—Kilpatrick Stockton LLP

(57) ABSTRACT

Systems and processes for tracking anatomy, instrumentation, trial implants, implants, and references, and rendering images and data related to them in connection with surgical operations, for example total knee arthroplasties ("TKA"). These systems and processes are accomplished by using a computer to intraoperatively obtain images of body parts and to register, navigate, and track surgical instruments.

20 Claims, 64 Drawing Sheets

U.S. PATENT DOCUMENTS

| | | | |
|---|---|---|---|
| 5,643,268 A | | 7/1997 | Vilsmeier et al. |
| 5,676,668 A | | 10/1997 | McCue et al. |
| 5,682,886 A | * | 11/1997 | Delp et al. .................. 600/407 |
| 5,702,406 A | | 12/1997 | Vilsmeier et al. |
| 5,733,292 A | * | 3/1998 | Gustilo et al. ................ 606/88 |
| 5,748,767 A | | 5/1998 | Raab |
| 5,769,861 A | | 6/1998 | Vilsmeier |
| 5,772,594 A | | 6/1998 | Barrick |
| 5,792,147 A | | 8/1998 | Evans et al. |
| 5,799,055 A | | 8/1998 | Peshkin et al. |
| 5,807,252 A | | 9/1998 | Hassfeld et al. |
| 5,836,954 A | | 11/1998 | Heilbrun et al. |
| 5,871,018 A | | 2/1999 | Delp et al. |
| 5,871,445 A | | 2/1999 | Bucholz |
| 5,880,976 A | | 3/1999 | DiGioia, III et al. |
| 6,002,859 A | | 12/1999 | DiGioia, III et al. |
| 6,016,606 A | | 1/2000 | Oliver et al. |
| 6,069,932 A | | 5/2000 | Peshkin et al. |
| 6,083,163 A | | 7/2000 | Wegner et al. |
| 6,146,390 A | | 11/2000 | Heilbrun et al. |
| 6,165,181 A | | 12/2000 | Heilbrun et al. |
| 6,167,296 A | | 12/2000 | Shahidi |
| 6,190,320 B1 | | 2/2001 | Lelong |
| 6,198,794 B1 | | 3/2001 | Peshkin et al. |
| 6,200,316 B1 | | 3/2001 | Zwirkoski et al. |
| 6,205,411 B1 | | 3/2001 | DiGioia, III et al. |
| 6,226,548 B1 | * | 5/2001 | Foley et al. ................ 600/426 |
| 6,235,038 B1 | | 5/2001 | Hunter et al. |
| 6,236,875 B1 | | 5/2001 | Bucholz et al. |
| 6,249,581 B1 | | 6/2001 | Kok |
| 6,285,902 B1 | | 9/2001 | Kienzle, III et al. |
| 6,332,891 B1 | | 12/2001 | Himes |
| 6,344,853 B1 | | 2/2002 | Knight |
| 6,347,240 B1 | | 2/2002 | Foley et al. |
| 6,351,659 B1 | | 2/2002 | Vilsmeier |
| 6,385,475 B1 | | 5/2002 | Cinquin et al. |
| 6,558,421 B1 | | 5/2003 | Fell et al. |

OTHER PUBLICATIONS

Munoz, et al., Computer Assisted Planning of Hig Tibial Osteotomy for the Treatment of Knee Osteoarthritis, http://www.utc.fr/esb/esb09/abs_htm/570.html (Feb. 21, 2002) (three pages).

Stryker Navigation System brochure entitled ". . . best alignment for gap kinematics," two pages, undated.

Kanada, et al., "Image–Based Computer Assisted Orthopedic Surgery System," Bonecraft, Inc. (12 pages) (Apr. 30, 2001).

International Search Report in related Application No. PCT/US02/05783.

International Search Report in related Application No. PCT/US02/05955.

International Search Report in related Application No. PCT/US02/05956.

Croitoru et al., Fixation–Based Surgery: A New Technique for Distal Radius Osteotomy, Clinical Paper, Computer Aided Surgery 2001, 160–169, vol. 6.

Iyun et al., Planning and Performing the Ilizarov Method with the Taylor Spatial Frame, Abstract, at $2^{nd}$ Annual Meeting of International Society for Computer Assisted Orthopaedic Surgery, Jun. 21, 2002.

Krause, Computer–Aided Bone Deformity Correction, http://www.nd.edu/~gcopping/files/bonecraft6.pdf, May 21, 2001.

Barnes et al., "Unicompartmental Knee Arthroplasty," Bombay Hospital Journal, Issue Special, www.bhj.org/journal/1996/3803_july/special_486.htm.

Deluzio et al., "Static alignment and the adduction moment in unicompartmental arthroplasty patients," Presented at NACOB 98: North American Congress on Biomechanics, University of Waterloo, Ontario, Canada, Aug. 14–18, 1998.

DiGioia et al., Computer Assisted Orthopedic Surgery, Clinical Orthopaedics, Sep. 1998, vol. 354, pp. 8–16.

Foley et al., "Percutaneous pedicle screw fixation of the lumbar spine," Neurosurg. Focus, vol. 10(4), pp. 1–8 (2001).

Keifer et al., Computer Aided Knee Arthroplasty Versus Conventional Technique—First Results, First Annual Meeting of the International Society for Computer Assisted Orthopedic Surgery (Davos, Switzerland, Feb. 8–10, 2001).

Kunz et al., Development and Verification of a Non–CT Based Total Knee Arthroplasty System for the LCS Prosthesis, First Annual Meeting of the International Society for Computer Assisted Orthopedic Surgery (Davos, Switzerland, Feb. 8–10, 2001).

Picard et al., Kneenav.TKR: Concept and Clinical Application (Computer Assisted Orthopedic Surgery USA 2000 Meeting, Pittsburgh, PA., Jun. 15–17, 2000).

Saragaglia et al., Comuter Assisted Total Knee Arthroplasty: Comparison with a Conventional Procedure, First Annual Meeting of the International Society for Computer Assisted Orthopedic Surgery (Davos, Switzlerland, Feb. 8–10, 2001).

Simon et al., The Fundamentals of Virtual Fluoroscopy, Medtronic Surgical Navigation Technologies, Medtronic, pp. 57–66 (Computer Assisted Orthopedic Surgery USA 2000 Meeting, Pittsburgh, PA, Jun. 15–17, 2000).

Tenbusch et al., First Results Using the Robodoc System for Total Knee Replacement, First Annual Meeting of the International Society for Computer Assisted Orthopedic Surgrey (Davos, Switzerland, Feb. 8–10, 2001).

* cited by examiner

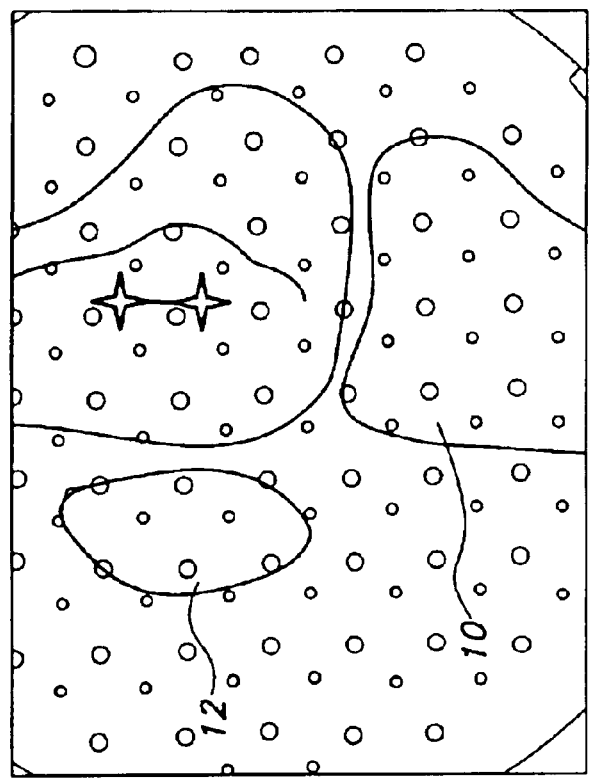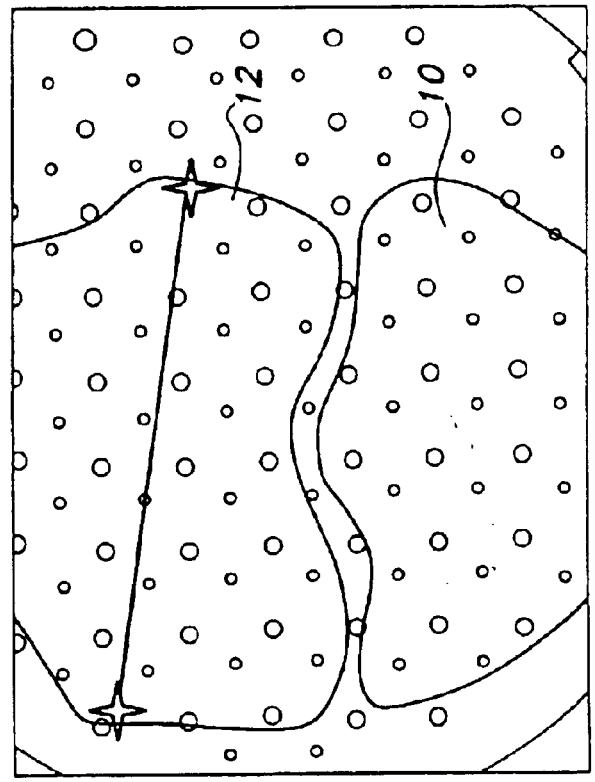
FIG. 20

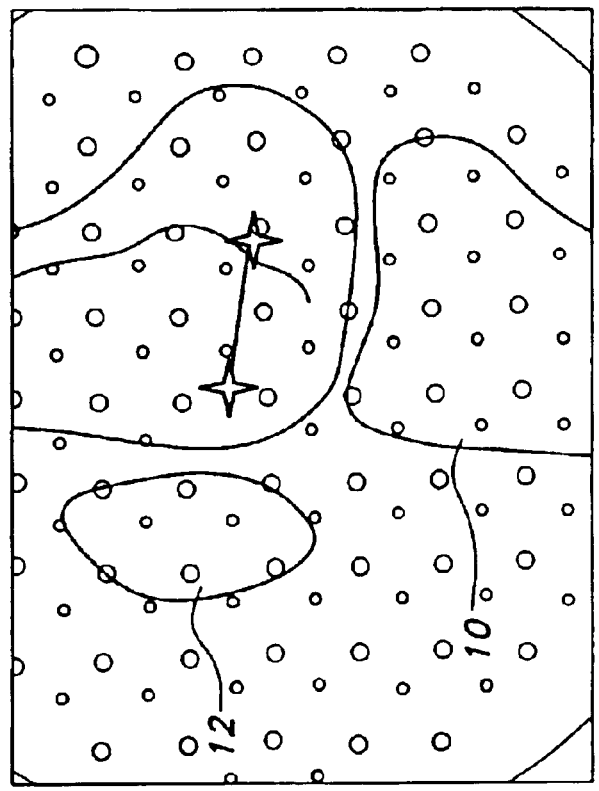
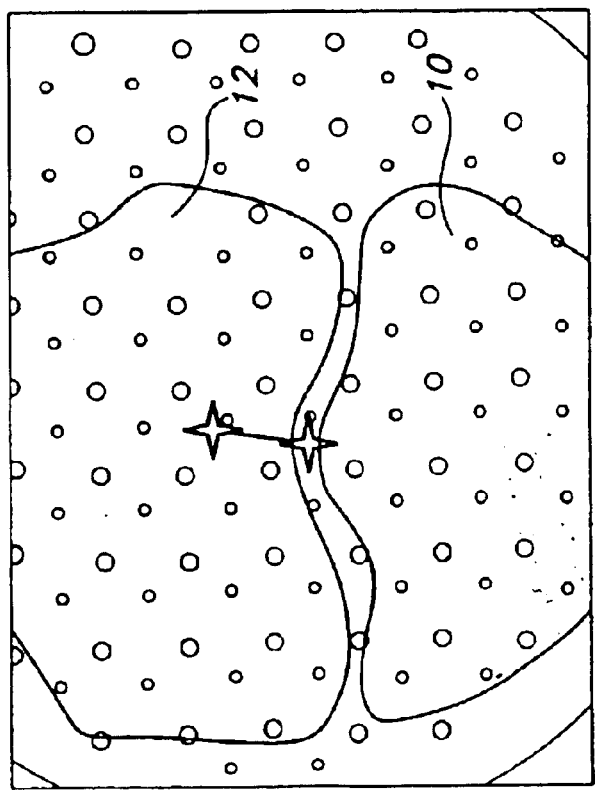
FIG. 21

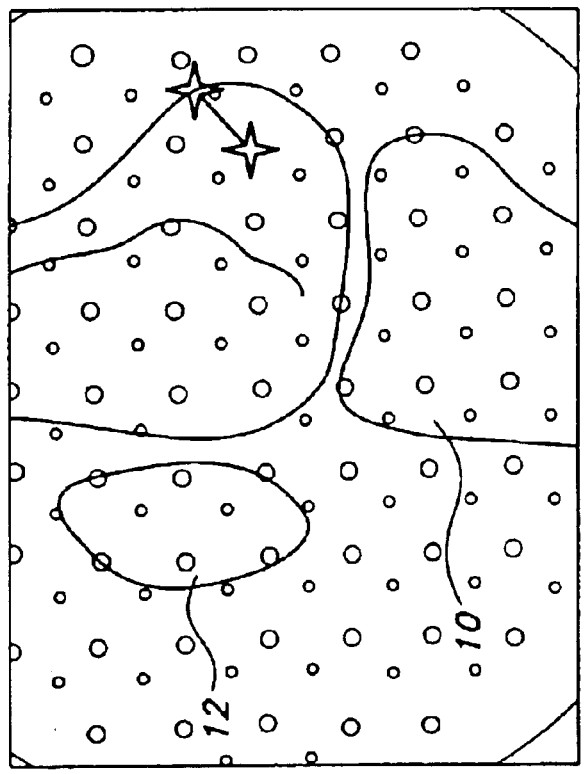
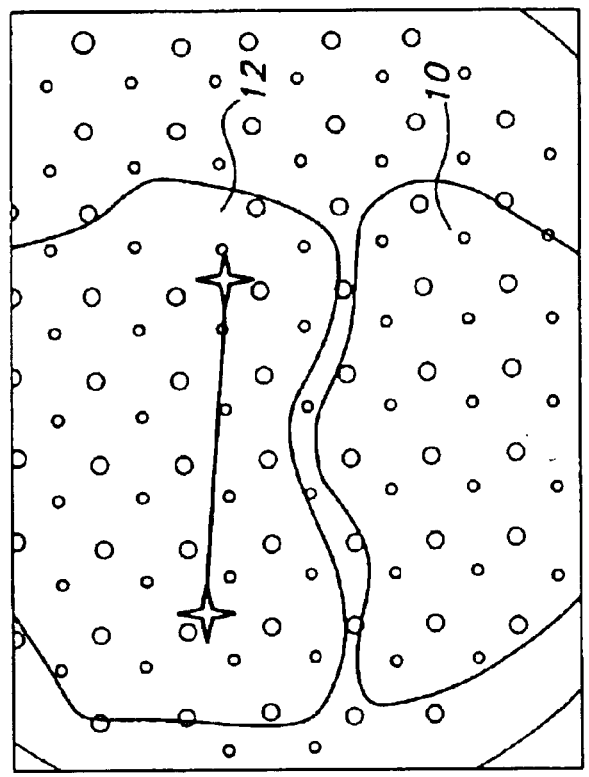
FIG 22

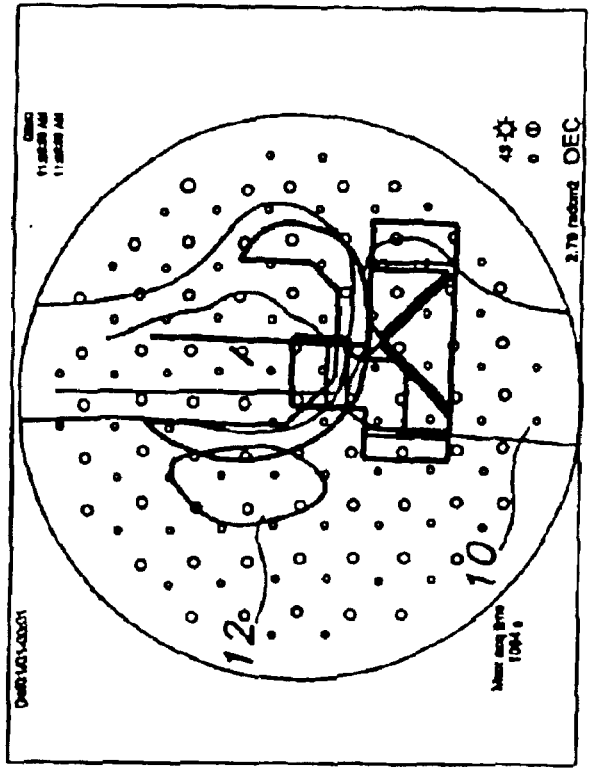
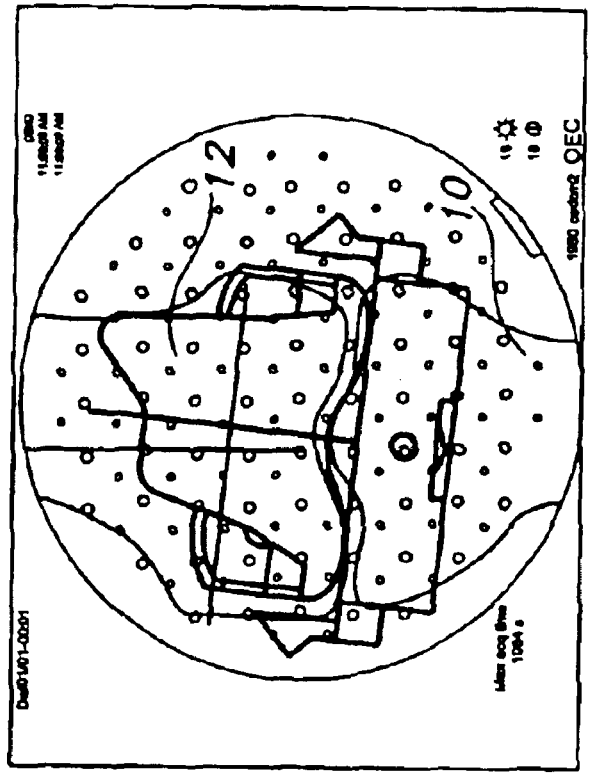
FIG 34

TOTAL KNEE ARTHROPLASTY SYSTEMS AND PROCESSES

RELATED APPLICATION DATA

This application claims the benefit of U.S. Ser. No. 60/271,818, filed Feb. 27, 2001 entitled "Image Guided System for Arthroplasty" and U.S. Ser. No. 60/355,899, filed Feb. 11, 2002 entitled "Surgical Navigation Systems and Processes," which documents are incorporated herein by this reference.

FIELD OF INVENTION

Systems and processes for tracking anatomy, implements, instrumentation, trial implants, implant components and virtual constructs or references, and rendering images and data related to them in connection with orthopedic, surgical and other operations, for example Total Knee Arthroplasty ("TKA"). Anatomical structures and such items may be attached to or otherwise associated with fiducial functionality, and constructs may be registered in position using fiducial functionality whose position and orientation can be sensed and tracked by systems and according to processes of the present invention in three dimensions in order to perform TKA. Such structures, items and constructs can be rendered onscreen properly positioned and oriented relative to each other using associated image files, data files, image input, other sensory input, based on the tracking. Such systems and processes, among other things, allow surgeons to navigate and perform TKA using images that reveal interior portions of the body combined with computer generated or transmitted images that show surgical implements, instruments, trials, implants, and/or other devices located and oriented properly relative to the body part. Such systems and processes allow, among other things, more accurate and effective resection of bone, placement and assessment of trial implants and joint performance, and placement and assessment of performance of actual implants and joint performance.

BACKGROUND AND SUMMARY

A leading cause of wear and revision in prosthetics such as knee implants, hip implants and shoulder implants is less than optimum implant alignment. In a Total Knee Arthroplasty, for example, current instrument design for resection of bone limits the alignment of the femoral and tibial resections to average values for varus/valgus flexion/extension, and external/internal rotation. Additionally, surgeons often use visual landmarks or "rules of thumb" for alignment which can be misleading due to anatomical variability. Intramedullary referencing instruments also violate the femoral and tibial canal. This intrusion increases the risk of fat embolism and unnecessary blood loss in the patient. Surgeons also rely on instrumentation to predict the appropriate implant size for the femur and tibia instead of the ability to intraoperatively template the appropriate size of the implants for optimal performance. Another challenge for surgeons is soft tissue or ligament balancing after the bone resections have been made. Releasing some of the soft tissue points can change the balance of the knee; however, the multiple options can be confusing for many surgeons. In revision TKA, for example, many of the visual landmarks are no longer present, making alignment and restoration of the joint line difficult. The present invention is applicable not only for knee repair, reconstruction or replacement surgery, but also repair, reconstruction or replacement surgery in connection with any other joint of the body as well as any other surgical or other operation where it is useful to track position and orientation of body parts, non-body components and/or virtual references such as rotational axes, and to display and output data regarding positioning and orientation of them relative to each other for use in navigation and performance of the operation.

Several providers have developed and marketed various forms of imaging systems for use in surgery. Many are based on CT scans and/or MRI data or on digitized points on the anatomy. Other systems align preoperative CT scans, MRIs or other images with intraoperative patient positions. A preoperative planning system allows the surgeon to select reference points and to determine the final implant position. Intraoperatively, the system calibrates the patient position to that preoperative plan, such as using a "point cloud" technique, and can use a robot to make femoral and tibial preparations.

Systems and processes according to one embodiment of the present invention use position and/or orientation tracking sensors such as infrared sensors acting stereoscopically or otherwise to track positions of body parts, surgery-related items such as implements, instrumentation, trial prosthetics, prosthetic components, and virtual constructs or references such as rotational axes which have been calculated and stored based on designation of bone landmarks. Processing capability such as any desired form of computer functionality, whether standalone, networked, or otherwise, takes into account the position and orientation information as to various items in the position sensing field (which may correspond generally or specifically to all or portions or more than all of the surgical field) based on sensed position and orientation of their associated fiducials or based on stored position and/or orientation information. The processing functionality correlates this position and orientation information for each object with stored information regarding the items, such as a computerized fluoroscopic imaged file of a femur or tibia, a wire frame data file for rendering a representation of an instrumentation component, trial prosthesis or actual prosthesis, or a computer generated file relating to a rotational axis or other virtual construct or reference. The processing functionality then displays position and orientation of these objects on a screen or monitor, or otherwise. Thus, systems and processes according to one embodiment of the invention can display and otherwise output useful data relating to predicted or actual position and orientation of body parts, surgically related items, implants, and virtual constructs for use in navigation, assessment, and otherwise performing surgery or other operations.

As one example, images such as fluoroscopy images showing internal aspects of the femur and tibia can be displayed on the monitor in combination with actual or predicted shape, position and orientation of surgical implements, instrumentation components, trial implants, actual prosthetic components, and rotational axes in order to allow the surgeon to properly position and assess performance of various aspects of the joint being repaired, reconstructed or replaced. The surgeon may navigate tools, instrumentation, trial prostheses, actual prostheses and other items relative to bones and other body parts in order to perform TKA's more accurately, efficiently, and with better alignment and stability. Systems and processes according to the present invention can also use the position tracking information and, if desired, data relating to shape and configuration of surgical related items and virtual constructs or references in order to produce numerical data which may be used with or without graphic imaging to perform tasks such as assessing performance of trial prosthetics statically and throughout a range of motion, appropriately modifying tissue such as ligaments to improve such performance and similarly assessing performance of actual prosthetic components which have been placed in the patient for alignment and stability. Systems and processes according to the present invention can also generate data based on position tracking and, if desired, other information to provide cues on screen, aurally or as otherwise desired to assist in the surgery such as suggesting certain bone modification steps or measures which may be taken to release certain ligaments or portions of them based on performance of components as sensed by systems and processes according to the present invention.

According to a preferred embodiment of systems and processes according to the present invention, at least the following steps are involved:

1. Obtain appropriate images such as fluoroscopy images of appropriate body parts such as femur and tibia, the imager being tracked in position via an associated fiducial whose position and orientation is tracked by position/orientation sensors such as stereoscopic infrared (active or passive) sensors according to the present invention.
2. Register tools, instrumentation, trial components, prosthetic components, and other items to be used in surgery, each of which corresponds to a fiducial whose position and orientation can be tracked by the position/orientation sensors.
3. Locating and registering body structure such as designating points on the femur and tibia using a probe associated with a fiducial in order to provide the processing functionality information relating to the body part such as rotational axes.
4. Navigating and positioning instrumentation such as cutting instrumentation in order to modify bone, at least partially using images generated by the processing functionality corresponding to what is being tracked and/or has been tracked, and/or is predicted by the system, and thereby resecting bone effectively, efficiently and accurately.
5. Navigating and positioning trial components such as femoral components and tibial components, some or all of which may be installed using impactors with a fiducial and, if desired, at the appropriate time discontinuing tracking the position and orientation of the trial component using the impactor fiducial and starting to track that position and orientation using the body part fiducial on which the component is installed.
6. Assessing alignment and stability of the trial components and joint, both statically and dynamically as desired, using images of the body parts in combination with images of the trial components while conducting appropriate rotation, anterior-posterior drawer and flexion/extension tests and automatically storing and calculating results to present data or information which allows the surgeon to assess alignment and stability.
7. Releasing tissue such as ligaments if necessary and adjusting trial components as desired for acceptable alignment and stability.
8. Installing implant components whose positions may be tracked at first via fiducials associated with impactors for the components and then tracked via fiducials on the body parts in which the components are installed.
9. Assessing alignment and stability of the implant components and joint by use of some or all tests mentioned above and/or other tests as desired, releasing tissue if desired, adjusting if desired, and otherwise verifying acceptable alignment, stability and performance of the prosthesis, both statically and dynamically.

This process, or processes including it or some of it may be used in any total or partial joint repair, reconstruction or replacement, including knees, hips, shoulders, elbows, ankles and any other desired joint in the body.

Such processes are disclosed in U.S. Ser. No. 60/271,818 filed Feb. 27, 2001, entitled Image Guided System for Arthroplasty, which is incorporated herein by reference as are all documents incorporated by reference therein.

Systems and processes according to the present invention represent significant improvement over other previous systems and processes. For instance, systems which use CT and MRI data generally require the placement of reference frames pre-operatively which can lead to infection at the pin site. The resulting 3D images must then be registered, or calibrated, to the patient anatomy intraoperatively. Current registration methods are less accurate than the fluoroscopic system. These imaging modalities are also more expensive. Some "imageless" systems, or non-imaging systems, require digitizing a large number of points to define the complex anatomical geometries of the knee at each desired site. This can be very time intensive resulting in longer operating room time. Other imageless systems determine the mechanical axis of the knee by performing an intraoperative kinematic motion to determine the center of rotation at the hip, knee, and ankle. This requires placement of reference frames at the iliac crest of the pelvis and in or on the ankle. This calculation is also time consuming at the system must find multiple points in different planes in order to find the center of rotation. This is also problematic in patients with a pathologic condition. Ligaments and soft tissues in the arthritic patient are not normal and thus will give a center of rotation that is not desirable for normal knees. Robotic systems require expensive CT or MRI scans and also require pre-operative placement of reference frames, usually the day before surgery. These systems are also much slower, almost doubling operating room time and expense.

None of these systems can effectively track femoral and/or tibial trials during a range of motion and calculate the relative positions of the articular surfaces, among other things. Also, none of them currently make suggestions on ligament balancing, display ligament balancing techniques, or surgical techniques. Additionally, none of these systems currently track the patella.

An object of certain aspects of the present invention is to use computer processing functionality in combination with imaging and position and/or orientation tracking sensors to present to the surgeon during surgical operations visual and data information useful to navigate, track and/or position implements, instrumentation, trial components, prosthetic components and other items and virtual constructs relative to the human body in order to improve performance of a repaired, replaced or reconstructed knee joint.

Another object of certain aspects of the present invention is to use computer processing functionality in combination with imaging and position and/or orientation tracking sensors to present to the surgeon during surgical operations visual and data information useful to assess performance of a knee and certain items positioned therein, including components such as trial components and prosthetic components, for stability, alignment and other factors, and to adjust tissue and body and non-body structure in order to improve such performance of a repaired, reconstructed or replaced knee joint.

Another object of certain aspects of the present invention is to use computer processing functionality in combination with imaging and position and/or orientation tracking sensors to present to the surgeon during surgical operations visual and data information useful to show predicted position and movement of implements, instrumentation, trial components, prosthetic components and other items and virtual constructs relative to the human body in order to select appropriate components, resect bone accurately, effectively and efficiently, and thereby improve performance of a repaired, replaced or reconstructed knee joint.

Other objects, features and advantages of the present invention are apparent with respect to the remainder of this document.

BRIEF DESCRIPTION OF THE DRAWINGS

FIG. 20 is a screen face produced according to one embodiment of the present invention during designation of landmarks to determine an epicondylar axis.

FIG. 21 is a screen face produced according to one embodiment of the present invention during designation of landmarks to determine an anterior-posterior axis.

FIG. 22 is a screen face produced according to one embodiment of the present invention during designation of landmarks to determine a posterior condylar axis.

FIG. 34 is a screen face which shows a fluoroscopic image of bone in combination with computer generated images of axes and components in accordance with one embodiment of the present invention.

FIG. 58 is a screen face according to one embodiment of the present invention which may be used to assist in assessing joint function.

DETAILED DESCRIPTION

Figure 1:
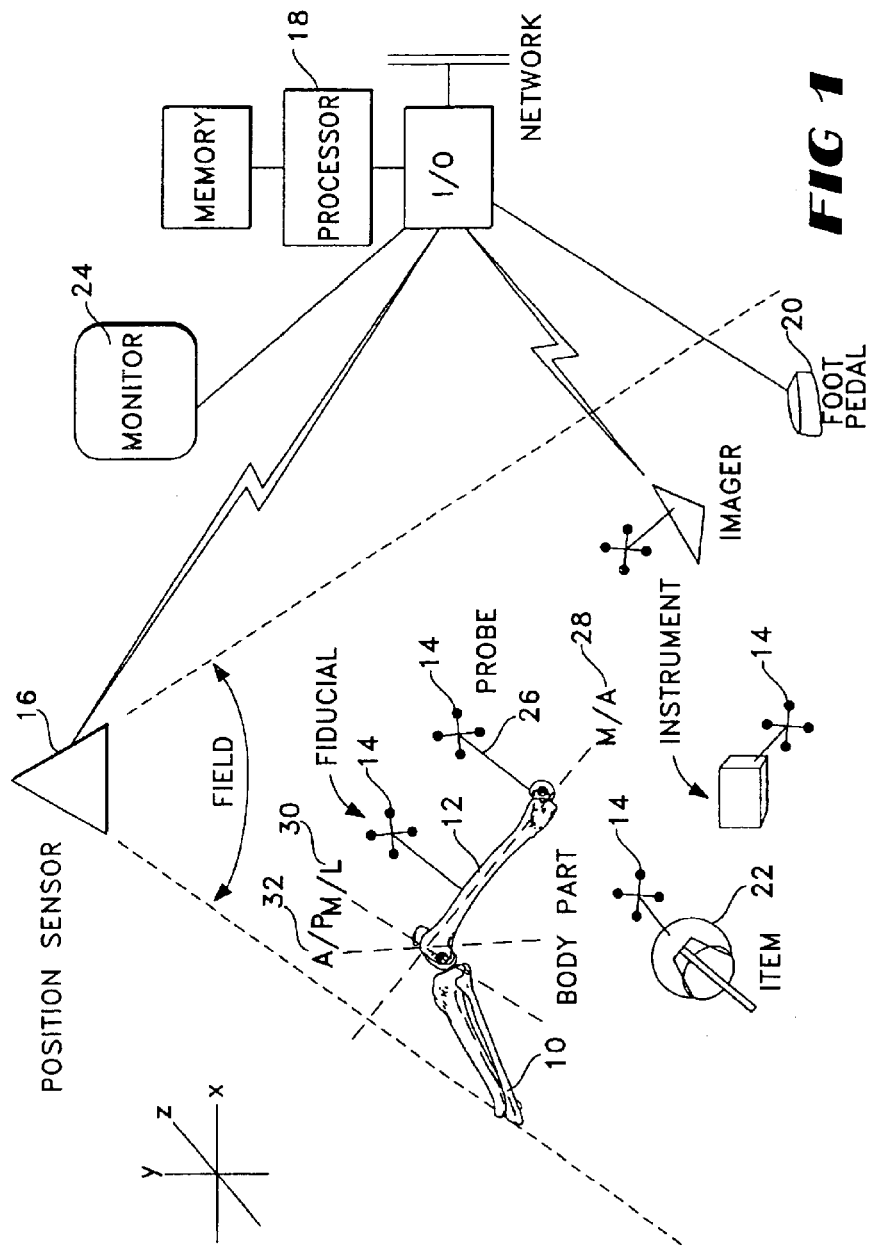
FIG. 1 is a schematic view of a particular embodiment of systems and processes according to the present invention.

Systems and processes according to a preferred embodiment of the present invention use computer capacity, including standalone and/or networked, to store data regarding spatial aspects of surgically related items and virtual constructs or references including body parts, implements, instrumentation, trial components, prosthetic components and rotational axes of body parts. Any or all of these may be physically or virtually connected to or incorporate any desired form of mark, structure, component, or other fiducial or reference device or technique which allows position and/or orientation of the item to which it is attached to be sensed and tracked, preferably in three dimensions of translation and three degrees of rotation as well as in time if desired. In the preferred embodiment, such "fidicuals" are reference frames each containing at least three, preferably four, sometimes more, reflective elements such as spheres reflective of lightwave or infrared energy, or active elements such as LEDs.

In a preferred embodiment, orientation of the elements on a particular fiducial varies from one fiducial to the next so that sensors according to the present invention may distinguish between various components to which the fiducials are attached in order to correlate for display and other purposes data files or images of the components. In a preferred embodiment of the present invention, some fiducials use reflective elements and some use active elements, both of which may be tracked by preferably two, sometimes more infrared sensors whose output may be processed in concert to geometrically calculate position and orientation of the item to which the fiducial is attached.

Position/orientation tracking sensors and fiducials need not be confined to the infrared spectrum. Any electromagnetic, electrostatic, light, sound, radiofrequency or other desired technique may be used. Alternatively, each item such as a surgical implement, instrumentation component, trial component, implant component or other device may contain its own "active" fiducial such as a microchip with appropriate field sensing or position/orientation sensing functionality and communications link such as spread spectrum RF link, in order to report position and orientation of the item. Such active fiducials, or hybrid active/passive fiducials such as transponders can be implanted in the body parts or in any of the surgically related devices mentioned above, or conveniently located at their surface or otherwise as desired. Fiducials may also take the form of conventional structures such as a screw driven into a bone, or any other three dimensional item attached to another item, position and orientation of such three dimensional item able to be tracked in order to track position and orientation of body parts and surgically related items. Hybrid fiducials may be partly passive, partly active such as inductive components or transponders which respond with a certain signal or data set when queried by sensors according to the present invention.

Systems and processes according to a preferred embodiment of the present invention employ a computer to calculate and store reference axes of body components such as in a TKA, for example, the mechanical axis of the femur and tibia. From these axes such systems track the position of the instrumentation and osteotomy guides so that bone resections will locate the implant position optimally, usually aligned with the mechanical axis. Furthermore, during trial reduction of the knee, the systems provide feedback on the balancing of the ligaments in a range of motion and under varus/valgus, anterior/posterior and rotary stresses and can suggest or at least provide more accurate information than in the past about which ligaments the surgeon should release in order to obtain correct balancing, alignment and stability. Systems and processes according to the present invention can also suggest modifications to implant size, positioning, and other techniques to achieve optimal kinematics. Systems and processes according to the present invention can also include databases of information regarding tasks such as ligament balancing, in order to provide suggestions to the surgeon based on performance of test results as automatically calculated by such systems and processes.

FIG. 1 is a schematic view showing one embodiment of a system according to the present invention and one version of a setting according to the present invention in which surgery on a knee, in this case a Total Knee Arthroplasty, may be performed. Systems and processes according to the present invention can track various body parts such as tibia 10 and femur 12 to which fiducials of the sort described above or any other sort may be implanted, attached, or otherwise associated physically, virtually, or otherwise. In the embodiment shown in FIG. 1, fiducials 14 are structural frames some of which contain reflective elements, some of which contain LED active elements, some of which can contain both, for tracking using stereoscopic infrared sensors suitable, at least operating in concert, for sensing, storing, processing and/or outputting data relating to ("tracking") position and orientation of fiducials 14 and thus components such as 10 and 12 to which they are attached or otherwise associated. Position sensor 16, as mentioned above, may be any sort of sensor functionality for sensing position and orientation of fiducials 14 and therefore items with which they are associated, according to whatever desired electrical, magnetic, electromagnetic, sound, physical, radio frequency, or other active or passive technique. In the preferred embodiment, position sensor 16 is a pair of infrared sensors disposed on the order of a meter, sometimes more, sometimes less, apart and whose output can be processed in concert to provide position and orientation information regarding fiducials 14.

In the embodiment shown in FIG. 1, computing functionality 18 can include processing functionality, memory functionality, input/output functionality whether on a standalone or distributed basis, via any desired standard, architecture, interface and/or network topology. In this embodiment, computing functionality 18 is connected to a monitor on which graphics and data may be presented to the surgeon during surgery. The screen preferably has a tactile interface so that the surgeon may point and click on screen for tactile screen input in addition to or instead of, if desired, keyboard and mouse conventional interfaces. Additionally, a foot pedal 20 or other convenient interface may be coupled to functionality 18 as can any other wireless or wireline interface to allow the surgeon, nurse or other desired user to control or direct functionality 18 in order to, among other things, capture position/orientation information when certain components are oriented or aligned properly. Items 22 such as trial components, instrumentation components may be tracked in position and orientation relative to body parts 10 and 12 using fiducials 14.

Computing functionality 18 can process, store and output on monitor 24 and otherwise various forms of data which correspond in whole or part to body parts 10 and 12 and other components for item 22. For example, in the embodiment shown in FIG. 1, body parts 10 and 12 are shown in cross-section or at least various internal aspects of them such as bone canals and surface structure are shown using fluoroscopic images. These images are obtained using a C-arm attached to a fiducial 14. The body parts, for example, tibia 10 and femur 12, also have fiducials attached. When the fluoroscopy images are obtained using the C-arm with fiducial 14, a position/orientation sensor 16 "sees" and tracks the position of the fluoroscopy head as well as the positions and orientations of the tibia 10 and femur 12. The computer stores the fluoroscopic images with this position/orientation information, thus correlating position and orientation of the fluoroscopic image relative to the relevant body part or parts. Thus, when the tibia 10 and corresponding fiducial 14 move, the computer automatically and correspondingly senses the new position of tibia 10 in space and can correspondingly move implements, instruments, references, trials and/or implants on the monitor 24 relative to the image of tibia 10. Similarly, the image of the body part can be moved, both the body part and such items may be moved, or the on screen image otherwise presented to suit the preferences of the surgeon or others and carry out the imaging that is desired. Similarly, when an item 22 such as an extramedullary rod, intramedullary rod, or other type of rod, that is being tracked moves, its image moves on monitor 24 so that the monitor shows the item 22 in proper position and orientation on monitor 24 relative to the femur 12. The rod 22 can thus appear on the monitor 24 in proper or improper alignment with respect to the mechanical axis and other features of the femur 12, as if the surgeon were able to see into the body in order to navigate and position rod 22 properly.

The computer functionality 18 can also store data relating to configuration, size and other properties of items 22 such as implements, instrumentation, trial components, implant components and other items used in surgery. When those are introduced into the field of position/orientation sensor 16, computer functionality 18 can generate and display overlain or in combination with the fluoroscopic images of the body parts 10 and 12, computer generated images of implements, instrumentation components, trial components, implant components and other items 22 for navigation, positioning, assessment and other uses.

Additionally, computer functionality 18 can track any point in the position/orientation sensor 16 field such as by using a designator or a probe 26. The probe also can contain or be attached to a fiducial 14. The surgeon, nurse, or other user touches the tip of probe 26 to a point such as a landmark on bone structure and actuates the foot pedal 20 or otherwise instructs the computer 18 to note the landmark position. The position/orientation sensor 16 "sees" the position and orientation of fiducial 14 "knows" where the tip of probe 26 is relative to that fiducial 14 and thus calculates and stores, and can display on monitor 24 whenever desired and in whatever form or fashion or color, the point or other position designated by probe 26 when the foot pedal 20 is hit or other command is given. Thus, probe 26 can be used to designate landmarks on bone structure in order to allow the computer 18 to store and track, relative to movement of the bone fiducial 14, virtual or logical information such as mechanical axis 28, medial lateral axis 30 and anterior/posterior axis 32 of femur 12, tibia 10 and other body parts in addition to any other virtual or actual construct or reference.

Figure 2:
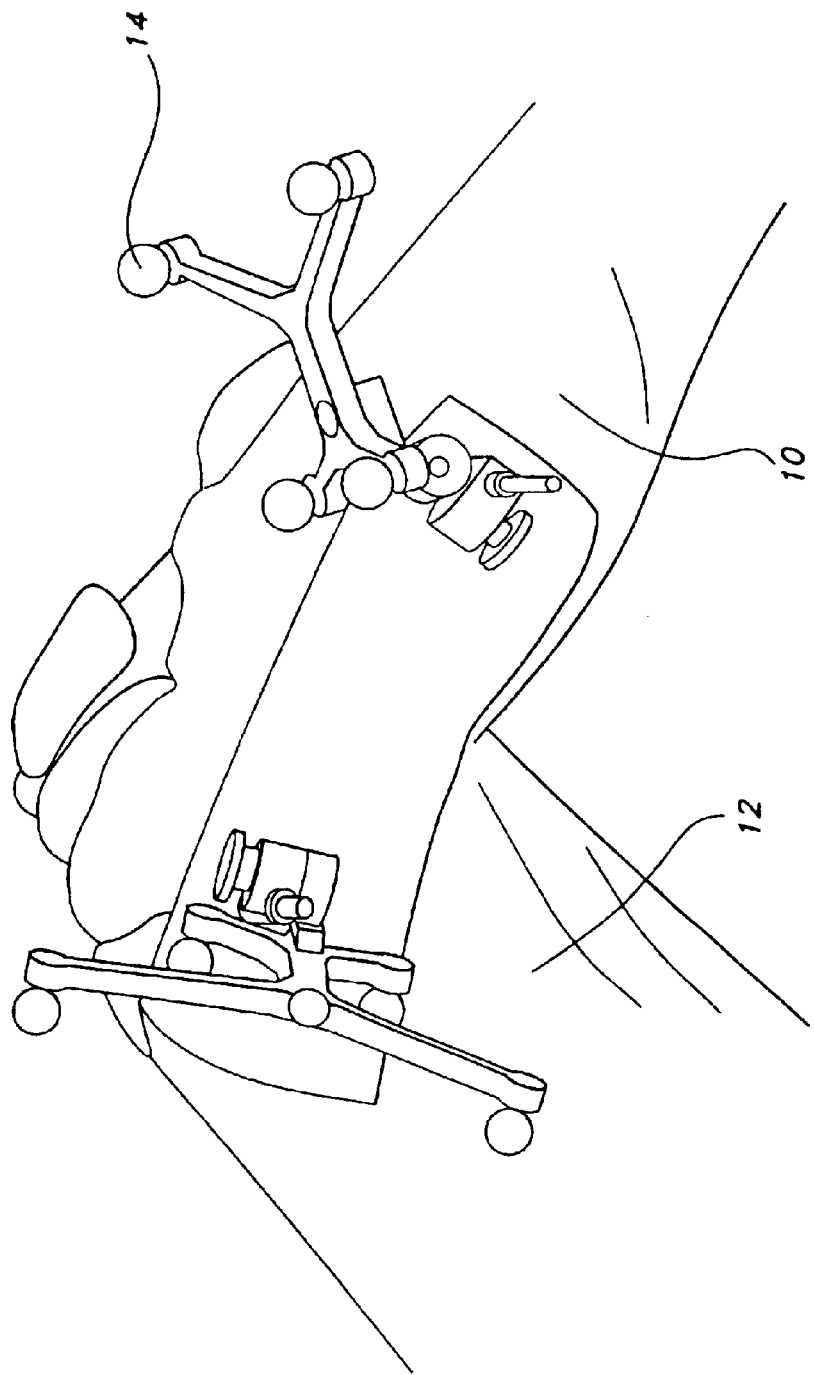
FIG. 2 is a view of a knee prepared for surgery, including a femur and a tibia, to which fiducials according to one embodiment of the present invention have been attached.
Figure 64:
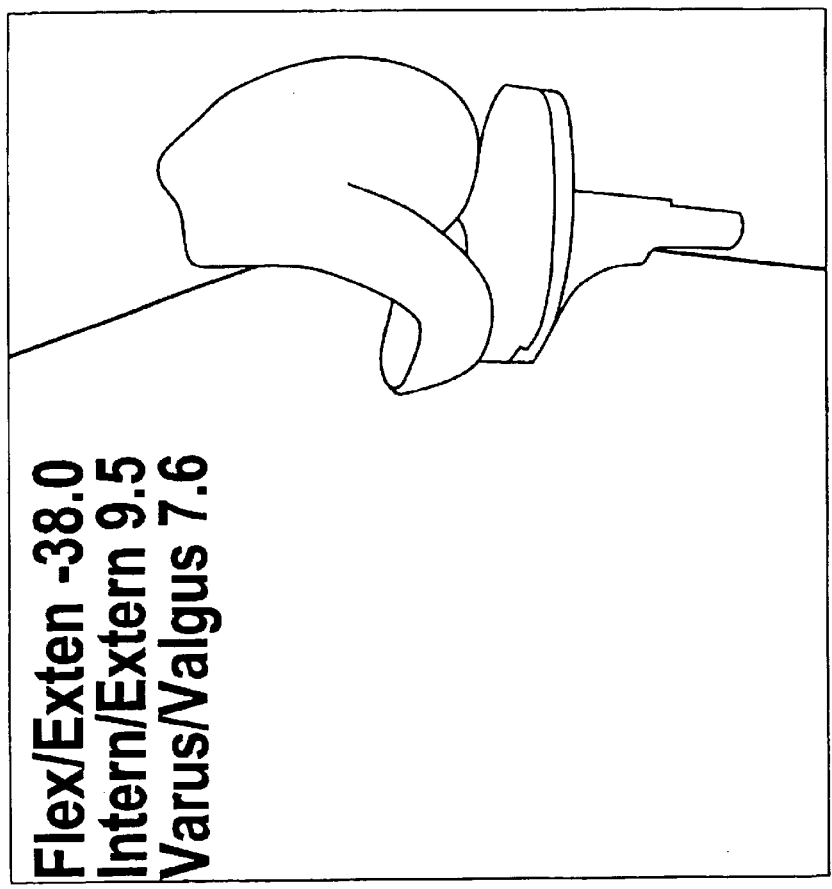
FIG. 64 is a computer generated graphic according to one embodiment of the present invention which allows visualization of trial or actual components installed in the bone structure according to one embodiment of the invention.

Systems and processes according to an embodiment of the present invention such as the subject of FIGS. 2–64, can use the so-called FluoroNAV system and software provided by Medtronic Sofamor Danek Technologies. Such systems or aspects of them are disclosed in U.S. Pat. Nos. 5,383,454; 5,871,445; 6,146,390; 6,165,81; 6,235,038 and 6,236,875, and related (under 35 U.S.C. Section 119 and/or 120) patents, which are all incorporated herein by this reference. Any other desired systems can be used as mentioned above for imaging, storage of data, tracking of body parts and items and for other purposes. The FluoroNav system requires the use of reference frame type fiducials 14 which have four and in some cases five elements tracked by infrared sensors for position/orientation of the fiducials and thus of the body part, implement, instrumentation, trial component, implant component, or other device or structure being tracked. Such systems also use at least one probe 26 which the surgeon can use to select, designate, register, or otherwise make known to the system a point or points on the anatomy or other locations by placing the probe as appropriate and signaling or commanding the computer to note the location of, for instance, the tip of the probe. The FluoroNav system also tracks position and orientation of a C-arm used to obtain fluoroscopic images of body parts to which fiducials have been attached for capturing and storage of fluoroscopic images keyed to position/orientation information as tracked by the sensors 16. Thus, the monitor 24 can render fluoroscopic images of bones in combination with computer generated images of virtual constructs and references together with implements, instrumentation components, trial components, implant components and other items used in connection with surgery for navigation, resection of bone, assessment and other purposes.

Figure 3:
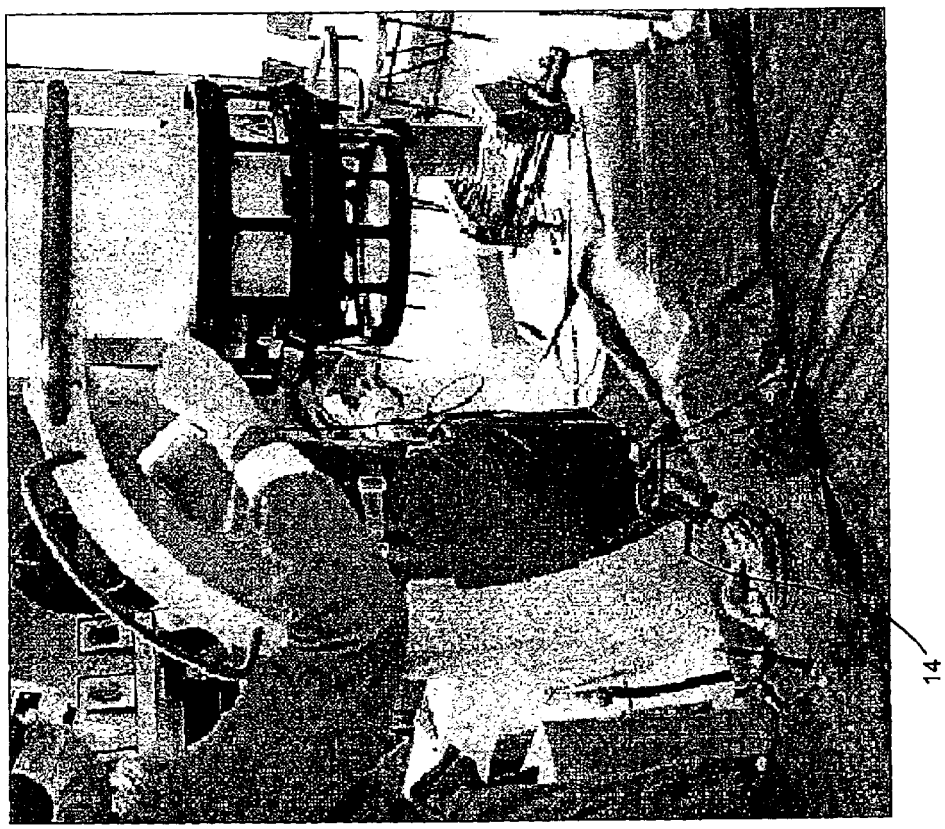
FIG. 3 is a view of a portion of a leg prepared for surgery according to the present invention with a C-arm for obtaining fluoroscopic images associated with a fiducial according to one embodiment of the present invention.

FIGS. 2–64 are various views associated with Total Knee Arthroplasty surgery processes according to one particular embodiment and version of the present invention being carried out with the FluoroNav system referred to above. FIG. 2 shows a human knee in the surgical field, as well as the corresponding femur and tibia, to which fiducials 14 have been rigidly attached in accordance with this embodiment of the invention. Attachment of fiducials 14 preferably is accomplished using structure that withstands vibration of surgical saws and other phenomenon which occur during surgery without allowing any substantial movement of fiducial 14 relative to body part being tracked by the system. FIG. 3 shows fluoroscopy images being obtained of the body parts with fiducials 14 attached. The fiducial 14 on the fluoroscopy head in this embodiment is a cylindrically shaped cage which contains LEDs or "active" emitters for tracking by the sensors 16. Fiducials 14 attached to tibia 10 and femur 12 can also be seen. The fiducial 14 attached to the femur 12 uses LEDs instead of reflective spheres and is thus active, fed power by the wire seen extending into the bottom of the image.

Figure 4:
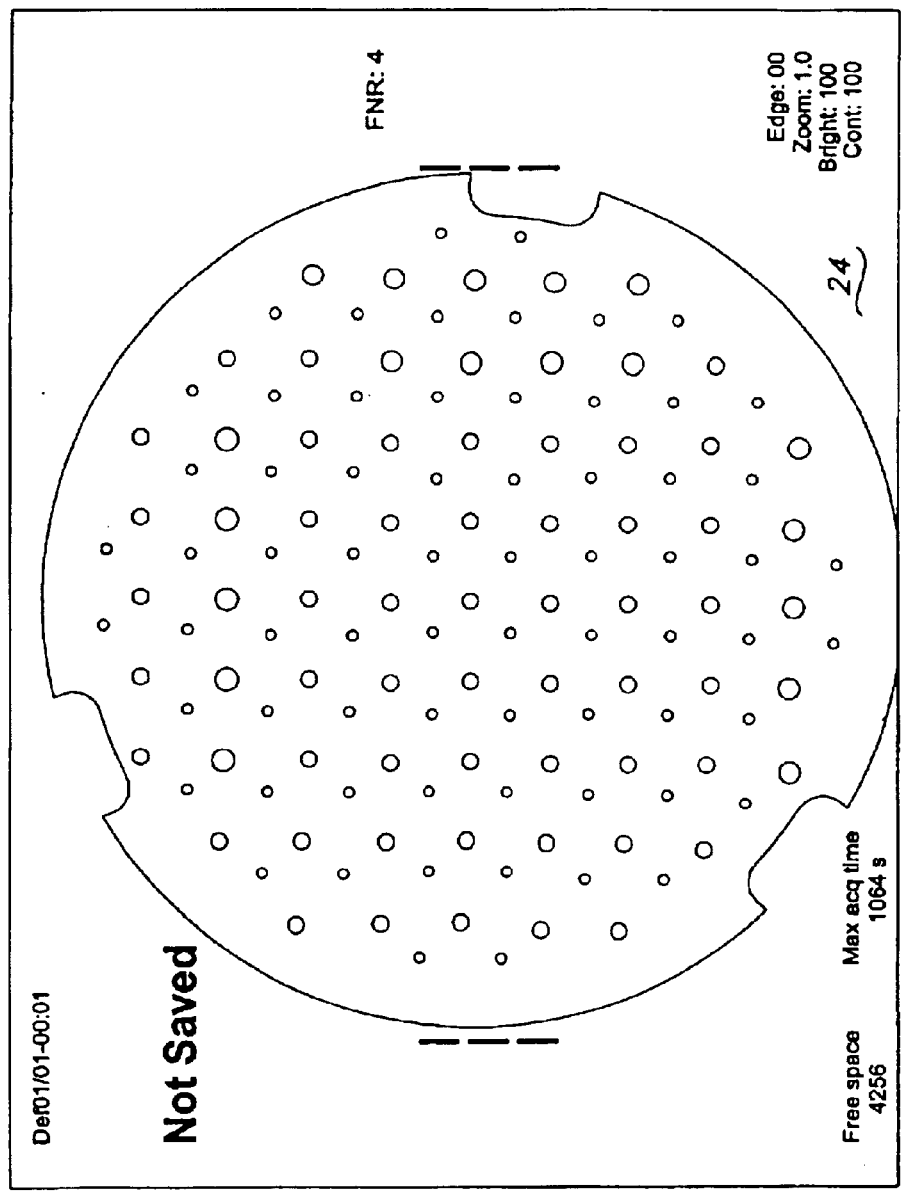
FIG. 4 is a fluoroscopic image of free space rendered on a monitor according to one embodiment of the present invention.
Figure 5:
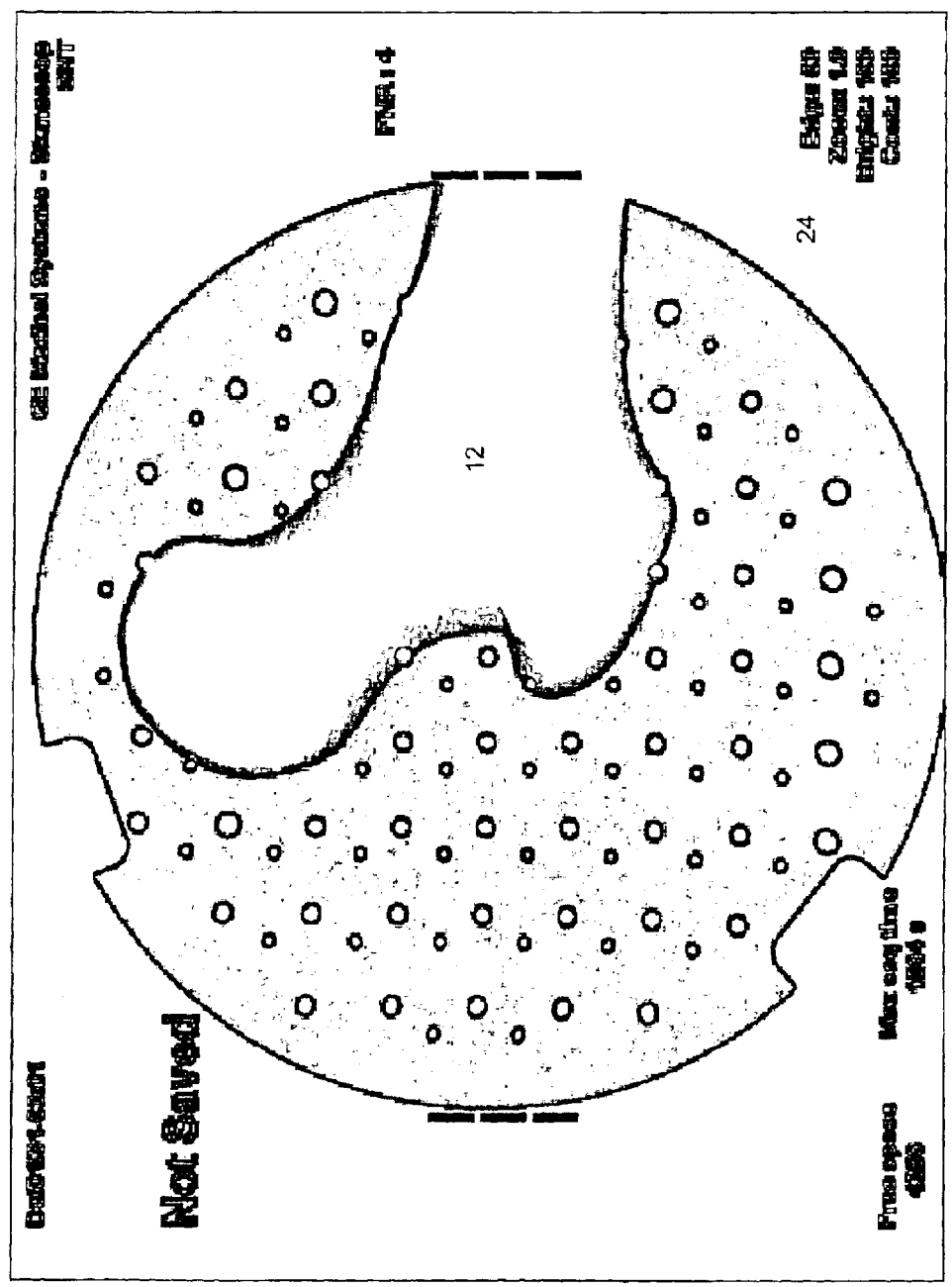
FIG. 5 is a fluoroscopic image of femoral head obtained and rendered according one embodiment of the present invention.

FIGS. 4–10 are fluoroscopic images shown on monitor 24 obtained with position and/or orientation information received by, noted and stored within computer 18. FIG. 4 is an open field with no body part image, but which shows the optical indicia which may be used to normalize the image obtained using a spherical fluoroscopy wave front with the substantially flat surface of the monitor 24. FIG. 5 shows an image of the femur 12 head. This image is taken in order to allow the surgeon to designate the center of rotation of the femoral head for purposes of establishing the mechanical axis and other relevant constructs relating to of the femur according to which the prosthetic components will ultimately be positioned. Such center of rotation can be established by articulating the femur within the acetabulum or a prosthesis to capture a number of samples of position and orientation information and thus in turn to allow the computer to calculate the average center of rotation. The center of rotation can be established by using the probe and designating a number of points on the femoral head and thus allowing the computer to calculate the geometrical center or a center which corresponds to the geometry of points collected. Additionally, graphical representations such as controllably sized circles displayed on the monitor can be fitted by the surgeon to the shape of the femoral head on planar images using tactile input on screen to designate the centers according to that graphic, such as are represented by the computer as intersection of axes of the circles. Other techniques for determining, calculating or establishing points or constructs in space, whether or not corresponding to bone structure, can be used in accordance with the present invention.

Figure 6:
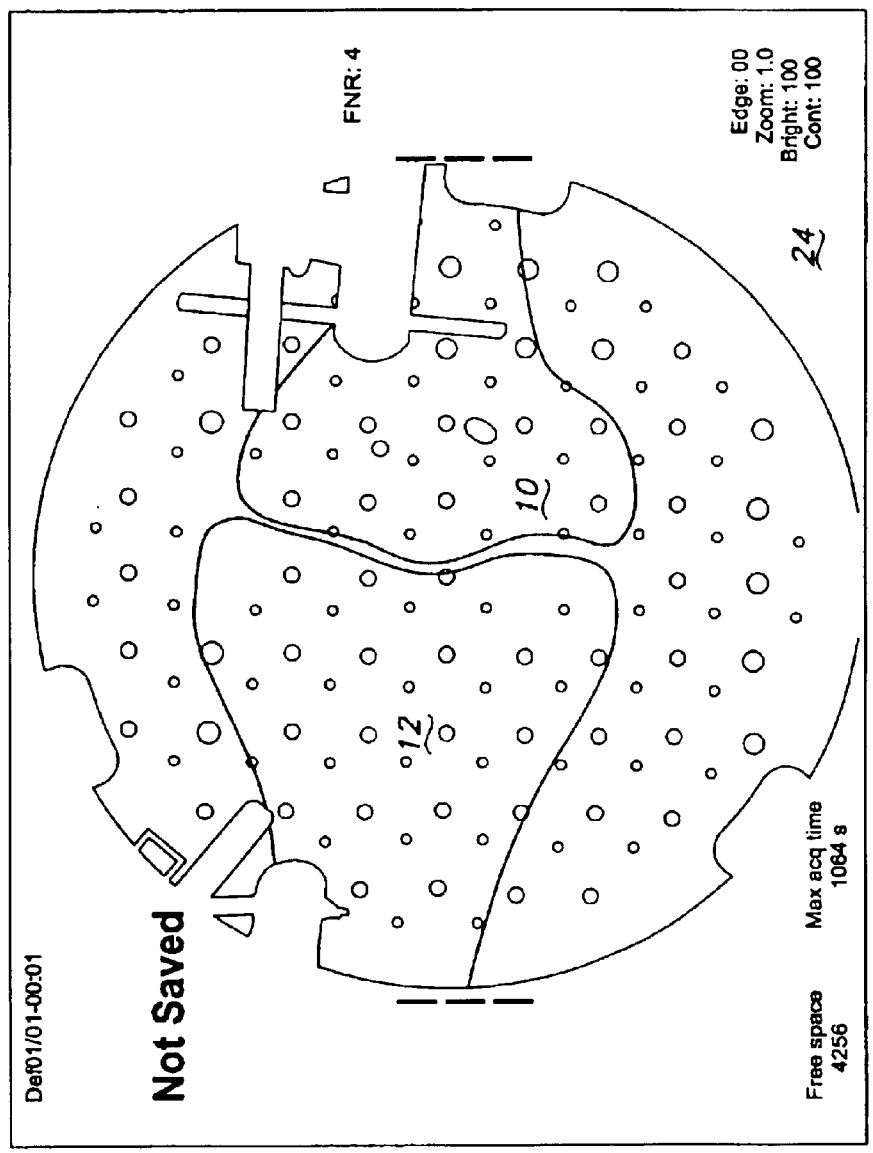
FIG. 6 is a fluoroscopic image of a knee obtained and rendered according to one embodiment of the present invention.
Figure 7:
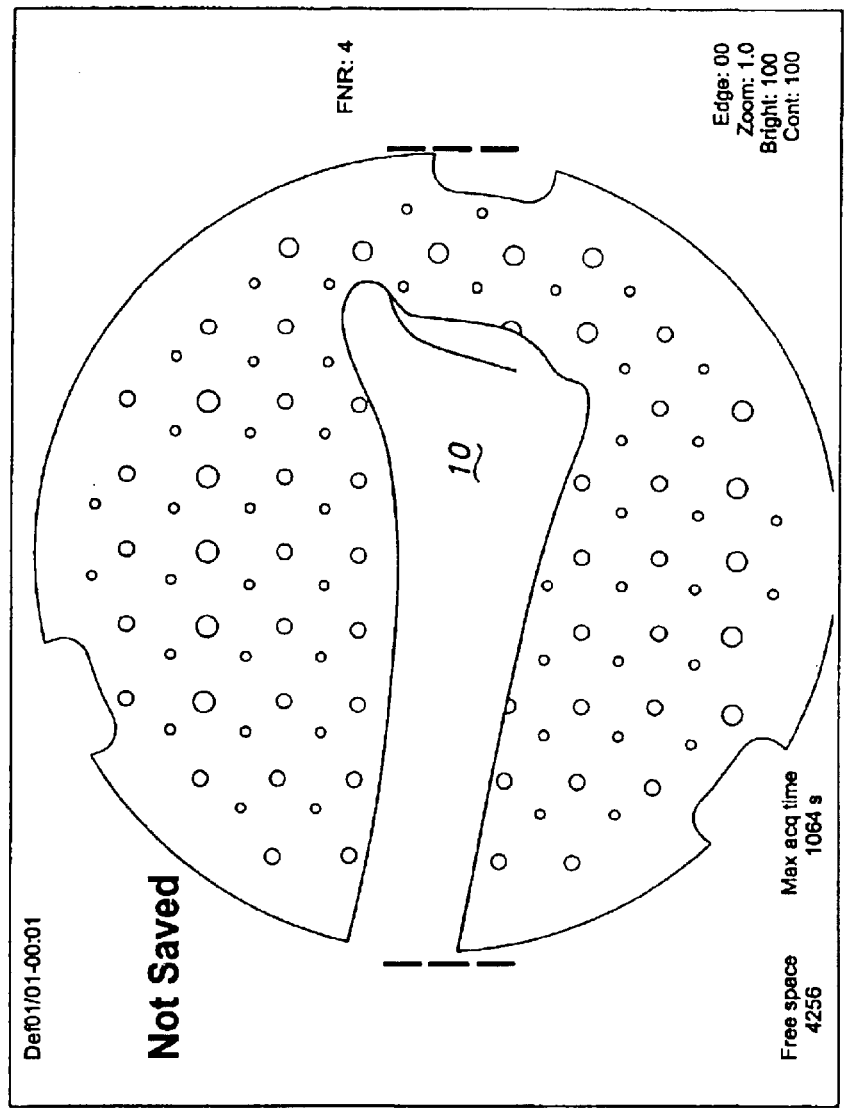
FIG. 7 is a fluoroscopic image of a tibia distal end obtained and rendered according to one embodiment of the present invention.
Figure 8:
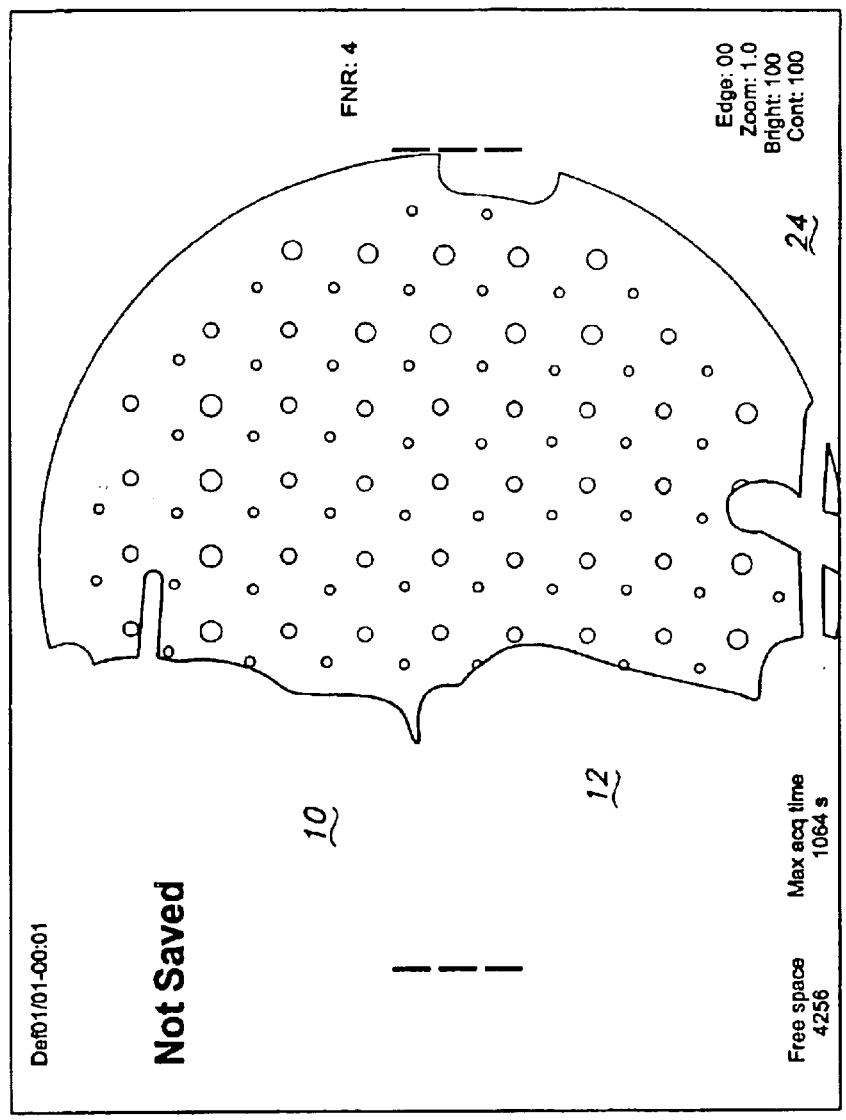
FIG. 8 is a fluoroscopic image of a lateral view of a knee obtained and rendered according to one embodiment of the present invention.
Figure 9:
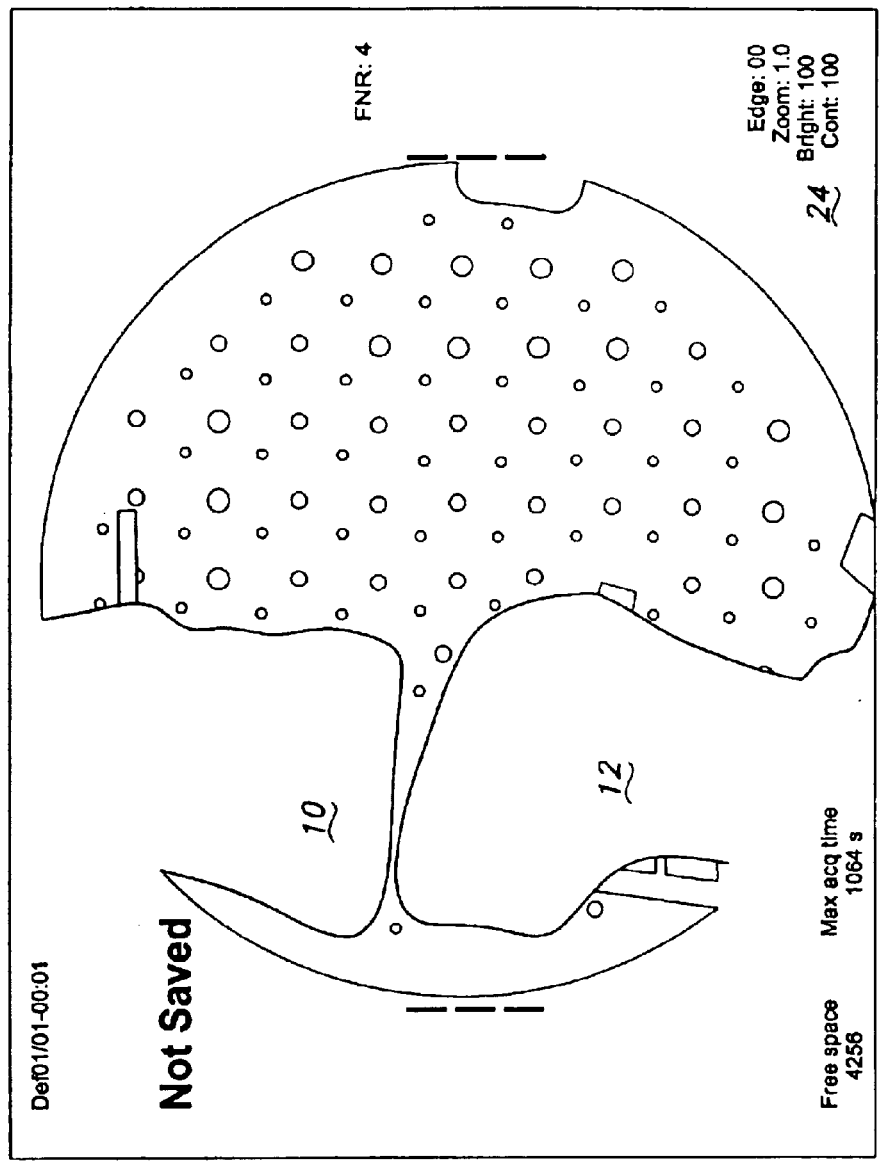
FIG. 9 is a fluoroscopic image of a lateral view of a knee obtained and rendered according to one embodiment of the present invention.
Figure 10:
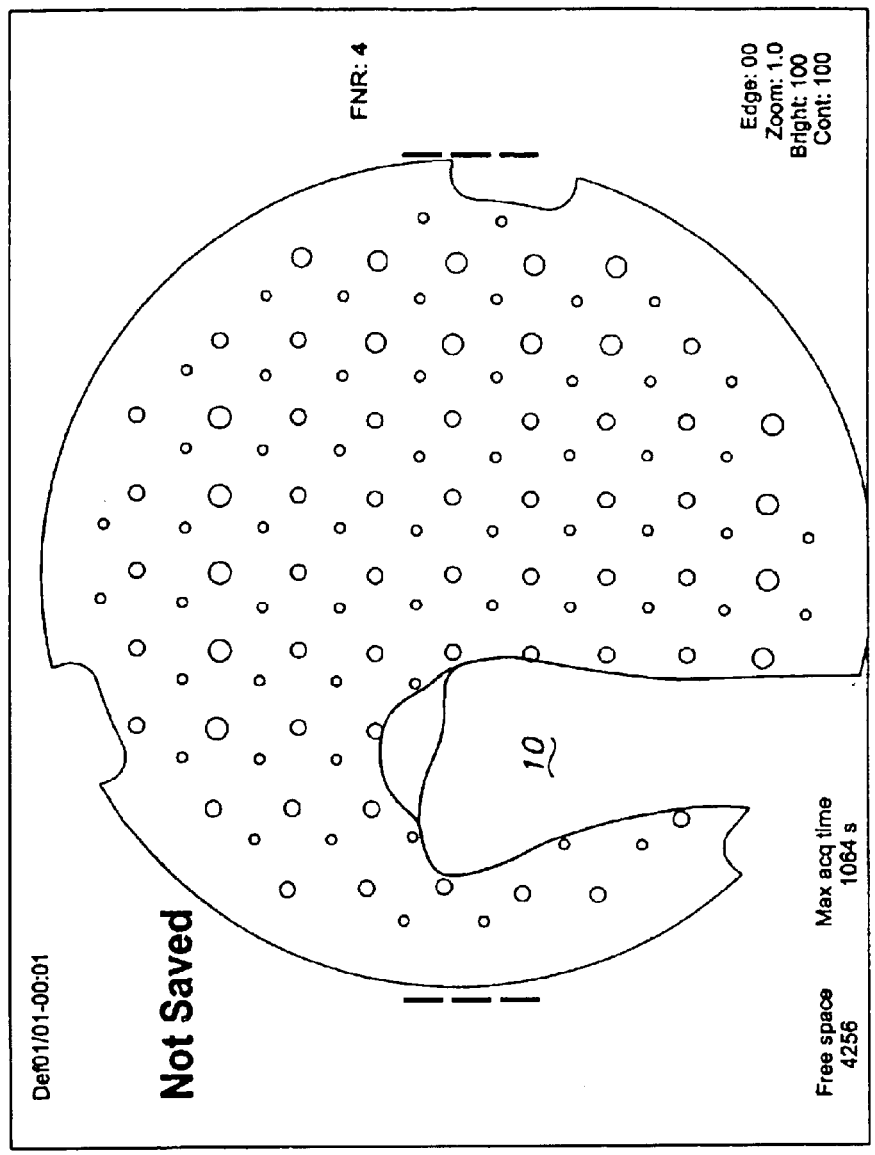
FIG. 10 is a fluoroscopic image of a lateral view of a tibia distal end obtained and rendered according to one embodiment of the present invention.

FIG. 5 shows a fluoroscopic image of the femoral head while FIG. 6 shows an anterior/posterior view of the knee which can be used to designate landmarks and establish axes or constructs such as the mechanical axis or other rotational axes. FIG. 7 shows the distal end of the tibia and FIG. 8 shows a lateral view of the knee. FIG. 9 shows another lateral view of the knee while FIG. 10 shows a lateral view of the distal end of the tibia.

Registration of Surgically Related Items

Figure 11:
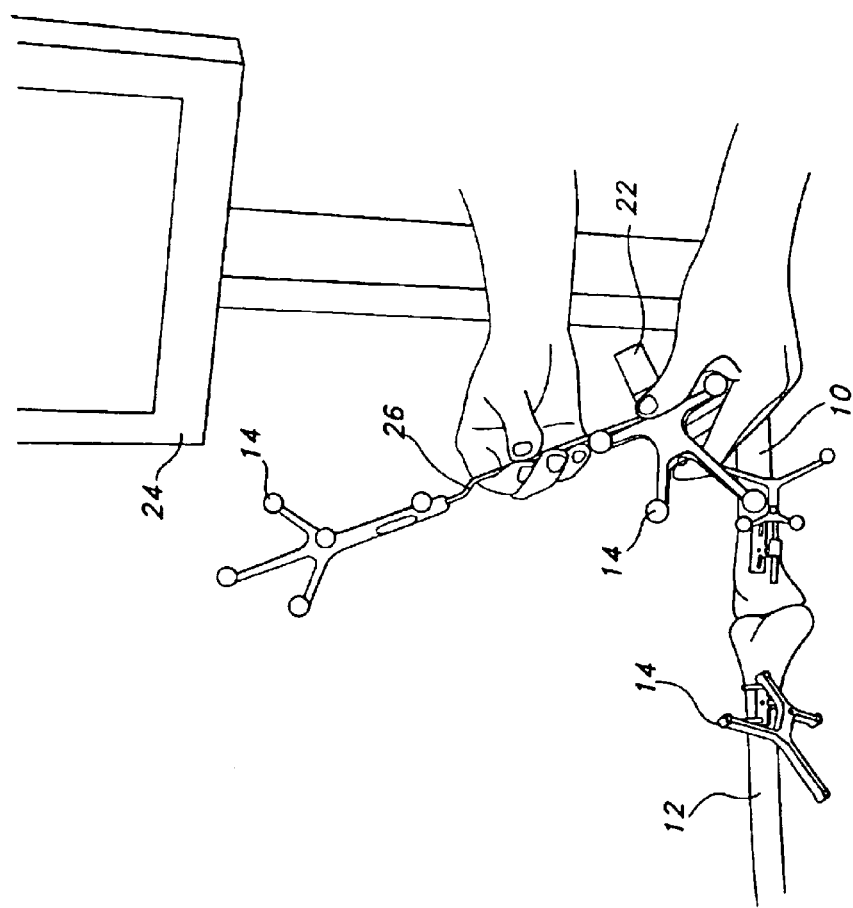
FIG. 11 shows a probe according to one embodiment of the present invention being used to register a surgically related component for tracking according to one embodiment of the present invention.
Figure 12:
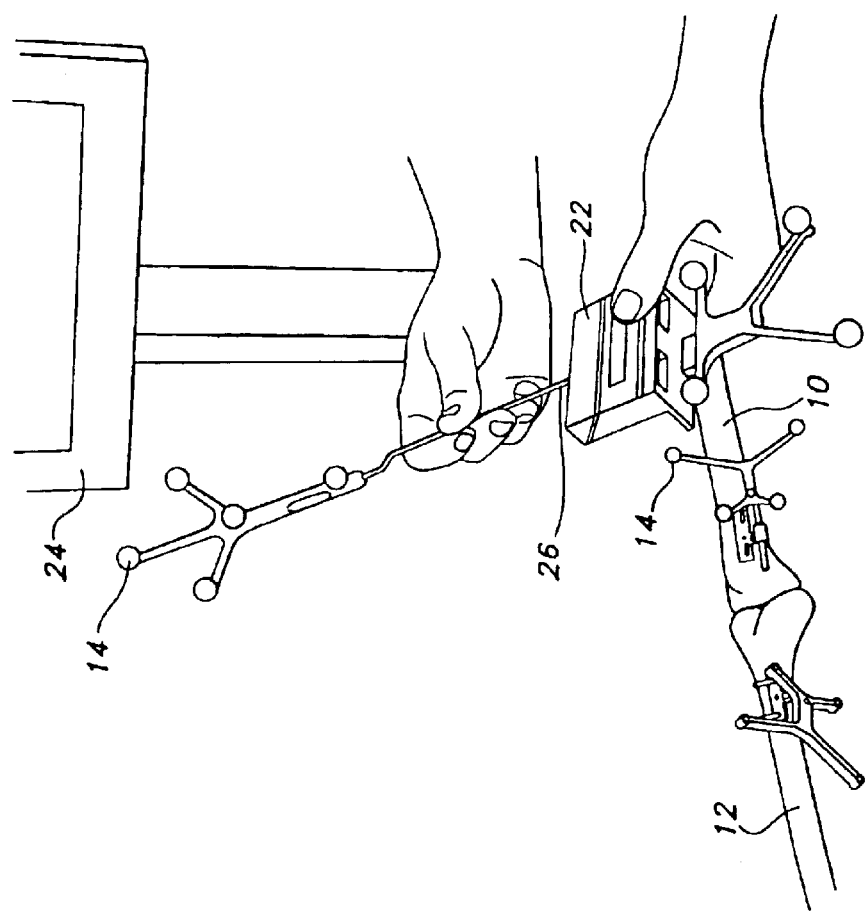
FIG. 12 shows a probe according to one embodiment of the present invention being used to register a cutting block for tracking according to one embodiment of the present invention.
Figure 13:
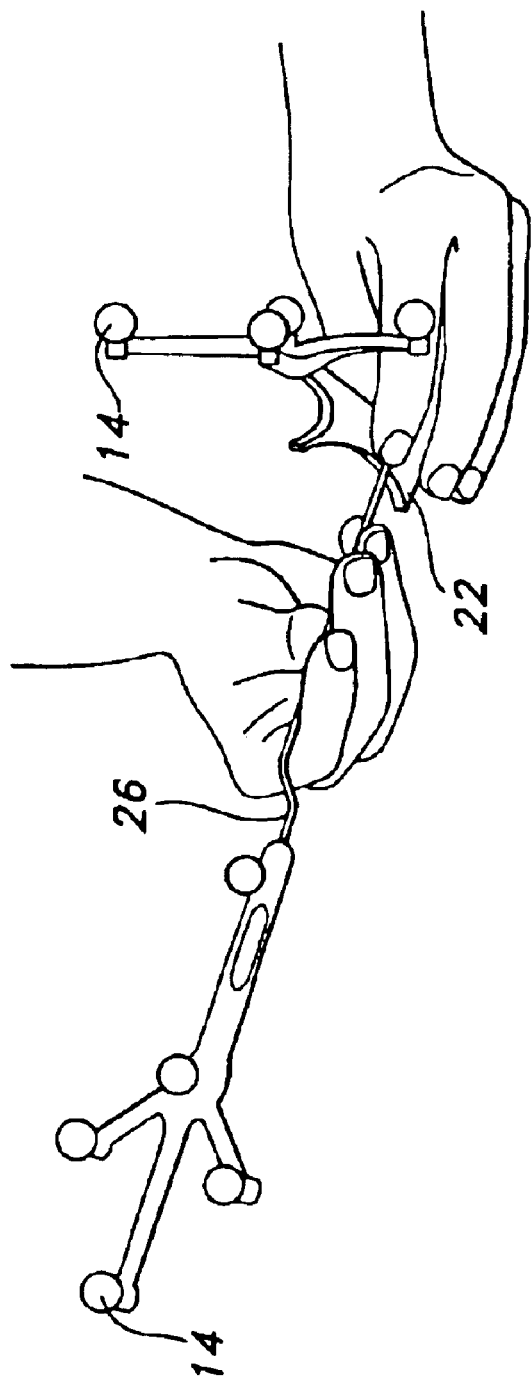
FIG. 13 shows a probe according to one embodiment of the present invention being used to register a tibial cutting block for tracking according to one embodiment of the present invention.
Figure 14:
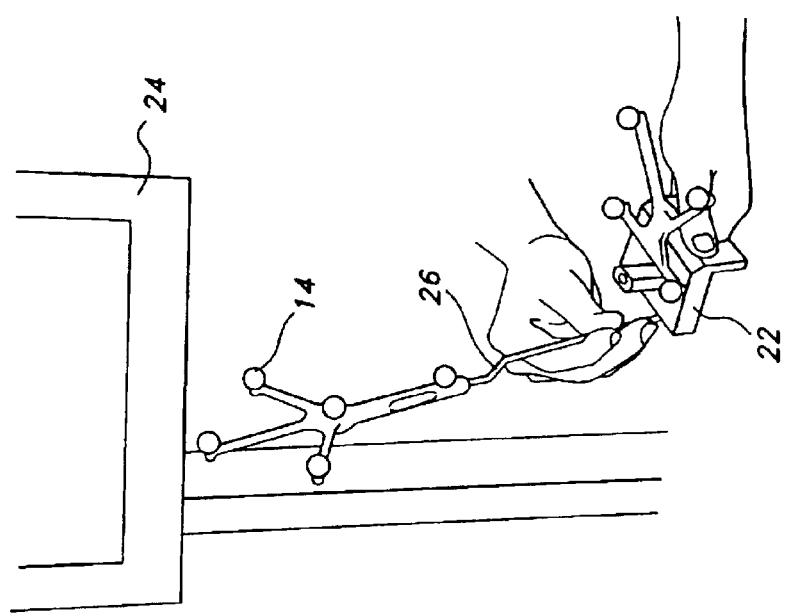
FIG. 14 shows a probe according to one embodiment of the present invention being used to register an alignment guide for tracking according to one embodiment of the present invention.

FIGS. 11–14 show designation or registration of items 22 which will be used in surgery. Registration simply means, however it is accomplished, ensuring that the computer knows which body part, item or construct corresponds to which fiducial or fiducials, and how the position and orientation of the body part, item or construct is related to the position and orientation of its corresponding fiducial or a fiducial attached to an impactor or other other component which is in turn attached to an item. Such registration or designation can be done before or after registering bone or body parts as discussed with respect to FIGS. 4–10. FIG. 11 shows a technician designating with probe 26 an item 22 such as an instrument component to which fiducial 14 is attached. The sensor 16 "sees" the position and orientation of the fiducial 14 attached to the item 22 and also the position and orientation of the fiducial 14 attached to the probe 26 whose tip is touching a landmark on the item 22. The technician designates onscreen or otherwise the identification of the item and then activates the foot pedal or otherwise instructs the computer to correlate the data corresponding to such identification, such as data needed to represent a particular cutting block component for a particular knee implant product, with the particularly shaped fiducial 14 attached to the component 22. The computer has then stored identification, position and orientation information relating to the fiducial for component 22 correlated with the data such as configuration and shape data for the item 22 so that upon registration, when sensor 16 tracks the item 22 fiducial 14 in the infrared field, monitor 24 can show the cutting block component 22 moving and turning, and properly positioned and oriented relative to the body part which is also being tracked. FIGS. 12–14 show similar registration for other instrumentation components 22.

Registration of Anatomy and Constructs

Figure 15:
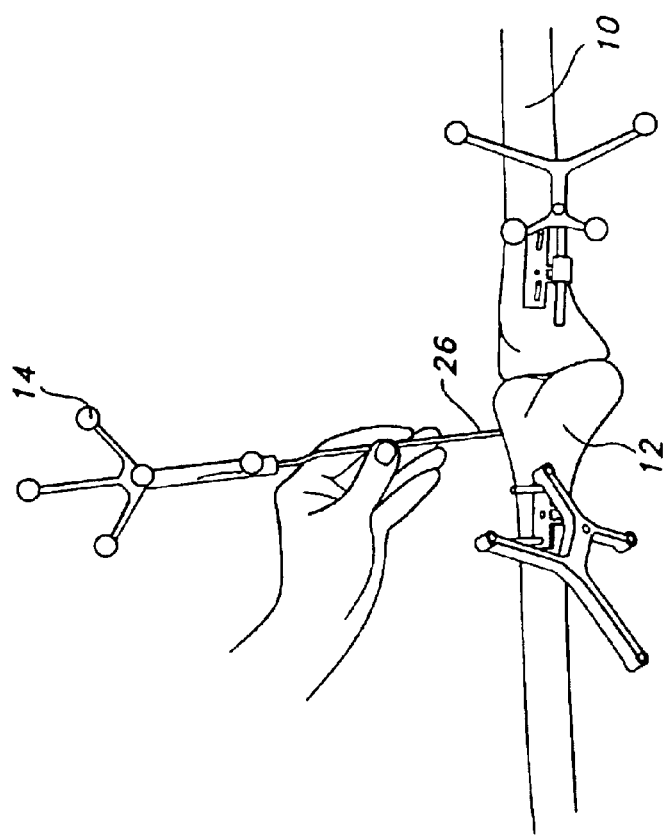
FIG. 15 shows a probe according to one embodiment of the present invention being used to designate landmarks on bone structure for tracking according one embodiment of the present invention.
Figure 16:
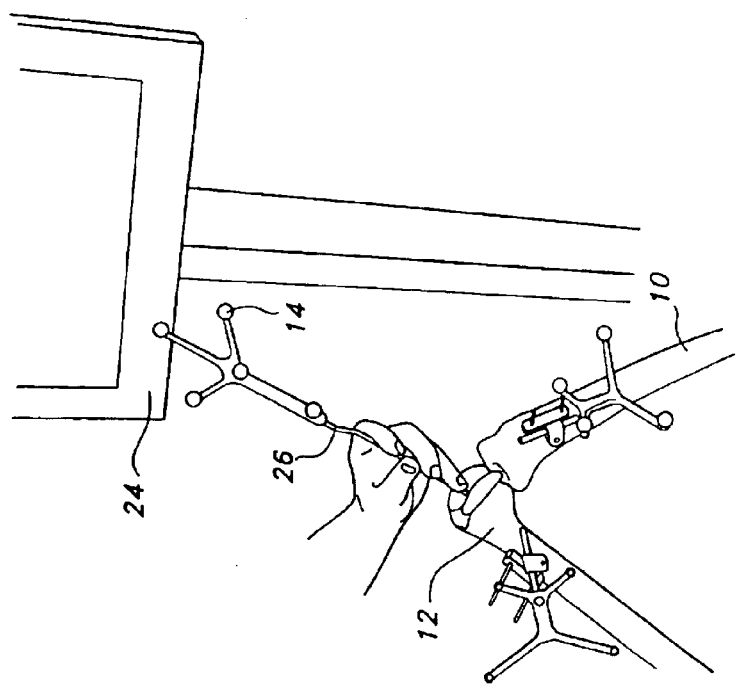
FIG. 16 is another view of a probe according to one embodiment of the present invention being used to designate landmarks on bone structure for tracking according one embodiment of the present invention.
Figure 17:
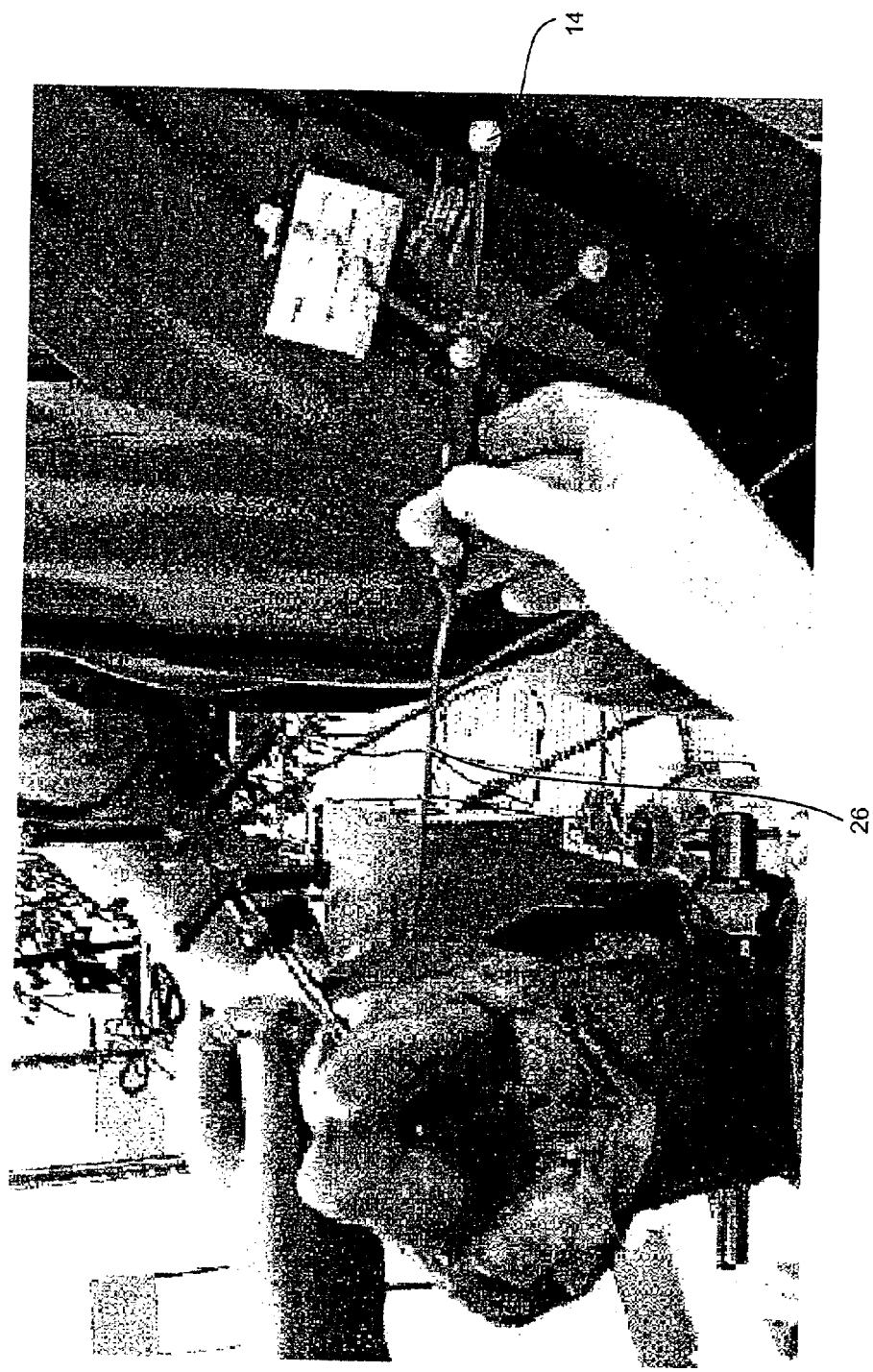
FIG. 17 is another view of a probe according to one embodiment of the present invention being used to designate landmarks on bone structure for tracking according one embodiment of the present invention.

Similarly, the mechanical axis and other axes or constructs of body parts 10 and 12 can also be "registered" for tracking by the system. Again, the system has employed a fluoroscope to obtain images of the femoral head, knee and ankle of the sort shown in FIGS. 4–10. The system correlates such images with the position and orientation of the C-arm and the patient anatomy in real time as discussed above with the use of fiducials 14 placed on the body parts before image acquisition and which remain in position during the surgical procedure. Using these images and/or the probe, the surgeon can select and register in the computer 18 the center of the femoral head and ankle in orthogonal views, usually anterior/posterior and lateral, on a touch screen. The surgeon uses the probe to select any desired anatomical landmarks or references at the operative site of the knee or on the skin or surgical draping over the skin, as on the ankle. These points are registered in three dimensional space by the system and are tracked relative to the fiducials on the patient anatomy which are preferably placed intraoperatively. FIG. 15 shows the surgeon using probe 26 to designate or register landmarks on the condylar portion of femur 12 using probe 26 in order to feed to the computer 18 the position of one point needed to determine, store, and display the epicondylar axis. (See FIG. 20 which shows the epicondylar axis and the anterior-posterior plane and for lateral plane.) Although registering points using actual bone structure such as in FIG. 15 is one preferred way to establish the axis, a cloud of points approach by which the probe 26 is used to designate multiple points on the surface of the bone structure can be employed, as can moving the body part and tracking movement to establish a center of rotation as discussed above. Once the center of rotation for the femoral head and the condylar component have been registered, the computer is able to calculate, store, and render, and otherwise use data for, the mechanical axis of the femur 12. FIG. 17 once again shows the probe 26 being used to designate points on the condylar component of the femur 12.

Figure 18:
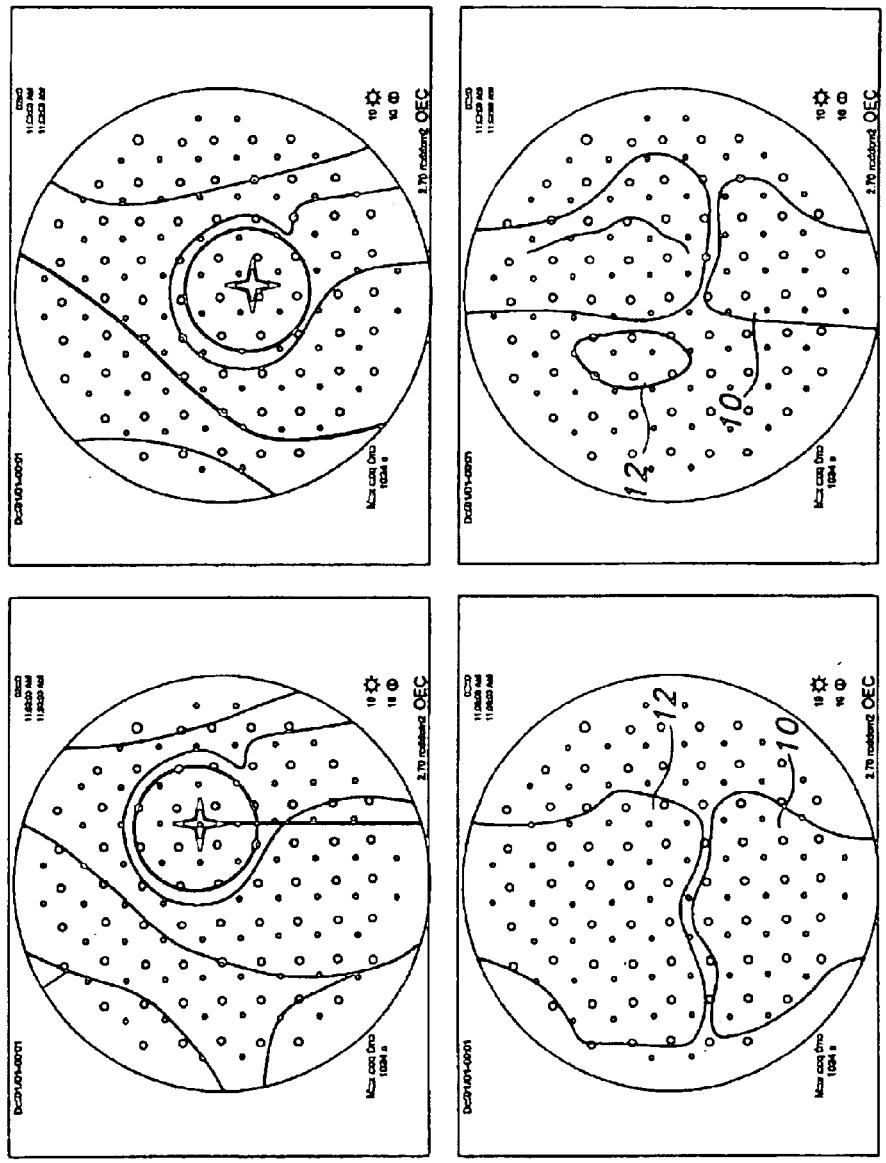
FIG. 18 is a screen face produced according to one embodiment of the present invention during designation of landmarks to determine a femoral mechanical axis.
Figure 19:
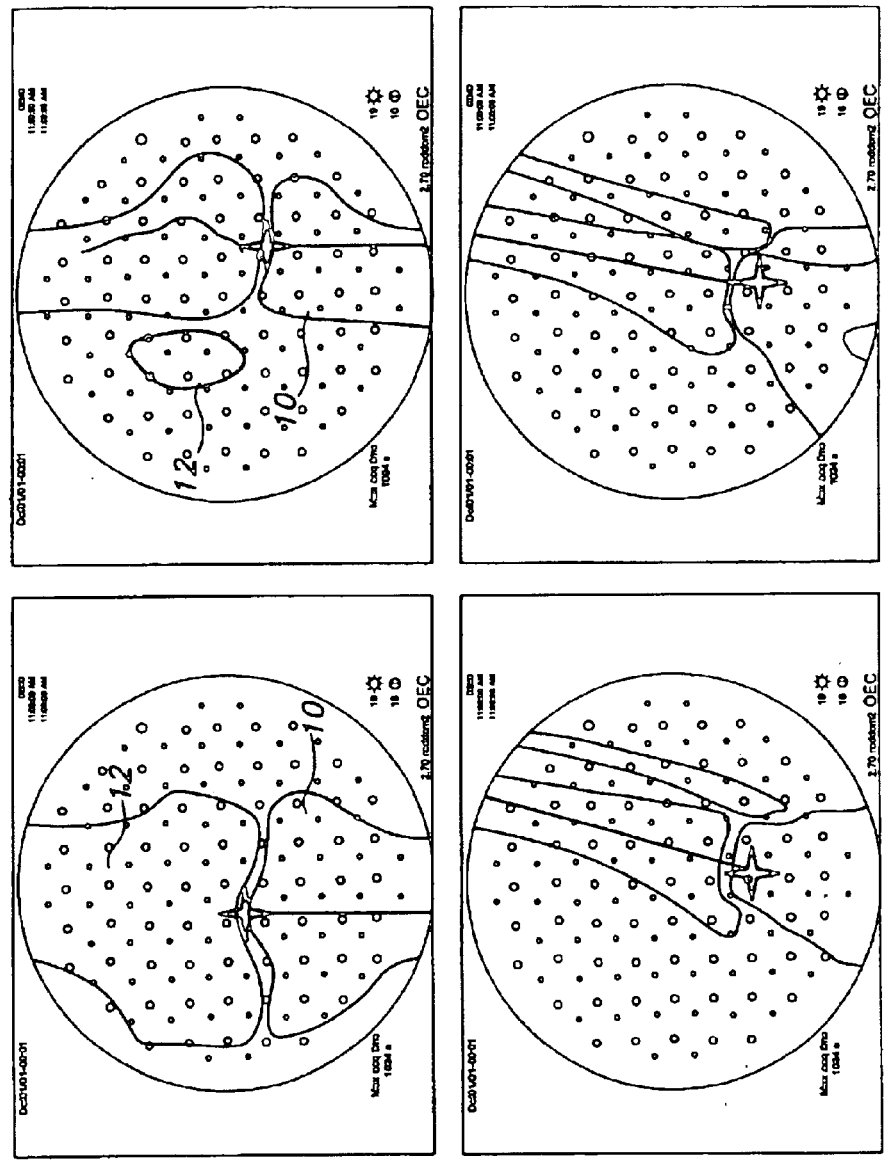
FIG. 19 is a view produced according to one embodiment of the present invention during designation of landmarks to determine a tibial mechanical axis.

FIG. 18 shows the onscreen images being obtained when the surgeon registers certain points on the bone surface using the probe 26 in order to establish the femoral mechanical axis. The tibial mechanical axis is then established by designating points to determine the centers of the proximal and distal ends of the tibia so that the mechanical axis can be calculated, stored, and subsequently used by the computer 18. FIG. 20 shows designated points for determining the epicondylar axis, both in the anterior/posterior and lateral planes while FIG. 21 shows such determination of the anterior-posterior axis as rendered onscreen. The posterior condylar axis is also determined by designating points or as otherwise desired, as rendered on the computer generated geometric images overlain or displayed in combination with the fluoroscopic images, all of which are keyed to fiducials 14 being tracked by sensors 16.

Figure 23:
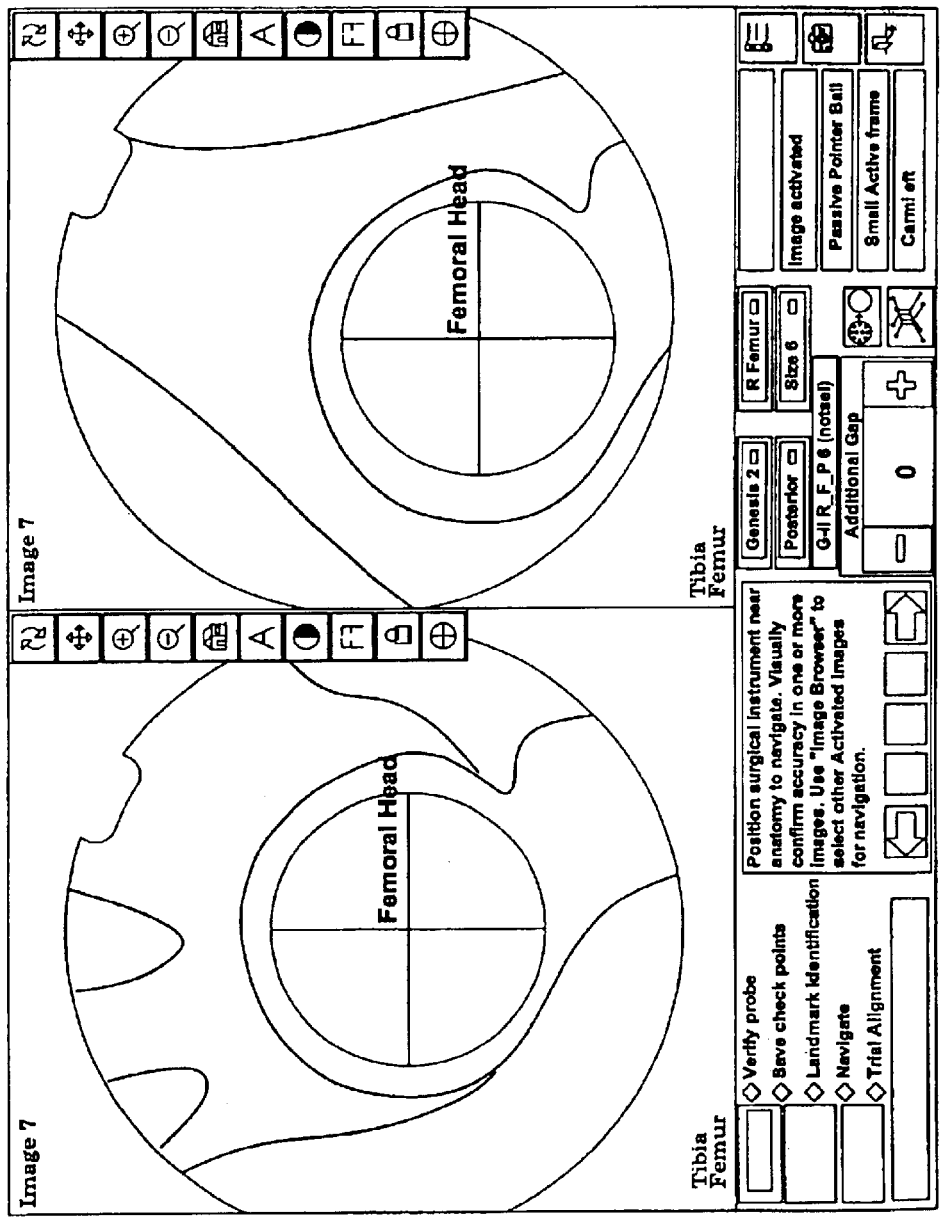
FIG. 23 is a screen face according to one embodiment of the present invention which presents graphic indicia which may be employed to help determine reference locations within bone structure.

FIG. 23 shows an adjustable circle graphic which can be generated and presented in combination with orthogonal fluoroscopic images of the femoral head, and tracked by the computer 18 when the surgeon moves it on screen in order to establish the centers of the femoral head in both the anterior-posterior and lateral planes.

Figure 24:
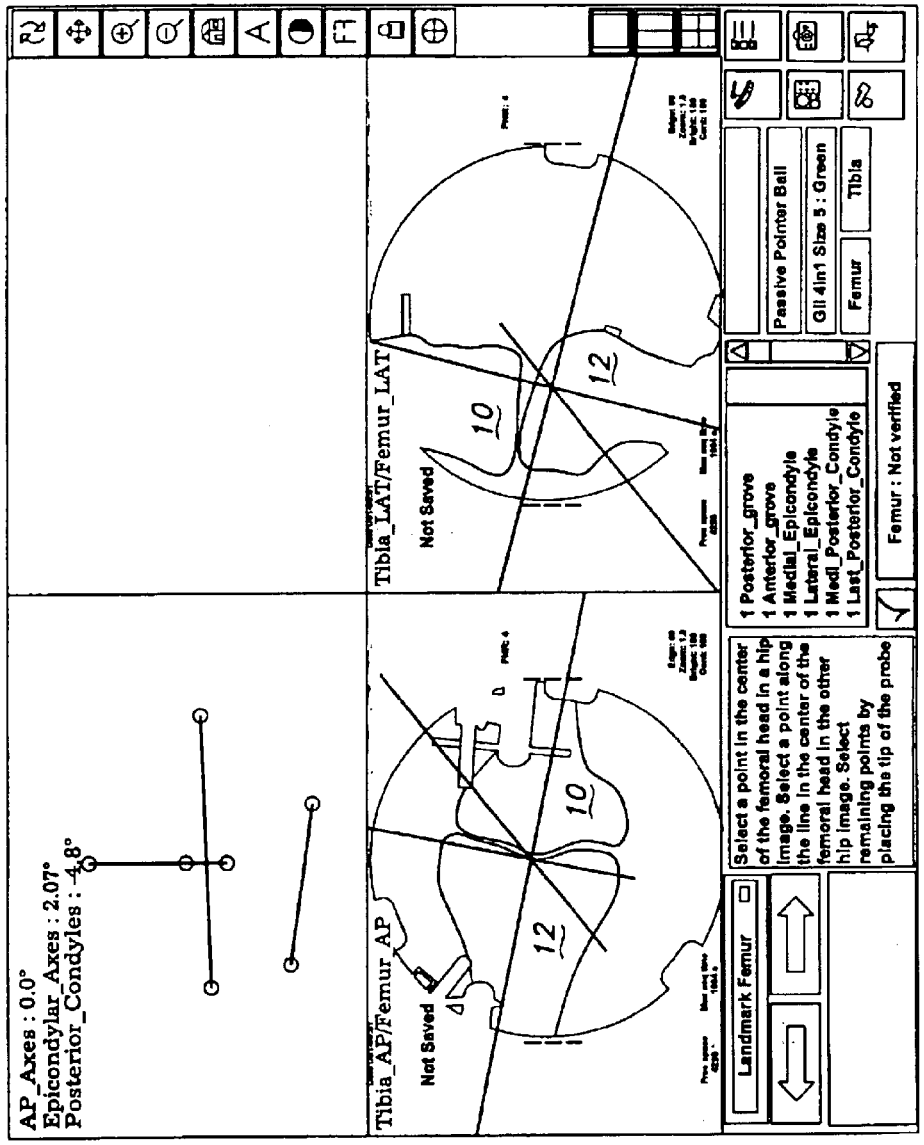
FIG. 24 is a screen face according to one embodiment of the present invention showing mechanical and other axes which have been established according to one embodiment of the present invention.

FIG. 24 is an onscreen image showing the anterior-posterior axis, epicondylar axis and posterior condylar axis from points which have been designated as described above. These constructs are generated by the computer 18 and presented on monitor 24 in combination with the fluoroscopic images of the femur 12, correctly positioned and oriented relative thereto as tracked by the system. In the fluoroscopic/computer generated image combination shown at left bottom of FIG. 24, a "sawbones" knee as shown in certain drawings above which contains radio opaque materials is represented fluoroscopically and tracked using sensor 16 while the computer generates and displays the mechanical axis of the femur 12 which runs generally horizontally. The epicondylar axis runs generally vertically, and the anterior/posterior axis runs generally diagonally. The image at bottom right shows similar information in a lateral view. Here, the anterior-posterior axis runs generally horizontally while the epicondylar axis runs generally diagonally, and the mechanical axis generally vertically.

FIG. 24, as is the case with a number of screen presentations generated and presented by the system of FIGS. 4–64, also shows at center a list of landmarks to be registered in order to generate relevant axes and constructs useful in navigation, positioning and assessment during surgery. Textural cues may also be presented which suggest to the surgeon next steps in the process of registering landmarks and establishing relevant axes. Such instructions may be generated as the computer 18 tracks, from one step to the next, registration of items 22 and bone locations as well as other measures being taken by the surgeon during the surgical operation.

Figure 25:
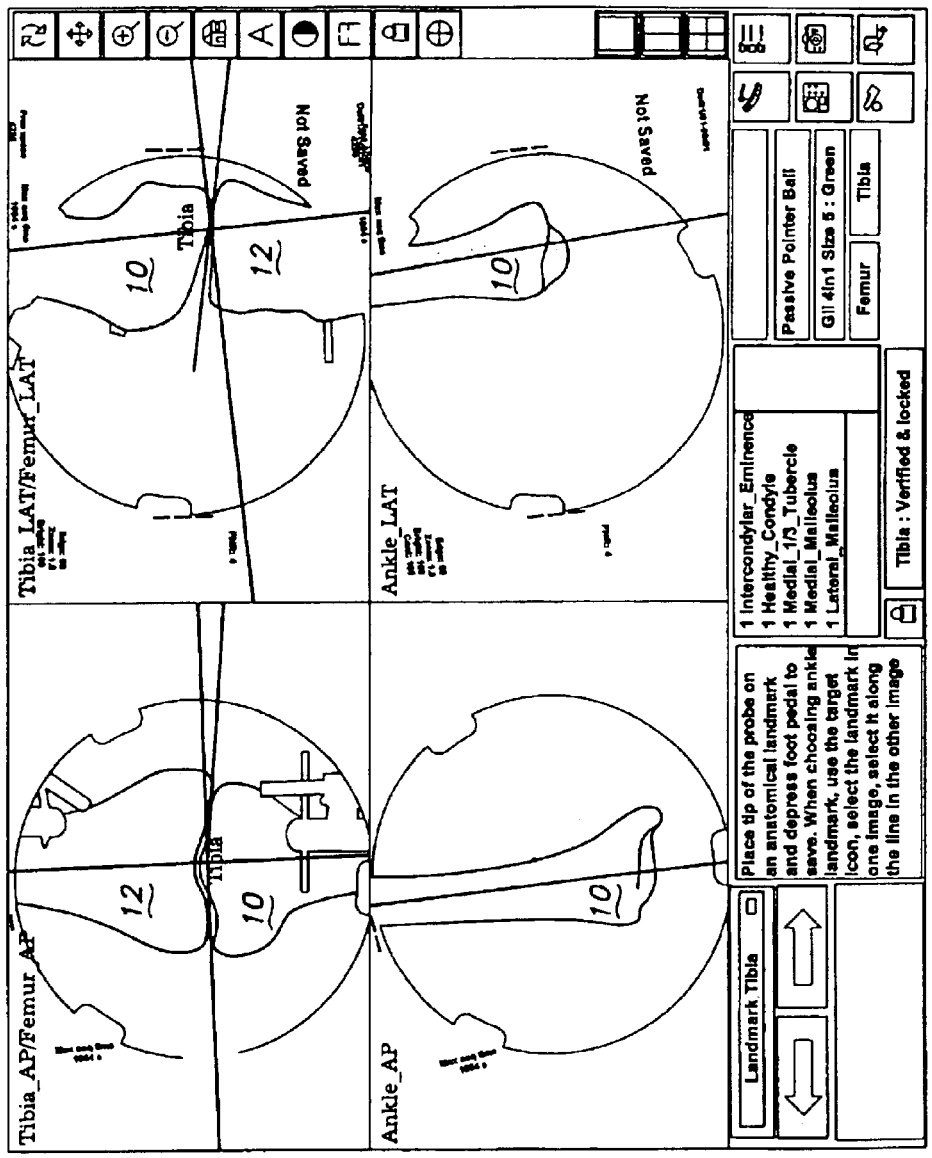
FIG. 25 is another screen face according to one embodiment of the present invention showing mechanical and other axes which have been established according to one embodiment of the present invention.

FIG. 25 shows mechanical, lateral, anterior-posterior axes for the tibia according to points are registered by the surgeon.

Figure 26:
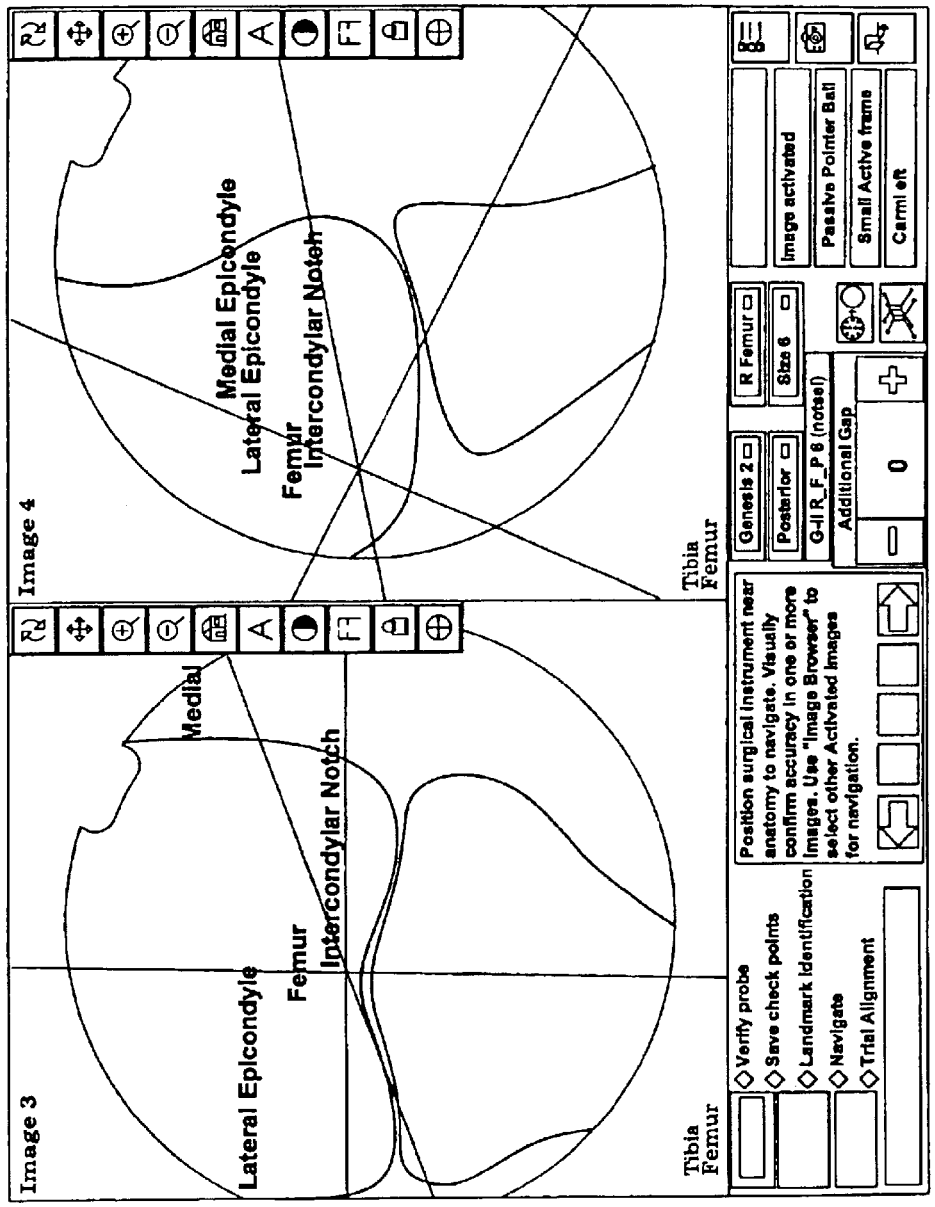
FIG. 26 is another screen face according to one embodiment of the present invention showing mechanical and other axes which have been established according to one embodiment of the present invention.

FIG. 26 is another onscreen image showing the axes for the femur 12.

Modifying Bone

After the mechanical axis and other rotation axes and constructs relating to the femur and tibia are established, instrumentation can be properly oriented to resect or modify bone in order to fit trial components and implant components properly according to the embodiment of the invention shown in FIGS. 4–64. Instrumentation such as, for instance, cutting blocks, to which fiducials 14 are mounted, can be employed. The system can then track instrumentation as the surgeon manipulates it for optimum positioning. In other words, the surgeon can "navigate" the instrumentation for optimum positioning using the system and the monitor. In this manner, instrumentation may be positioned according to the system of this embodiment in order to align the ostetomies to the mechanical and rotational axes or reference axes on an extramedullary rod that does not violate the canal, on an intramedullary rod, or on any other type of rod. The touchscreen 24 can then also display the instrument such as the cutting block and/or the implant relative to the instrument and the rod during this process, in order, among other things, properly to select size of implant and perhaps implant type. As the instrument moves, the varus/valgus, flexion/extension and internal/external rotation of the relative component position can be calculated and shown with respect to the referenced axes; in the preferred embodiment, this can be done at a rate of six cycles per second or faster. The instrument position is then fixed in the computer and physically and the bone resections are made.

Figure 27:
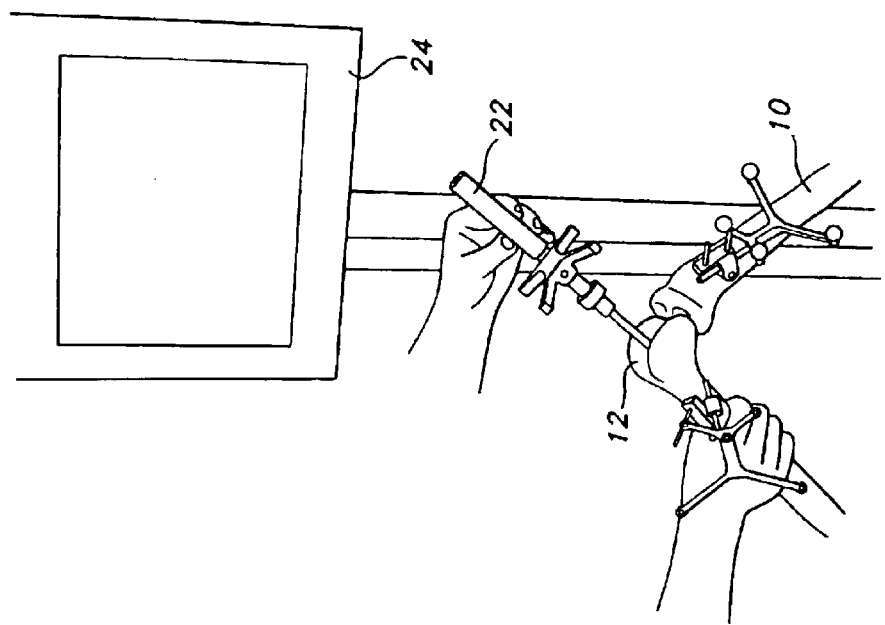
FIG. 27 shows navigation and placement of an extramedullary rod according to one embodiment of the present invention.
Figure 29:
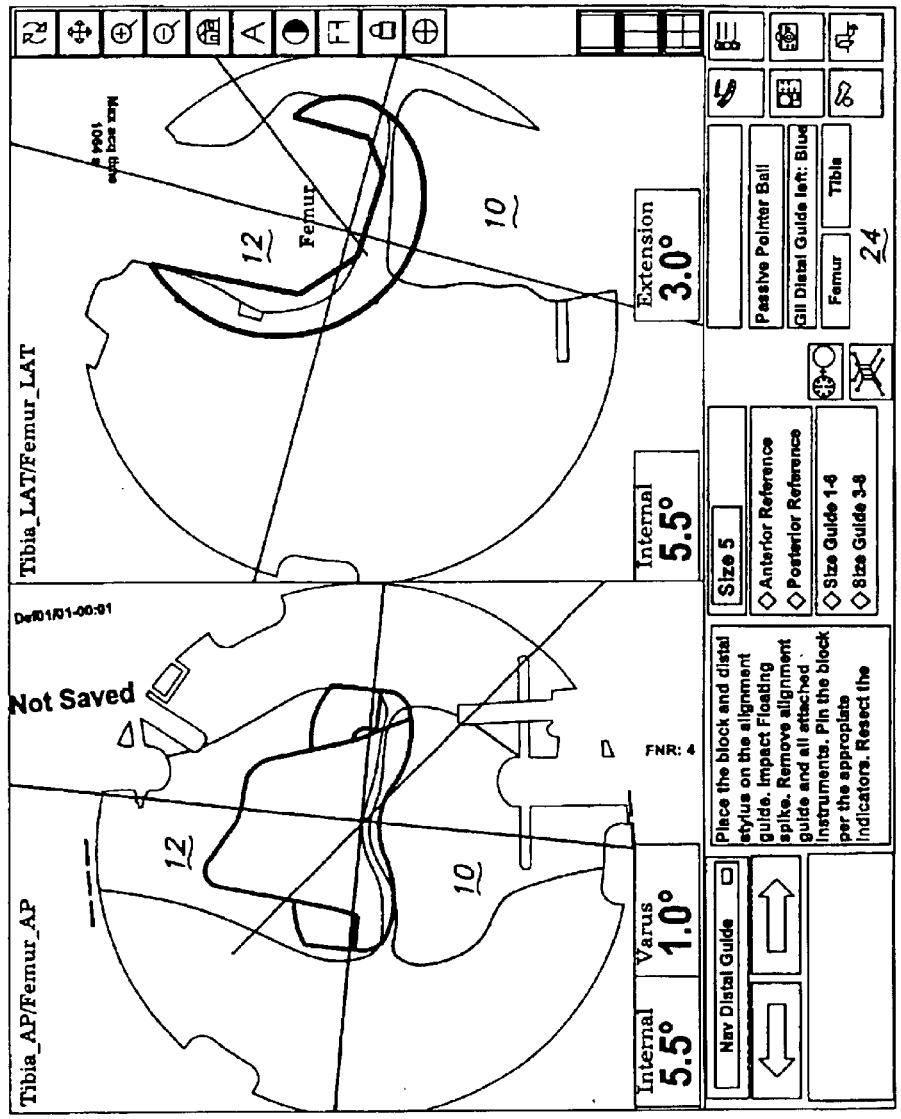
FIG. 29 is a screen face produced according to one embodiment of the present invention which assists in navigation and/or placement of an extramedullary rod.

FIG. 27 shows orientation of an extramedullary rod to which a fiducial 14 is attached via impactor 22. The surgeon views the screen 24 which has an image as shown in FIG. 29 of the rod overlain on or in combination with the femur 12 fluoroscopic image as the two are actually positioned and oriented relative to one another in space. The surgeon then navigates the rod into place preferably along the mechanical axis of the femur and drives it home with appropriate mallet or other device. The present invention thus avoids the need to bore a hole in the metaphysis of the femur and place a reamer or other rod into the medullary canal which can cause fat embolism, hemorrhaging, infection and other untoward and undesired effects.

Figure 28:
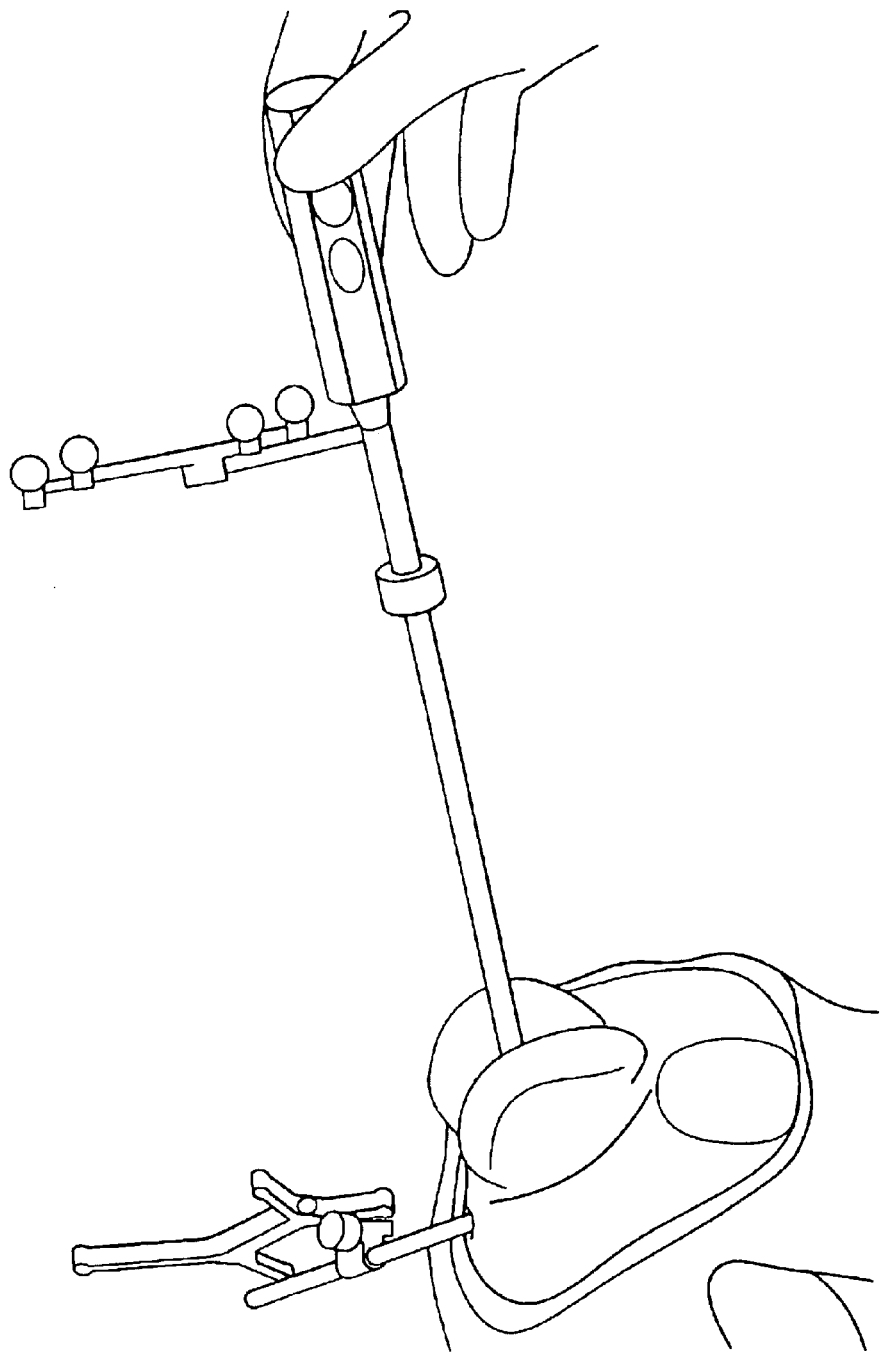
FIG. 28 is another view showing navigation and placement of an extramedullary rod according to one embodiment of the present invention.
Figure 30:
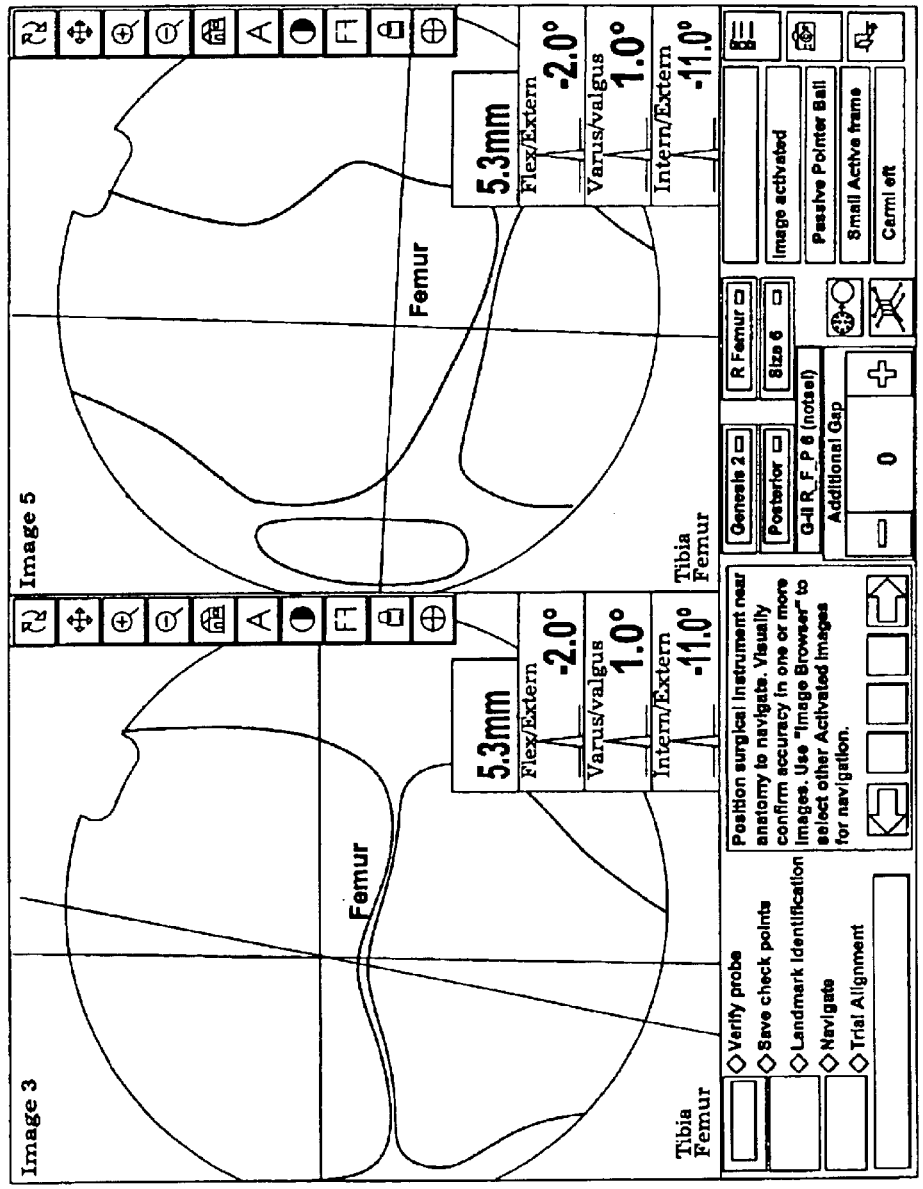
FIG. 30 is another view of a screen face produced according to one embodiment of the present invention which assists in navigation and/or placement of an extramedullary rod.

FIG. 28 also shows the extramedullary rod being located. FIG. 29 shows fluoroscopic images, both anterior-posterior and lateral, with axes, and with a computer generated and tracked image of the rod superposed or in combination with the fluoroscopic images of the femur and tibia. FIG. 30 shows the rod superposed on the femoral fluoroscopic image similar to what is shown in FIG. 29.

FIG. 29 also shows other information relevant to the surgeon such as the name of the component being overlain on the femur image (new EM nail), suggestions or instructions at the lower left, and angle of the rod in varus/valgus and extension relative to the axes. Any or all of this information can be used to navigate and position the rod relative to the femur. At a point in time during or after placement of the rod, its tracking may be "handed off" from the impactor fiducial 14 to the femur fiducal 14 as discussed below.

Figure 31:
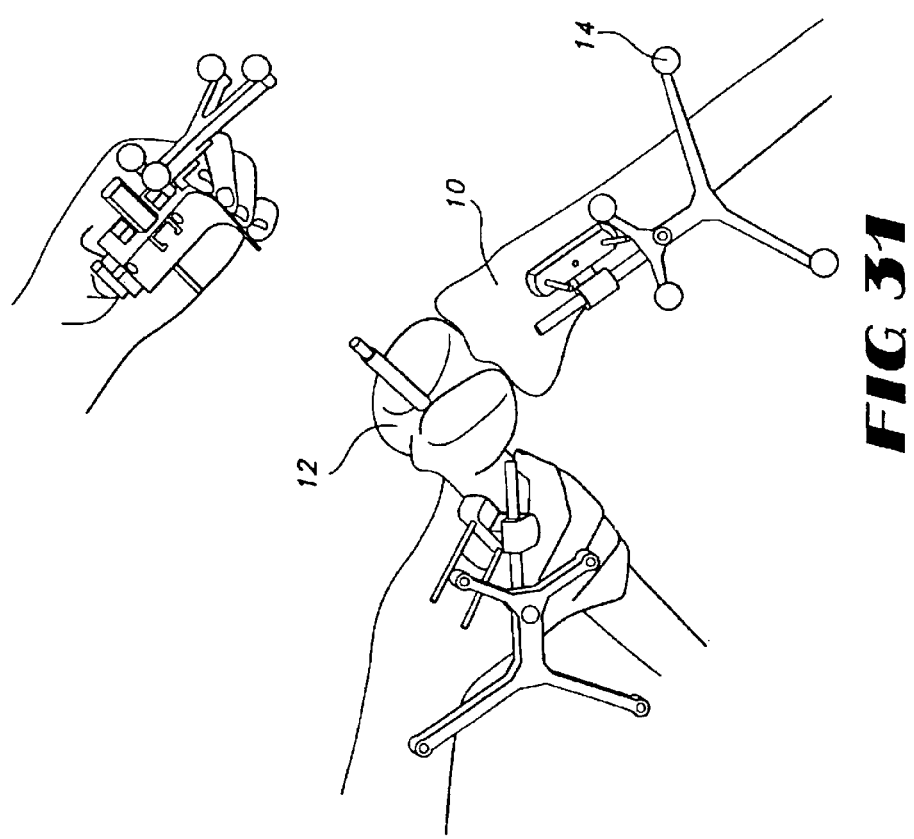
FIG. 31 is a view which shows navigation and placement of an alignment guide according to one embodiment of the present invention.
Figure 32:
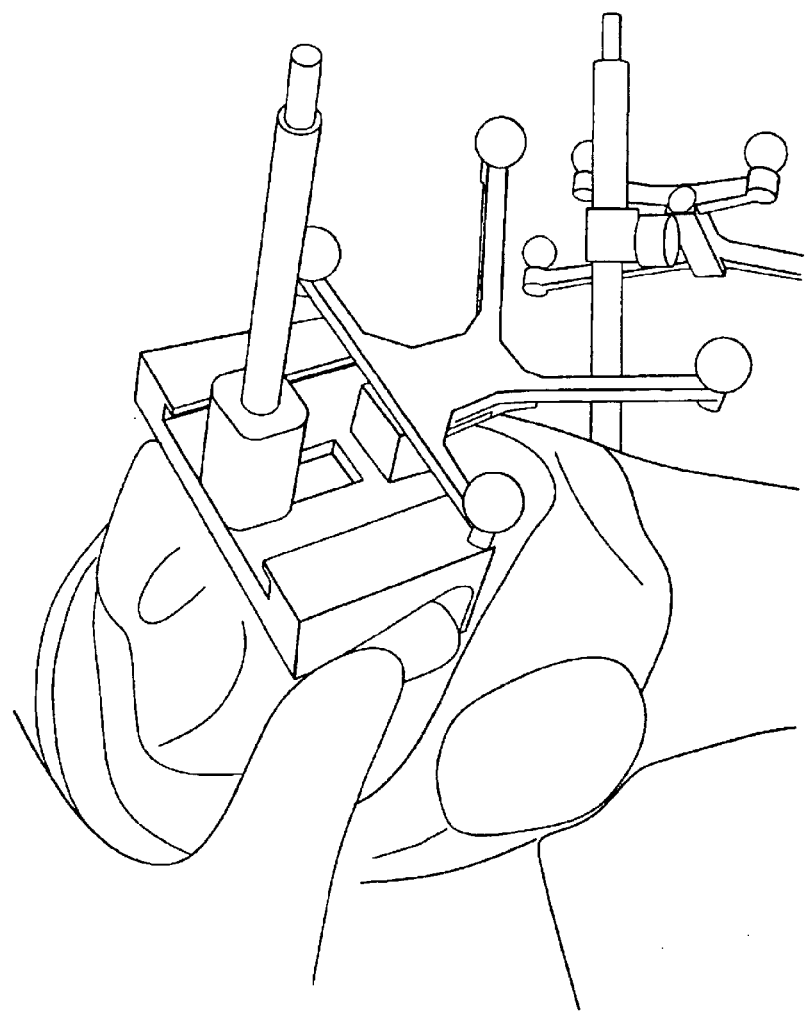
FIG. 32 is another view which shows navigation and placement of an alignment guide according to one embodiment of the present invention.
Figure 33:
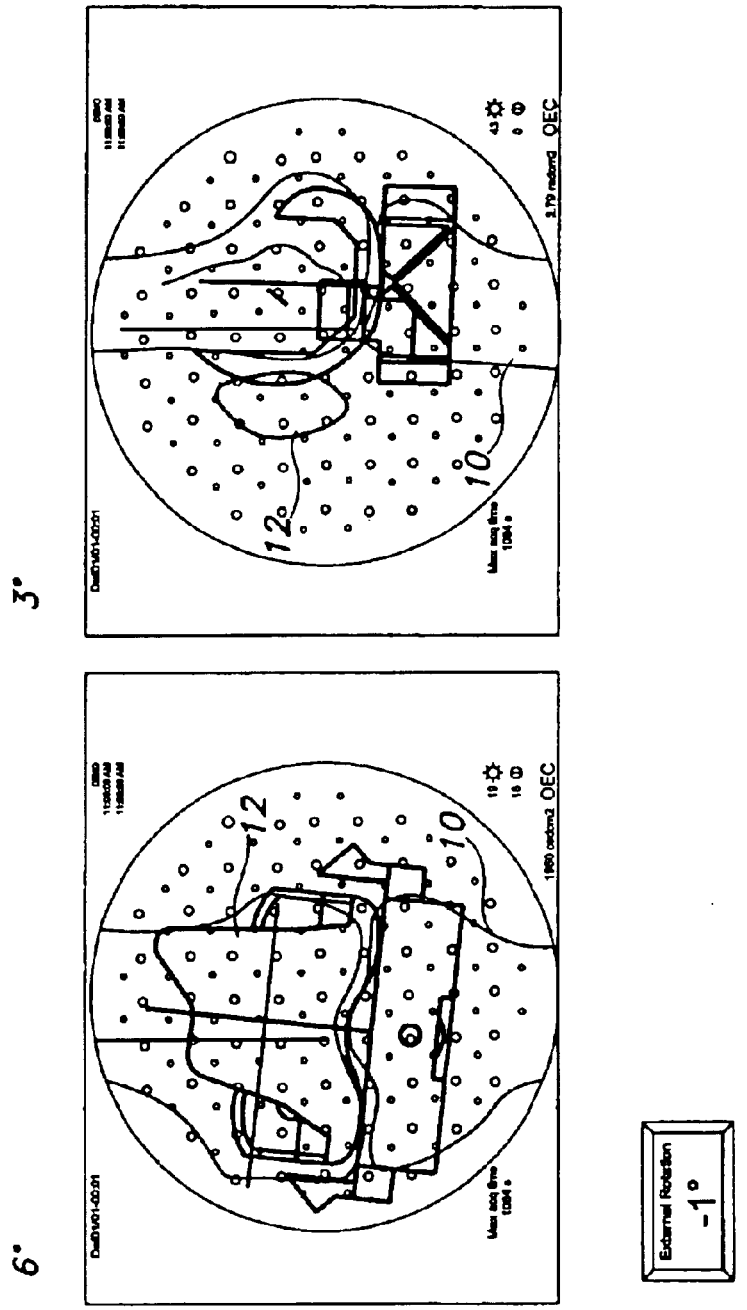
FIG. 33 is a screen face which shows a fluoroscopic image of bone in combination with computer generated images of axes and components in accordance with one embodiment of the present invention.
Figure 35:
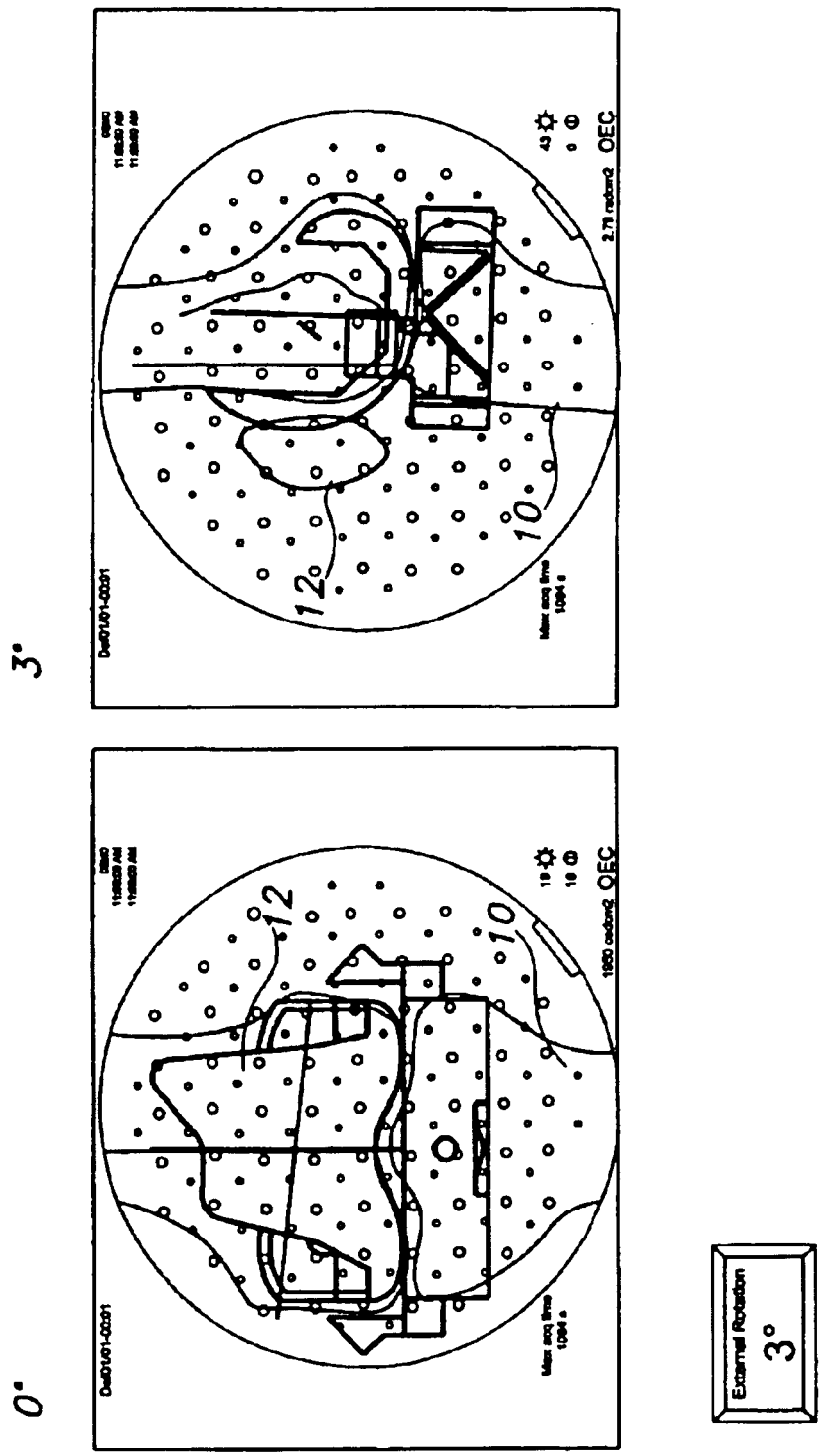
FIG. 35 is a screen face which shows a fluoroscopic image of bone in combination with computer generated images of axes and components in accordance with one embodiment of the present invention.
Figure 36:
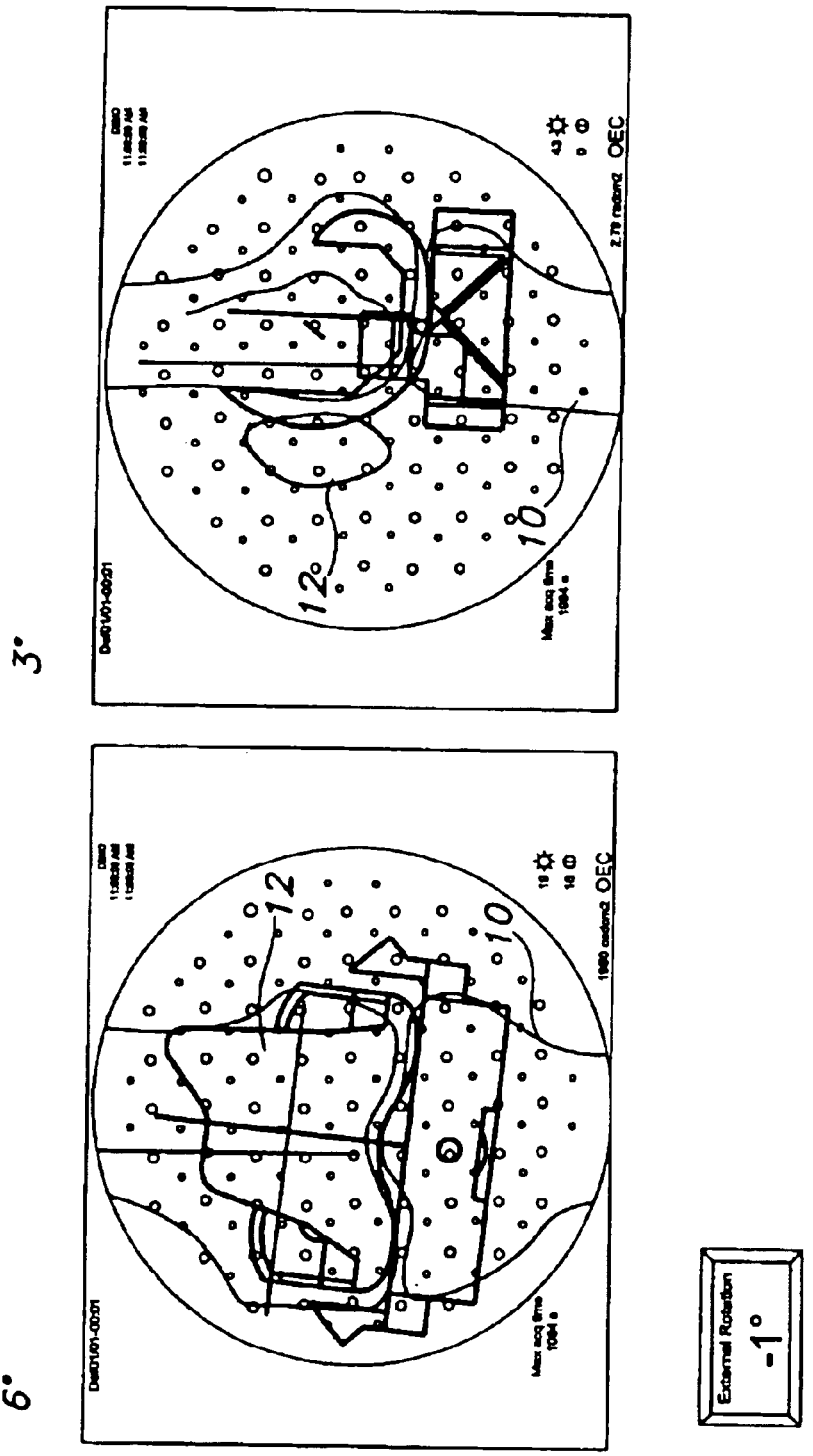
FIG. 36 is a screen face which shows a fluoroscopic image of bone in combination with computer generated images of axes and components in accordance with one embodiment of the present invention.
Figure 37:
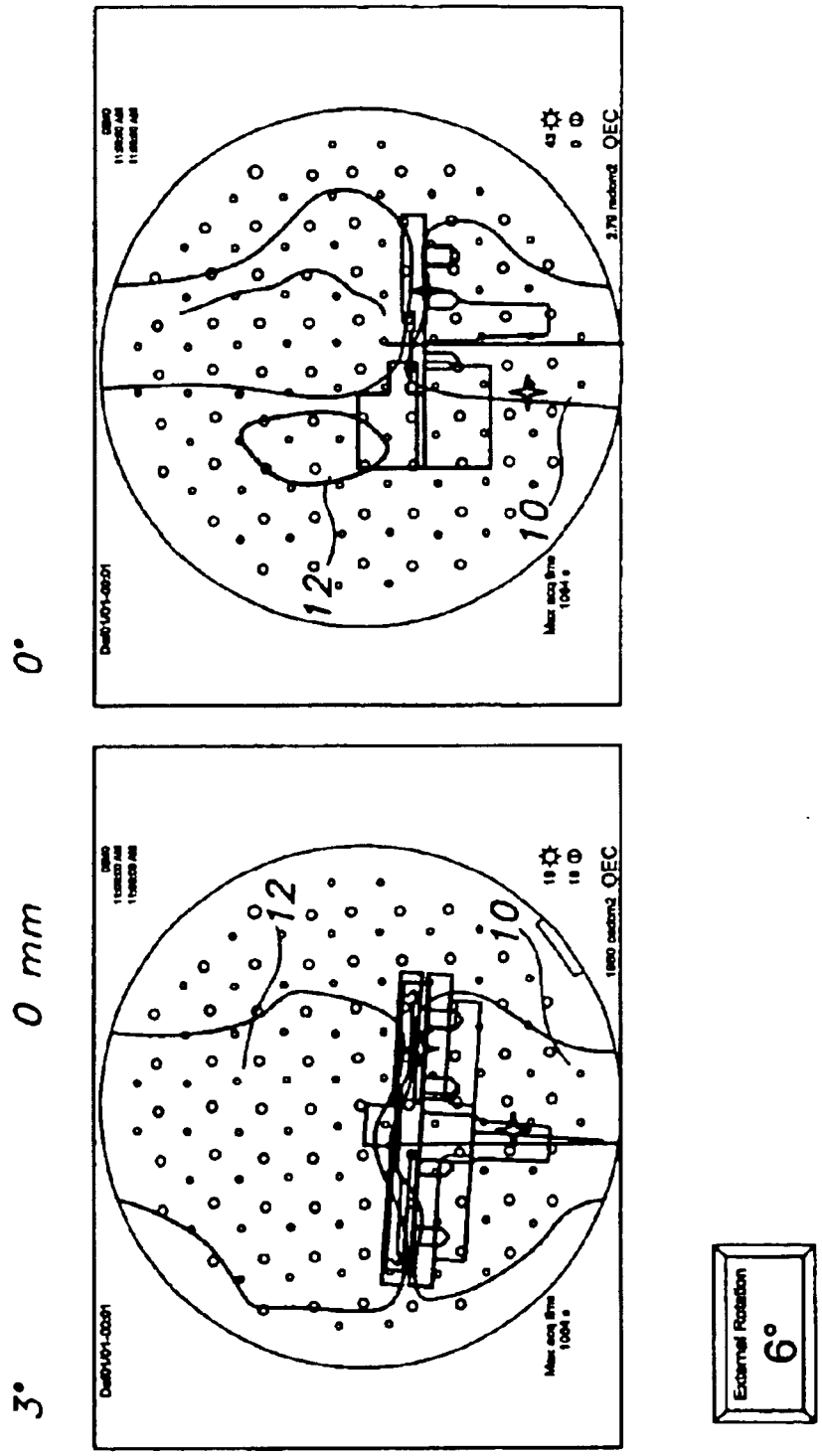
FIG. 37 is a screen face which shows a fluoroscopic image of bone in combination with computer generated images of axes and components in accordance with one embodiment of the present invention.
Figure 38:
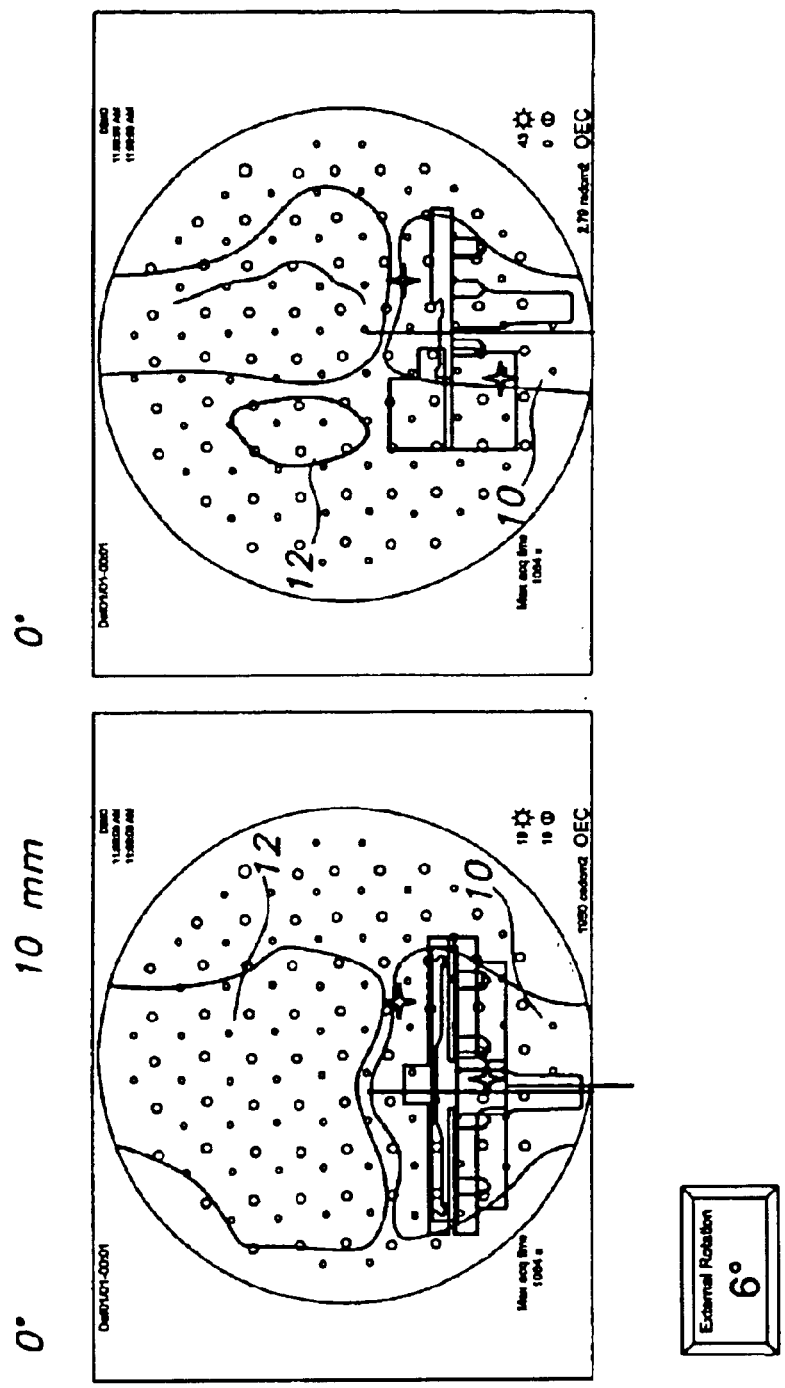
FIG. 38 is a screen face which shows a fluoroscopic image of bone in combination with computer generated images of axes and components in accordance with one embodiment of the present invention.
Figure 39:
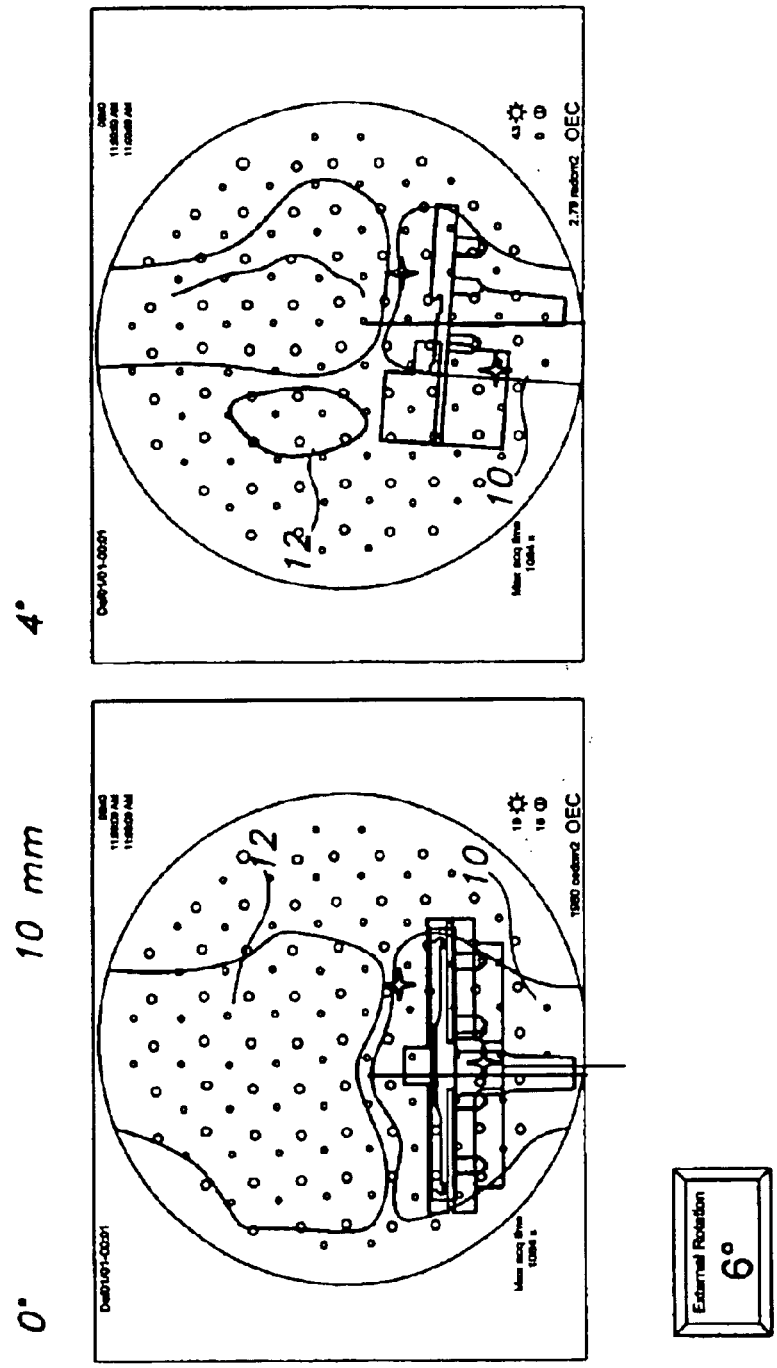
FIG. 39 is a screen face which shows a fluoroscopic image of bone in combination with computer generated images of axes and components in accordance with one embodiment of the present invention.
Figure 40:
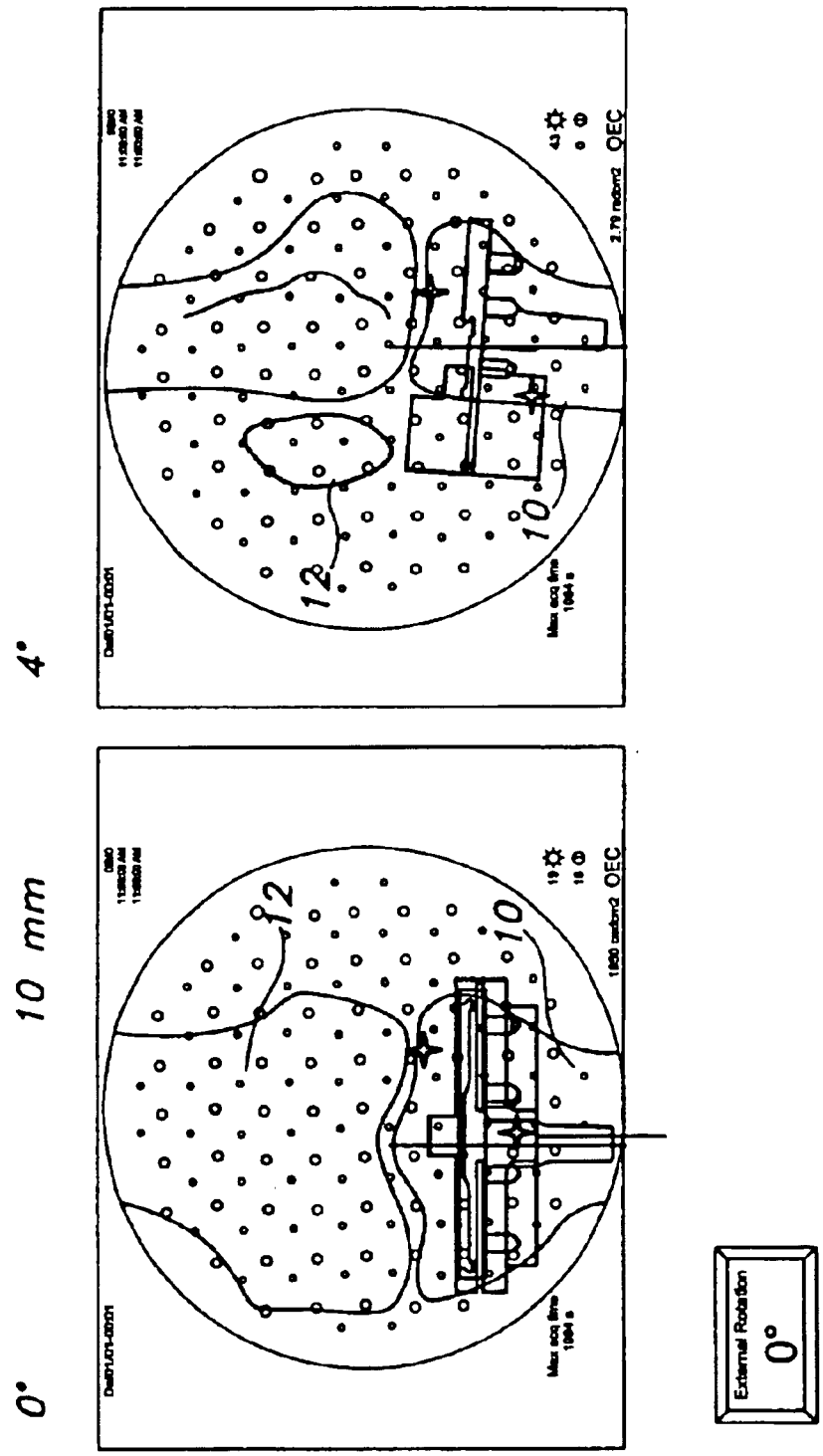
FIG. 40 is a screen face which shows a fluoroscopic image of bone in combination with computer generated images of axes and components in accordance with one embodiment of the present invention.

Once the extramedullary rod, intramedullary rod, other type of rod has been placed, instrumentation can be positioned as tracked in position and orientation by sensor 16 and displayed on screen face 24. Thus, a cutting block of the sort used to establish the condylar anterior cut, with its fiducial 14 attached, is introduced into the field and positioned on the rod. Because the cutting block corresponds to a particular implant product and can be adjusted and designated on screen to correspond to a particular implant size of that product, the computer 18 can generate and display a graphic of the cutting block and the femoral component overlain on the fluoroscopic image as shown in FIGS. 33–36. The surgeon can thus navigate and position the cutting block on screen using not only images of the cutting block on the bone, but also images of the corresponding femoral component which will be ultimately installed. The surgeon can thus adjust the positioning of the physical cutting block component, and secure it to the rod in order to resect the anterior of the condylar portion of the femur in order to optimally fit and position the ultimate femoral component being shown on the screen. FIG. 32 is another view of the cutting block of FIG. 31 being positioned. Other cutting blocks and other resections may be positioned and made similarly on the condylar component.

Figure 41:
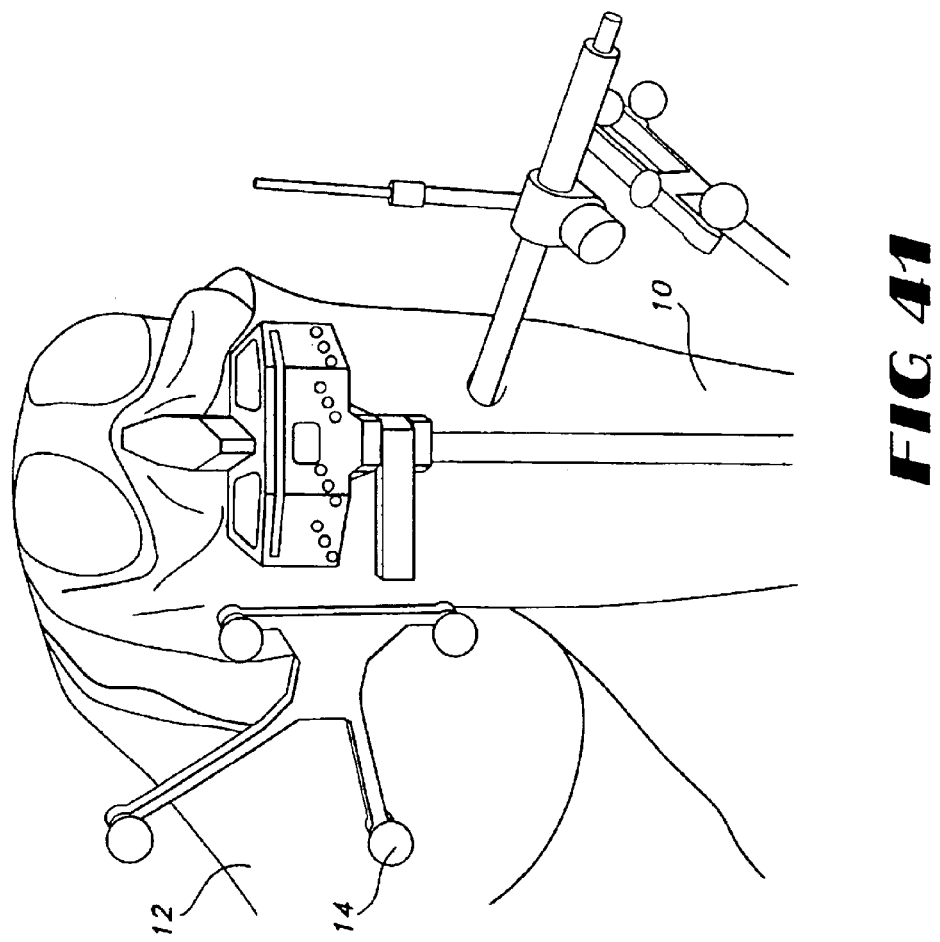
FIG. 41 is a view showing placement of a cutting block according to one embodiment of the present invention.
Figure 42:
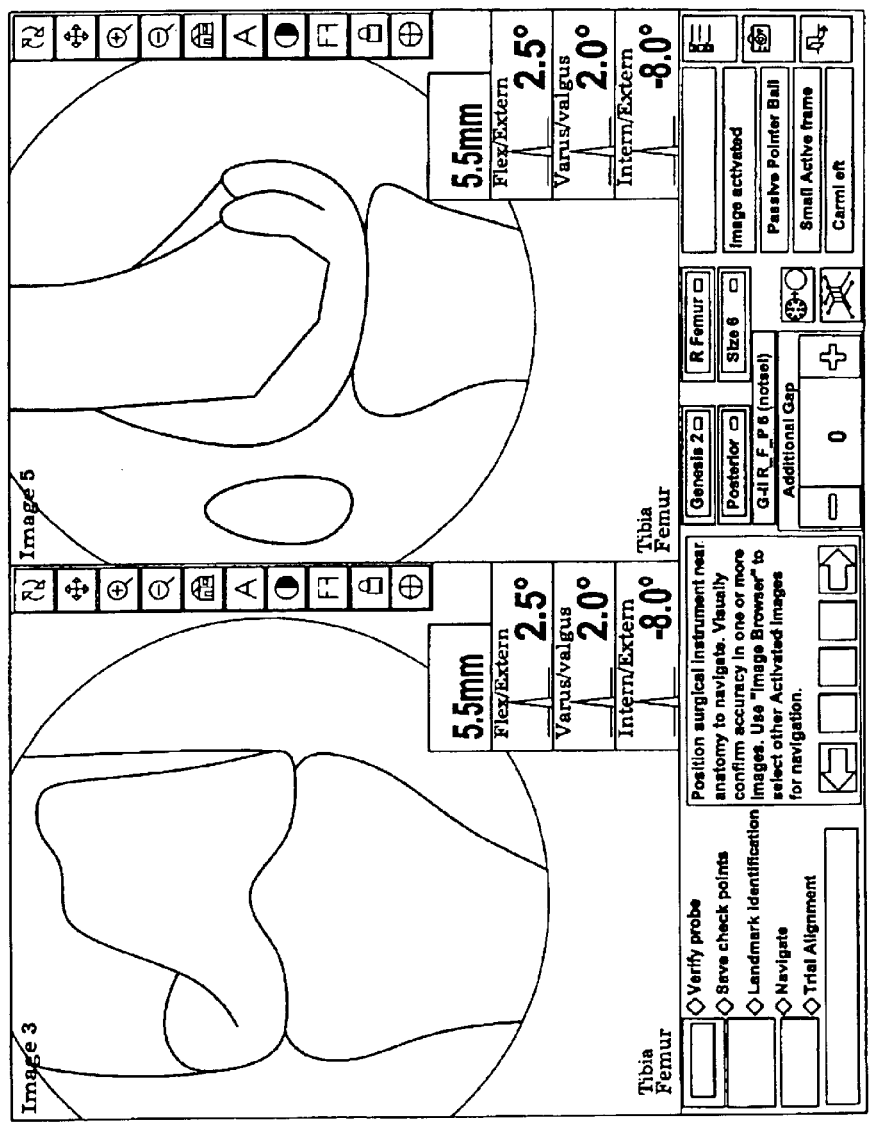
FIG. 42 is a screen face according to one embodiment of the present invention which may be used to assist in navigation and placement of instrumentation.
Figure 43:
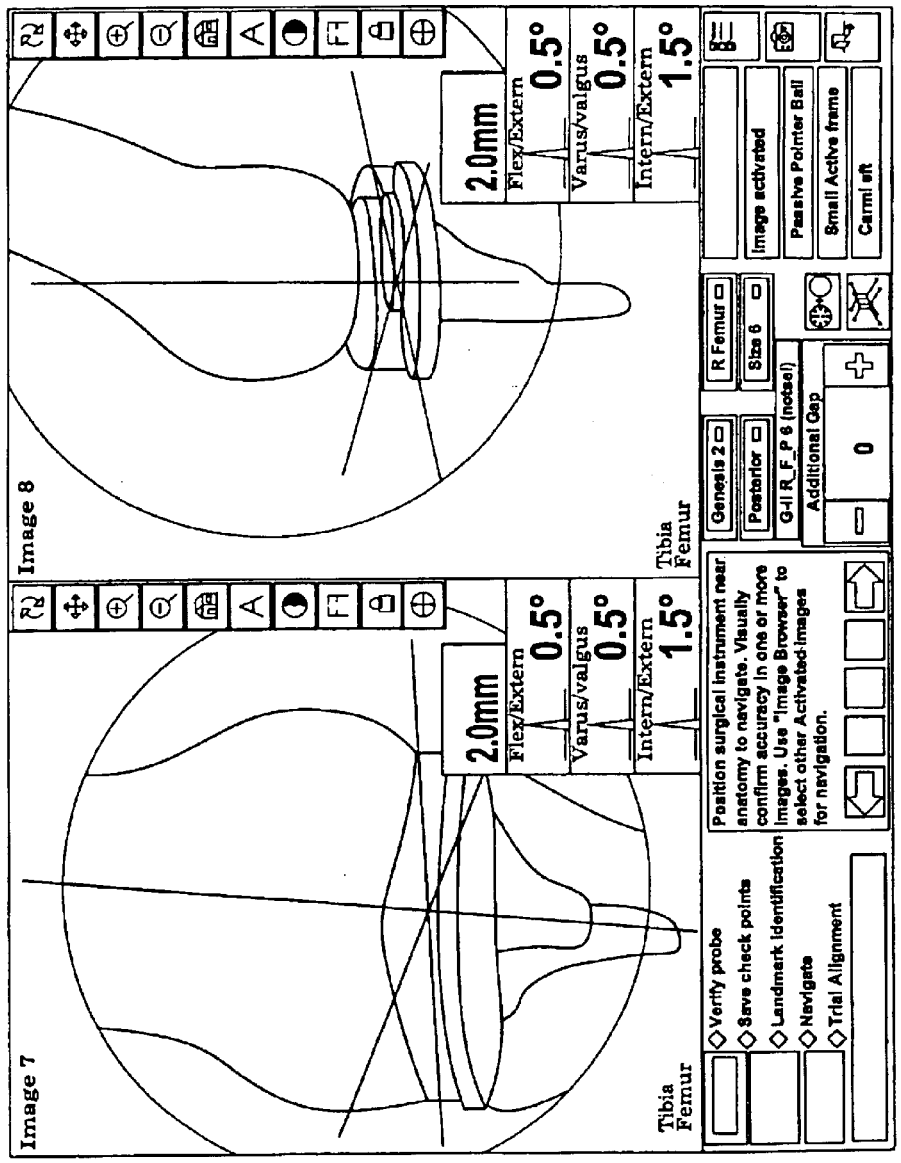
FIG. 43 is another screen face according to one embodiment of the present invention which may be used to assist in navigation and/or placement of instrumentation.
Figure 44:
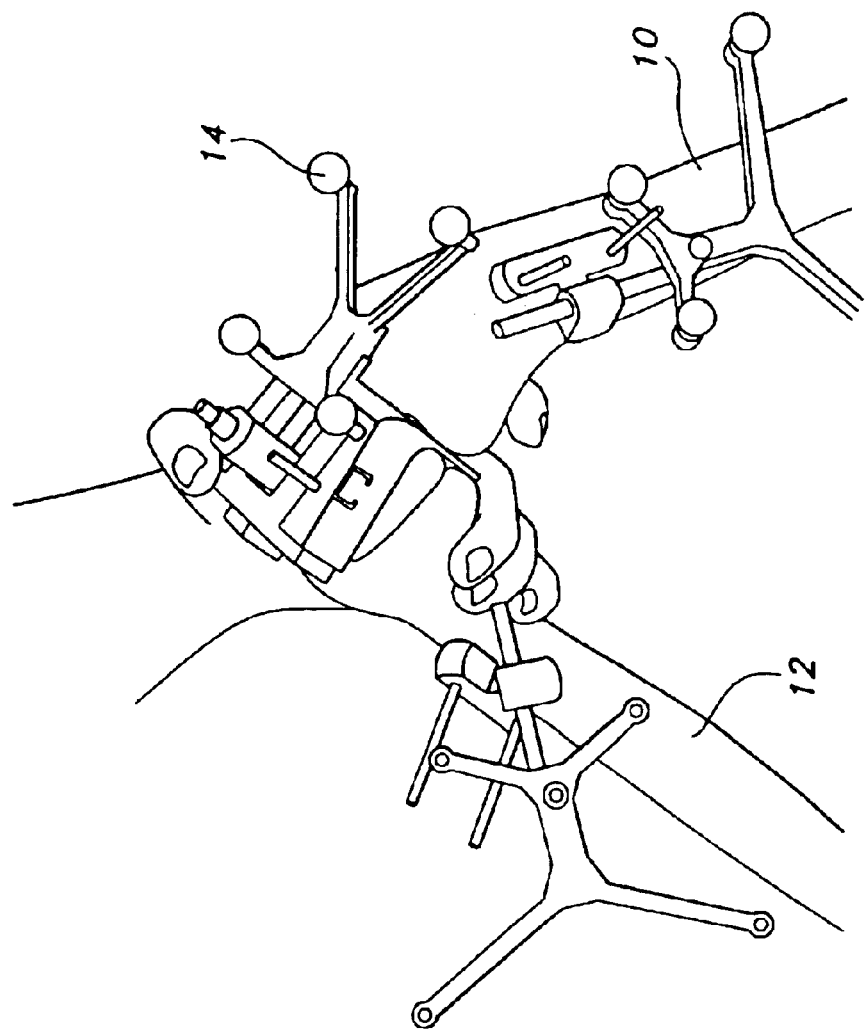
FIG. 44 is a view showing placement of an alignment guide according to one embodiment of the present invention.
Figure 45:
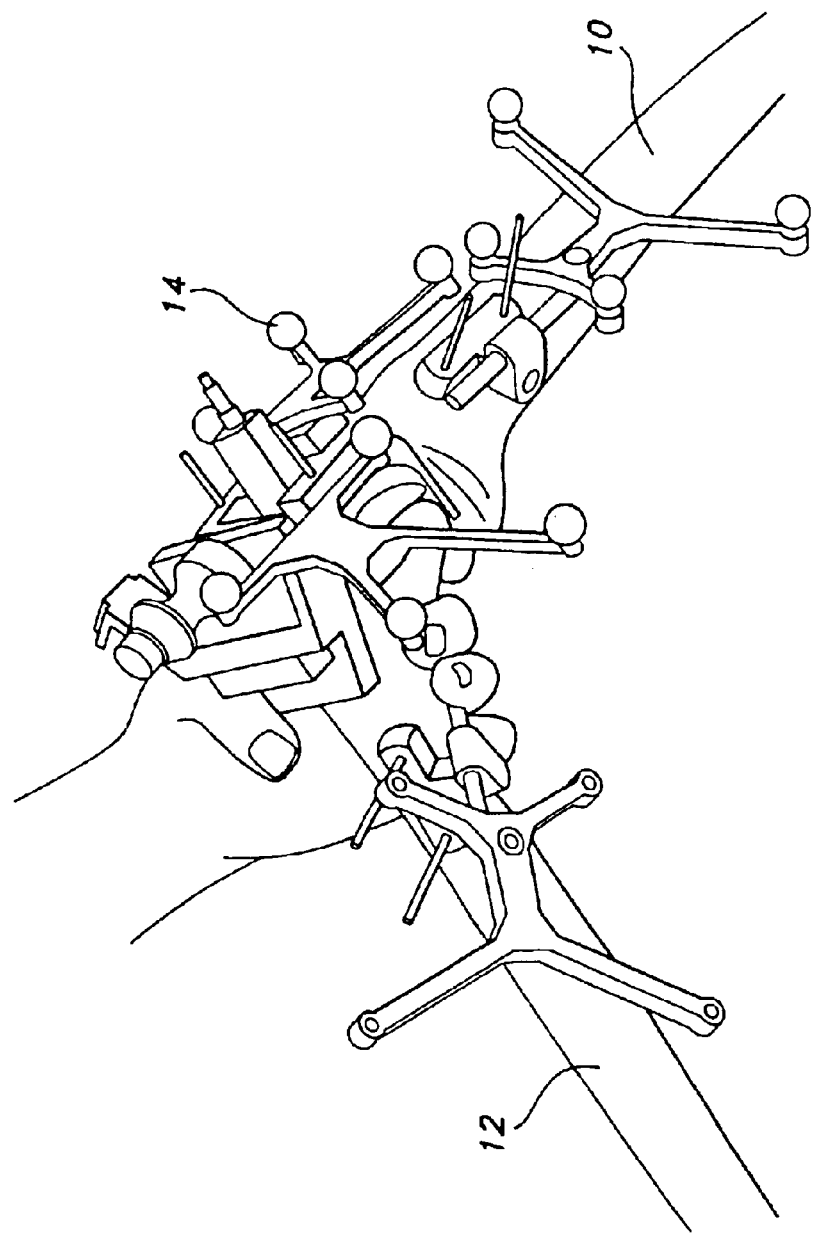
FIG. 45 is another view showing placement of a cutting block according to one embodiment of the present invention.
Figure 46:
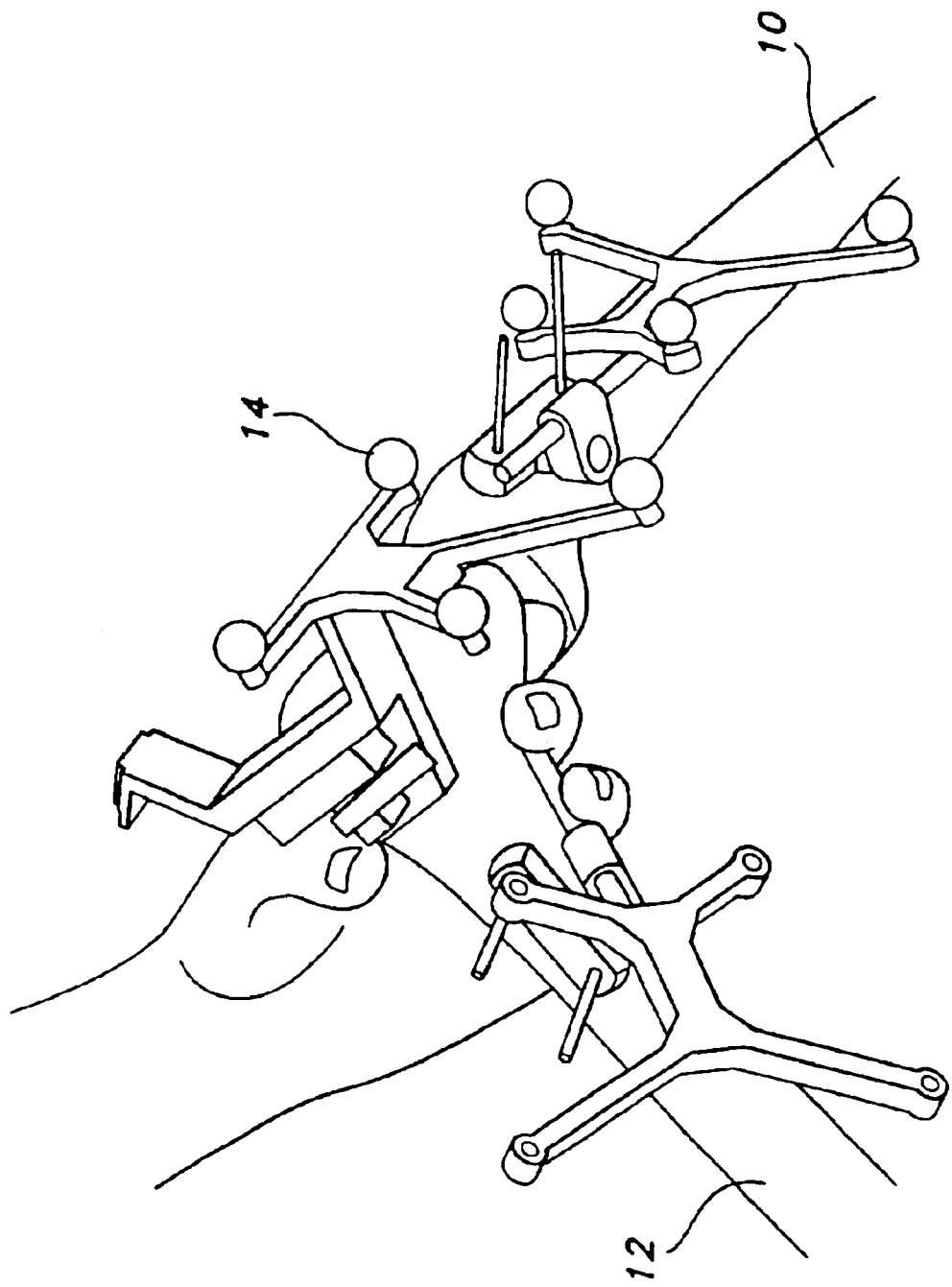
FIG. 46 is a view showing navigation and placement of the cutting block of FIG. 45.
Figure 47:
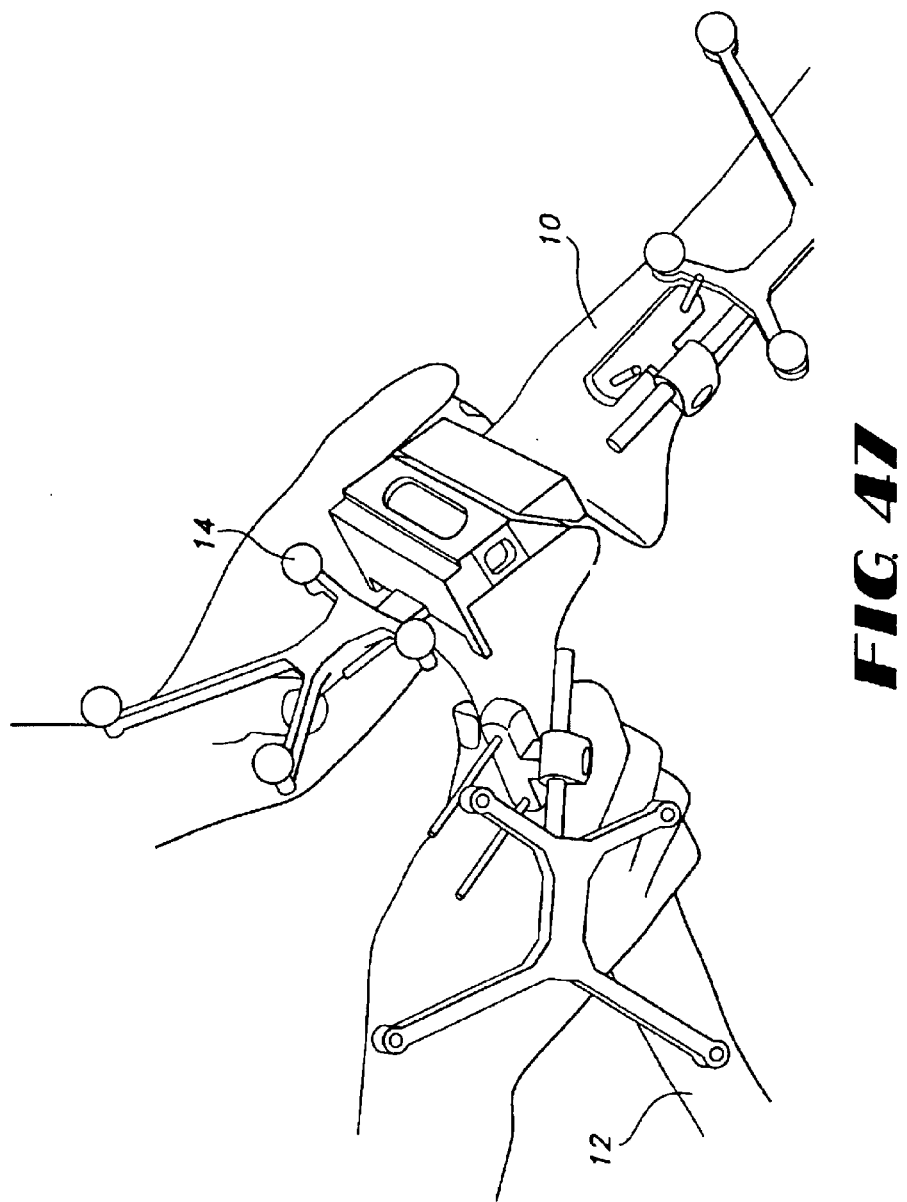
FIG. 47 is another view showing navigation and placement of a cutting block according to one embodiment of the present invention.
Figure 48:
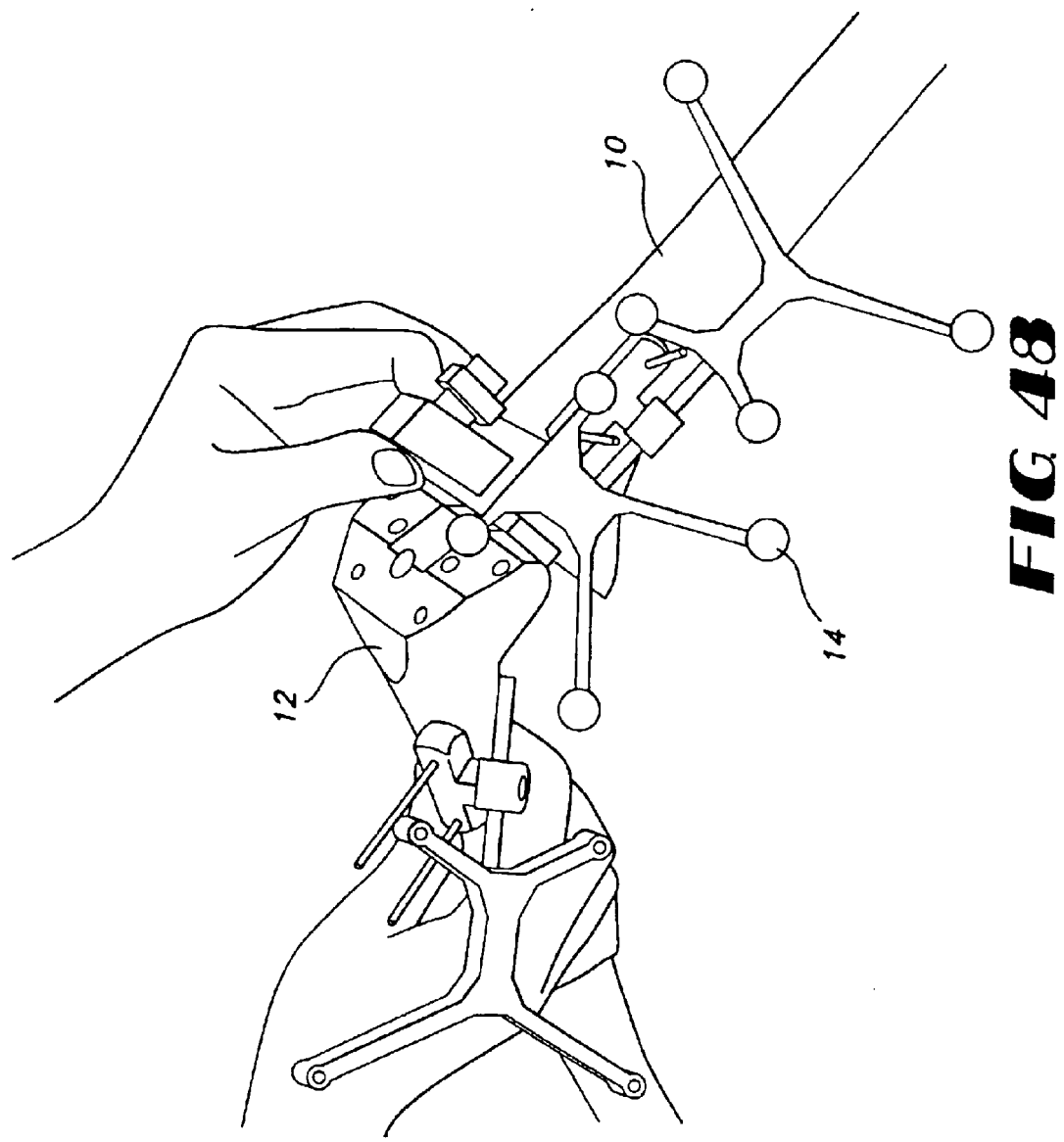
FIG. 48 is a view showing navigation and placement of a tibial cutting block according to one embodiment of the present invention.

In a similar fashion, instrumentation may be navigated and positioned on the proximal portion of the tibia 10 as shown in FIG. 41 and as tracked by sensor 16 and on screen by images of the cutting block and the implant component as shown in FIGS. 37–40. FIGS. 42 and 43 show other onscreen images generated during this bone modification process for purposes of navigation and positioning cutting blocks and other instrumentation for proper resection and other modification of femur and tibia in order to prepare for trial components and implant components according to systems and processes of the embodiment of the present invention shown in FIGS. 4–64.

FIGS. 44–48 also show instrumentation being positioned relative to femur 12 as tracked by the system for resection of the condylar component in order to receive a particular size of implant component. Various cutting blocks and their attached fiducials can be seen in these views.

Figure 49:
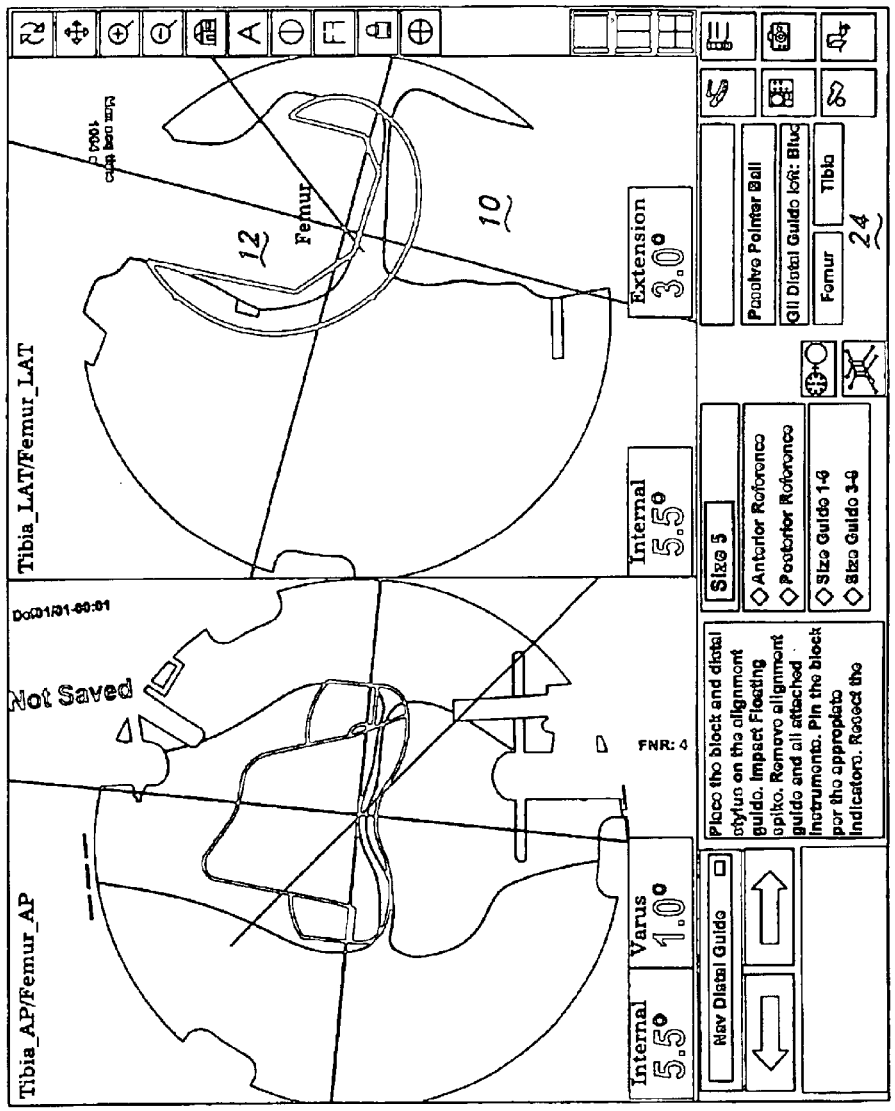
FIG. 49 is a screen face according to one embodiment of the present invention which may be used to assist in navigation and placement of instrumentation.
Figure 50:
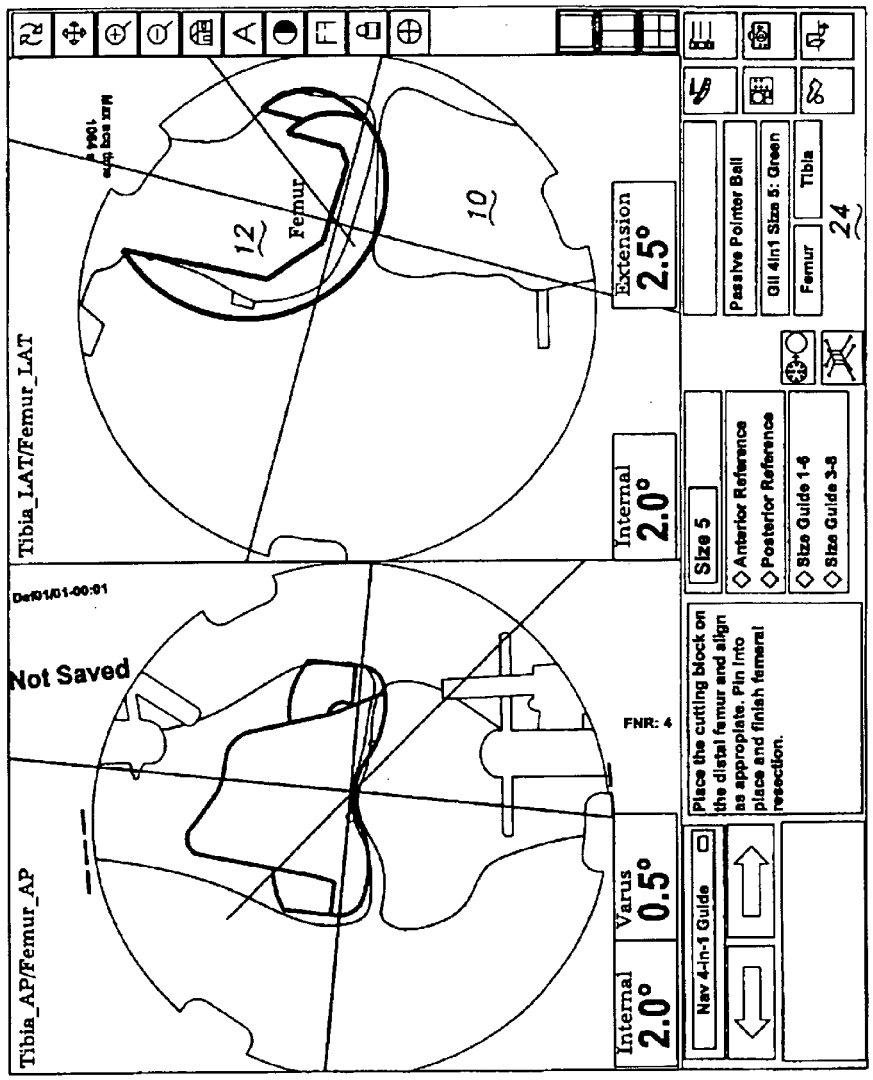
FIG. 50 is another screen face according to one embodiment of the present invention which may be used to assist in navigation and placement of instrumentation.

FIG. 49 shows a femoral component overlaid on the femur as instrumentation is being tracked and positioned in order for resection of bone properly and accurately to be accomplished. FIG. 50 is another navigational screen face showing a femoral component overlay as instrumentation is being positioned for resection of bone.

Figure 51:
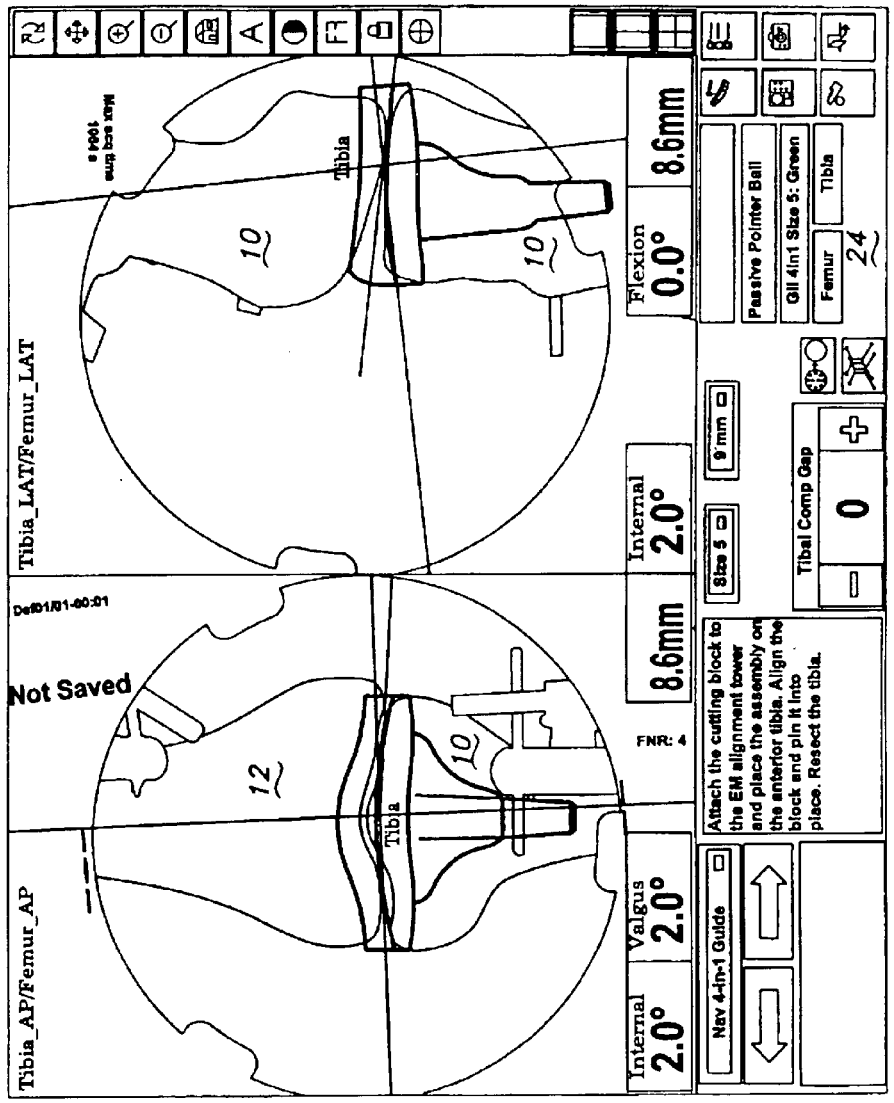
FIG. 51 is another screen face according to one embodiment of the present invention which may be used to assist in navigation and placement of instrumentation.

FIG. 51 is tibial component overlay information on a navigation screen as the cutting block for the tibial plateau is being positioned for bone resection.

Figure 52:
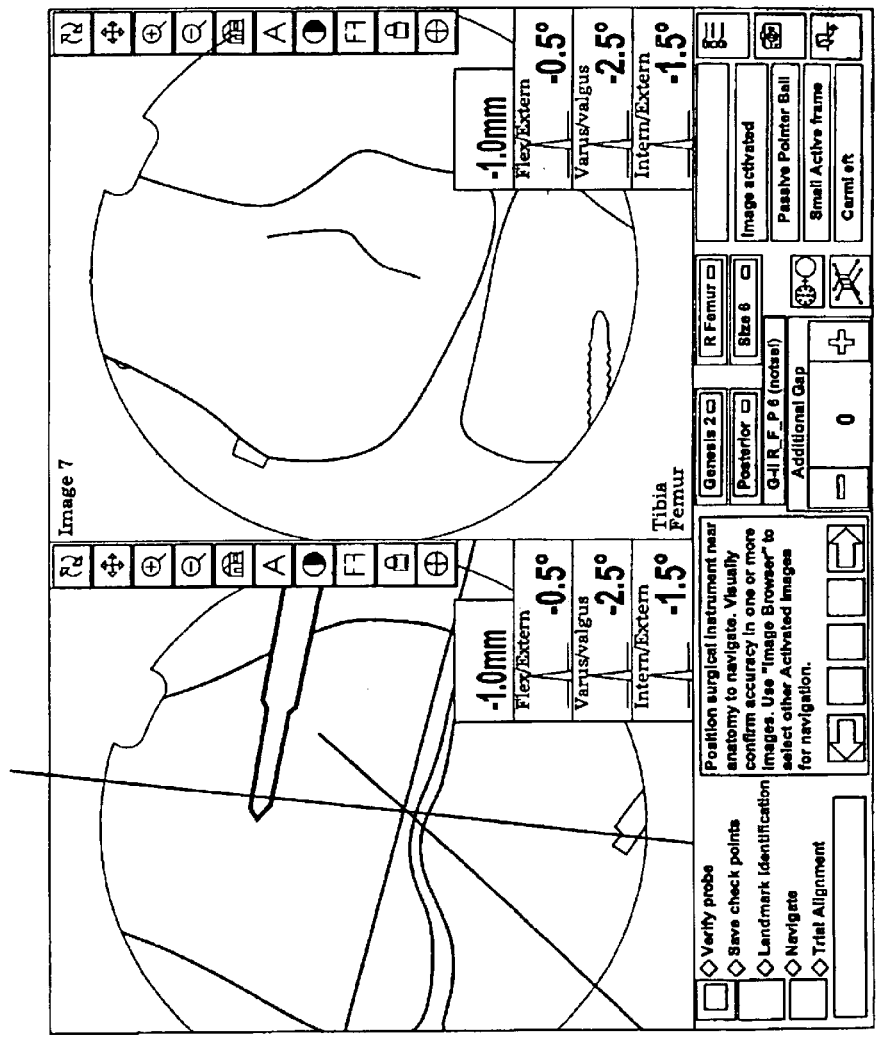
FIG. 52 is another screen face according to one embodiment of the present invention which may be used to assist in navigation and placement of instrumentation.
Figure 53:
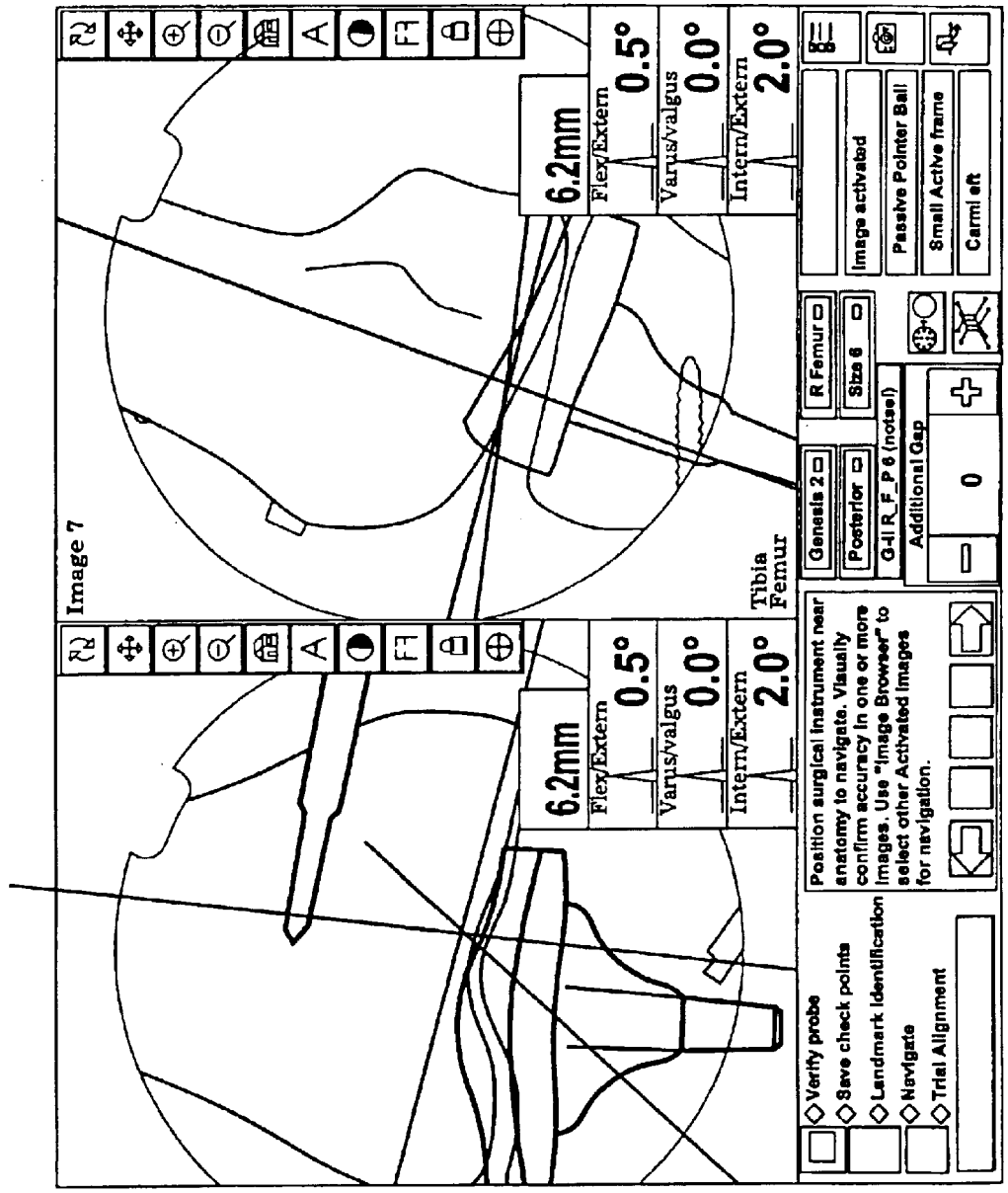
FIG. 53 is another screen face according to one embodiment of the present invention which may be used to assist in navigation and placement of instrumentation.
Figure 54:
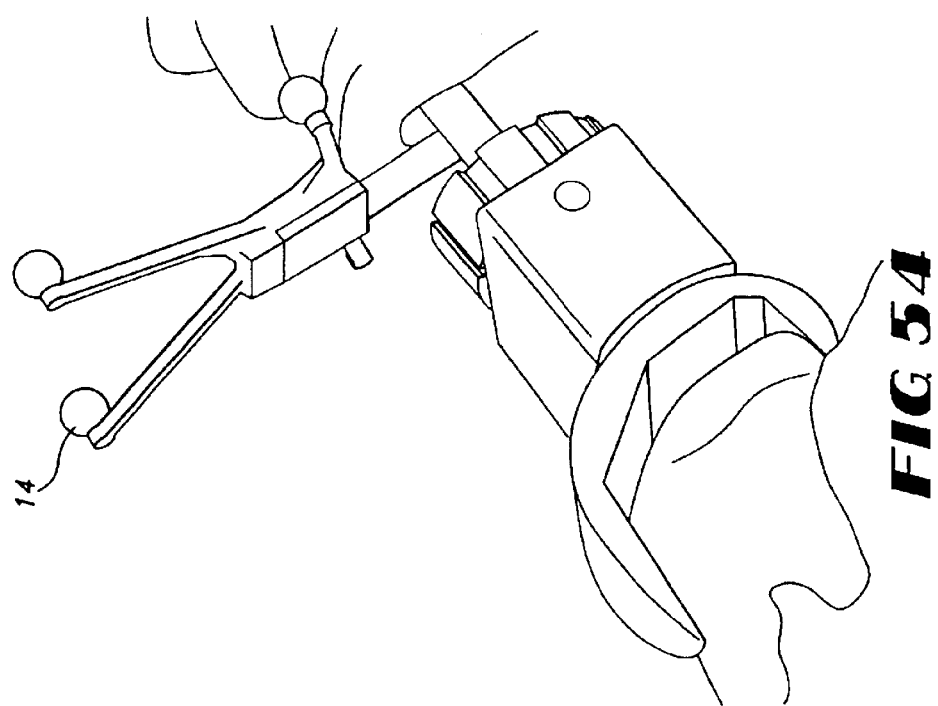
FIG. 54 is a view showing navigation and placement of a femoral component using an impactor to which a fiducial according to one embodiment of the present invention is attached.

FIGS. 52 and 53 show femoral component and tibial component overlays, respectively, according to certain position and orientation of cutting blocks/instrumentation as resectioning is being done. The surgeon can thus visualize where the implant components will be and can assess fit, and other things if desired, before resections are made.

Navigation, Placement and Assessment of Trials and Implants

Once resection and modification of bone has been accomplished, implant trials can then be installed and tracked by the system in a manner similar to navigating and positioning the instrumentation, as displayed on the screen 24. Thus, a femoral component trial, a tibial plateau trial, and a bearing plate trial may be placed as navigated on screen using computer generated overlays corresponding to the trials.

During the trial installation process, and also during the implant component installation process, instrument positioning process or at any other desired point in surgical or other operations according to the present invention, the system can transition or segue from tracking a component according to a first fiducial to tracking the component according to a second fiducial. Thus, as shown as FIG. 33, the trial femoral component is mounted on an impactor to which is attached a fiducial 14. The trial component is installed and positioned using the impactor. The computer 18 "knows" the position and orientation of the trial relative to the fiducial on the impactor (such as by prior registration of the component attached to the impactor) so that it can generate and display the image of the femoral component trial on screen 24 overlaid on the fluoroscopic image of the condylar component. At any desired point in time, before, during or after the trial component is properly placed on the condylar component of the femur to align with mechanical axis and according to proper orientation relative to other axes, the system can be instructed by foot pedal or otherwise to begin tracking the position of the trial component using the fiducial attached to the femur rather than the one attached to the impactor. According to the preferred embodiment, the sensor 16 "sees" at this point in time both the fiducials on the impactor and the femur 12 so that it already "knows" the position and orientation of the trial component relative to the fiducial on the impactor and is thus able to calculate and store for later use the position and orientation of the trial component relative to the femur 12 fiducial. Once this "handoff" happens, the impactor can be removed and the trial component tracked with the femur fiducial 14 as part of or moving in concert with the femur 12. Similar handoff procedures may be used in any other instance as desired in accordance with the present invention.

Figure 55:
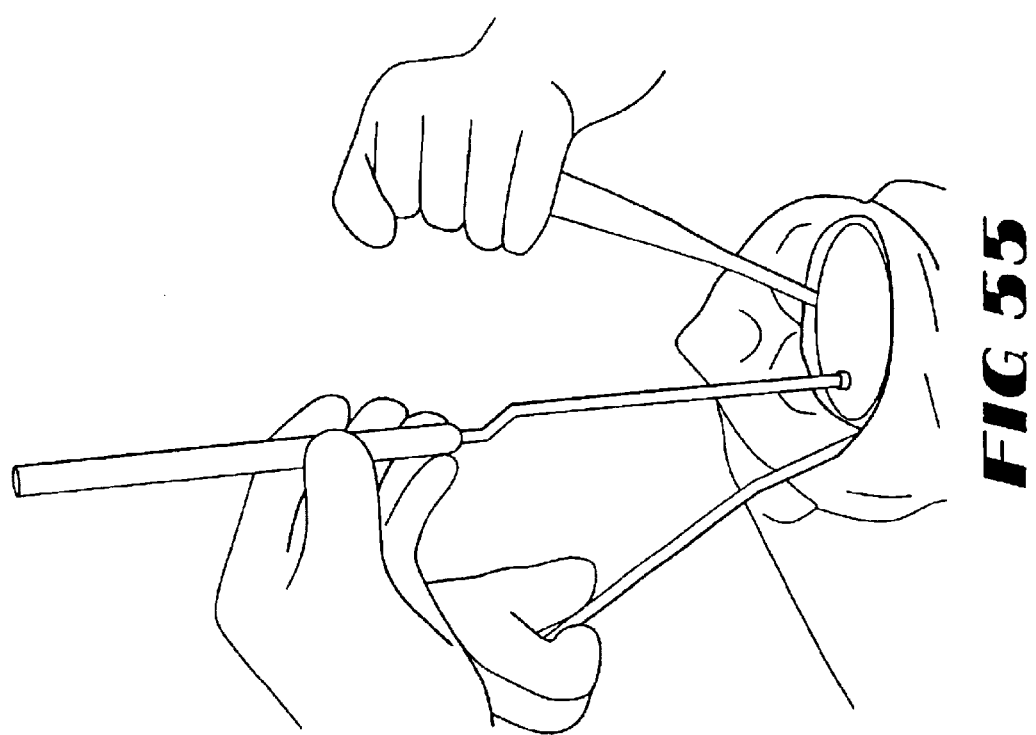
FIG. 55 is a view showing navigation and placement of a tibial trial component according to one embodiment of the present invention.

FIG. 55 shows the tibial plateau trial being tracked and installed in a manner similar to femoral component trial as discussed above. Alternatively, the tibial trial can be placed on the proximal tibia and then registered using the probe 26. Probe 26 is used to designate preferably at least three features on the tibial trial of known coordinates, such as bone spike holes. As the probe is placed onto each feature, the system is prompted to save that coordinate position so that the system can match the tibial trial's feature's coordinates to the saved coordinates. The system then tracks the tibial trial relative to the tibial anatomical reference frame.

Once the trial components are installed, the surgeon can assess alignment and stability of the components and the joint. During such assessment, in trial reduction, the computer can display on monitor 24 the relative motion between the trial components to allow the surgeon to make soft tissue releases and changes in order to improve the kinematics of the knee. The system can also apply rules and/or intelligence to make suggestions based on the information such as what soft tissue releases to make if the surgeon desires. The system can also display how the soft tissue releases are to be made.

Figure 56:
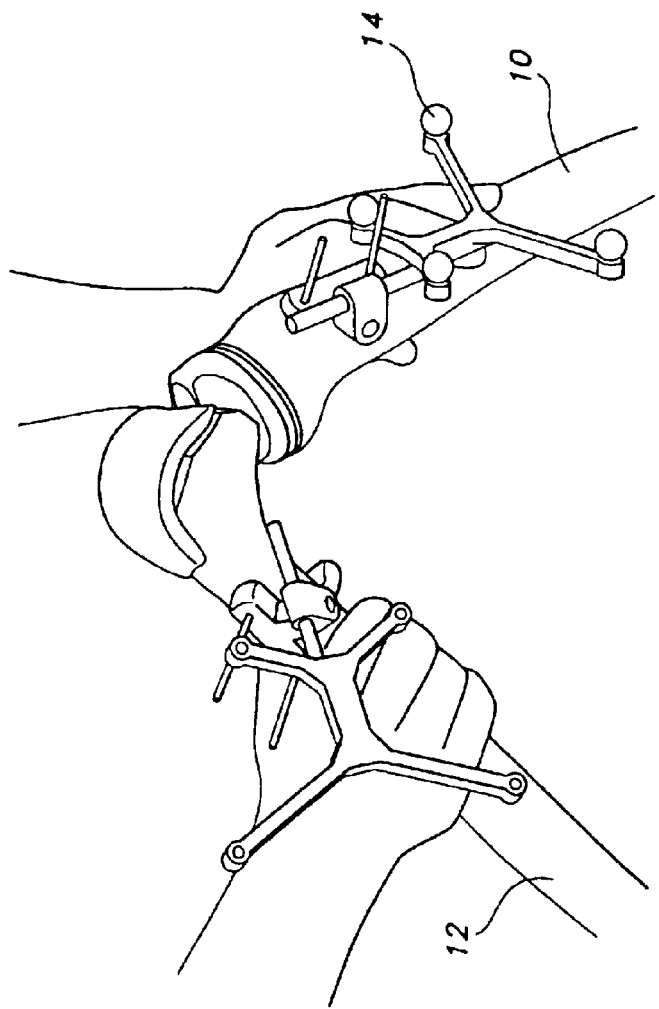
FIG. 56 is a view showing articulation of trial components during trial reduction according to one embodiment of the present invention.
Figure 57:
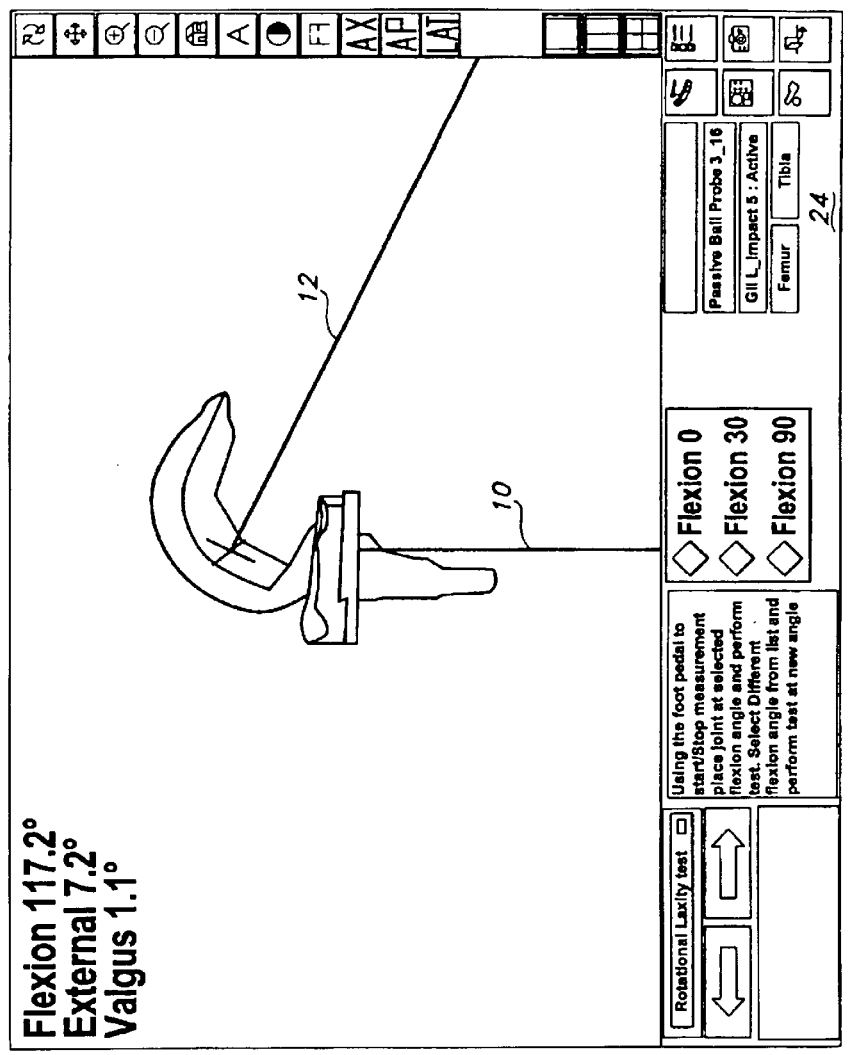
FIG. 57 is a screen face according to one embodiment of the present invention which may be used to assist in assessing joint function.
Figure 53:
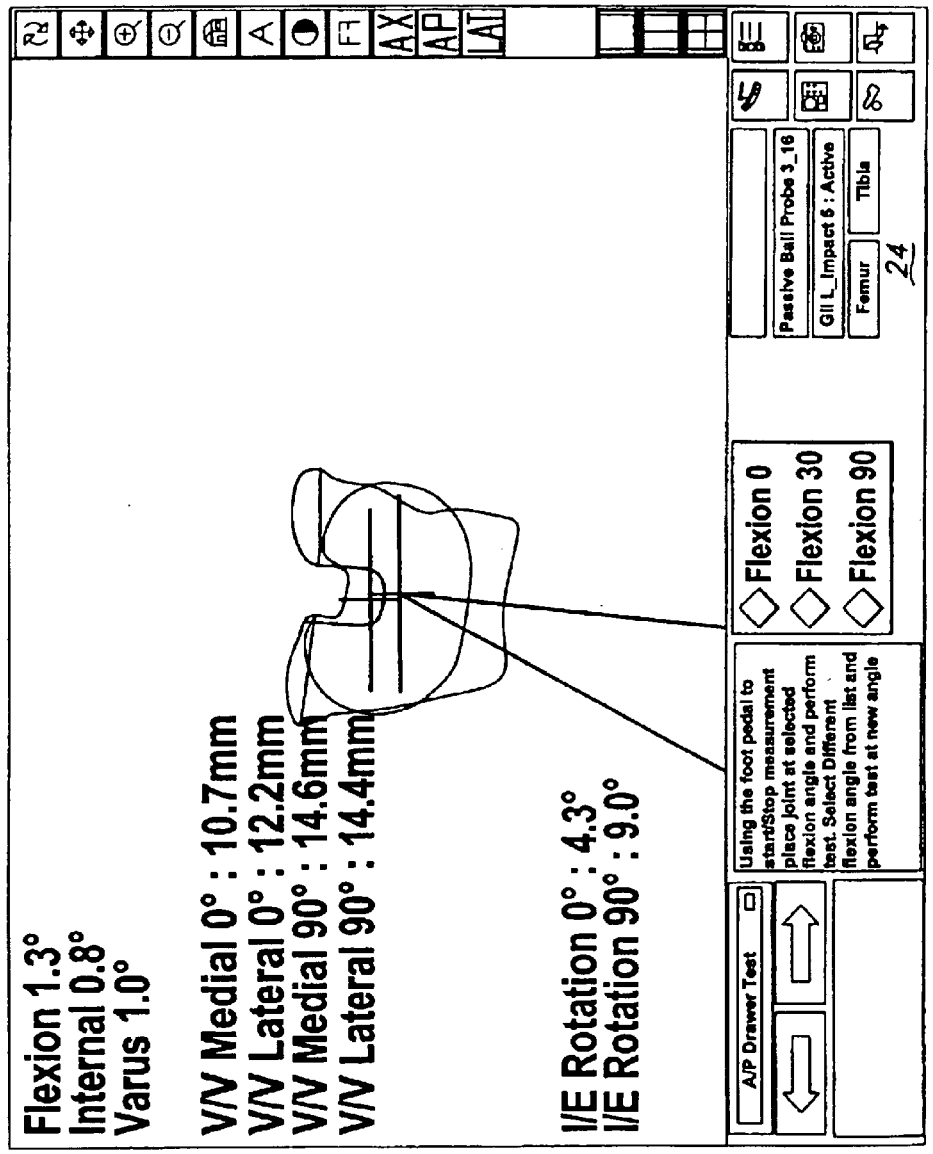
Figure 59:
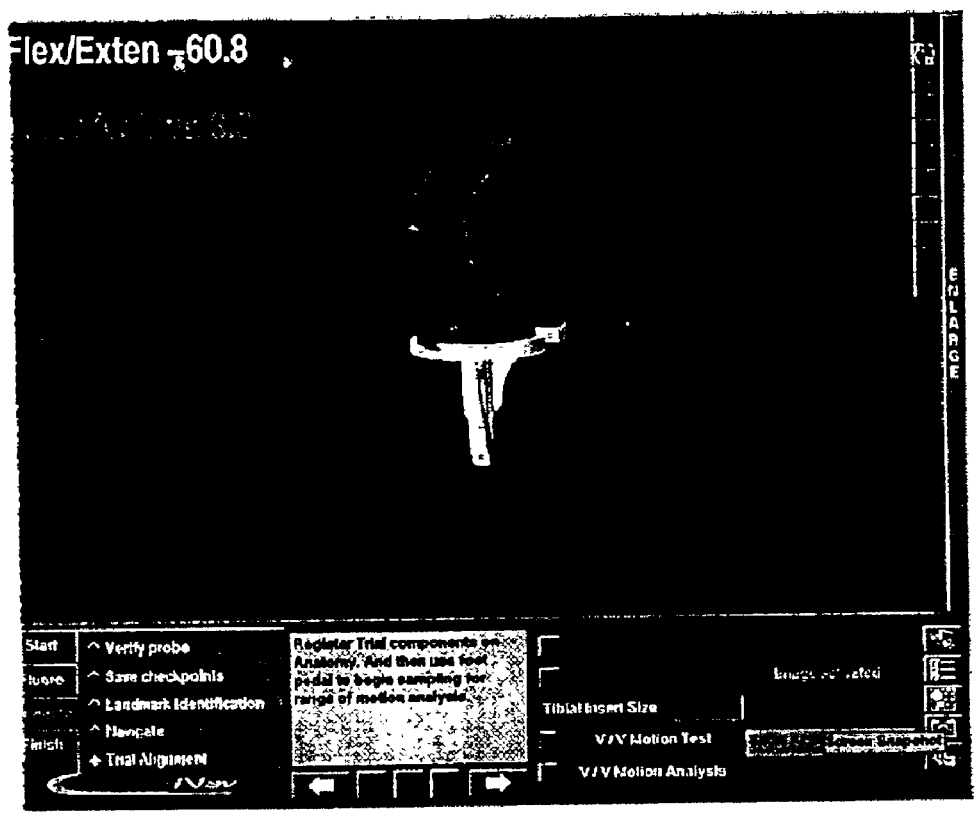
FIG. 59 is a screen face according to one embodiment of the present invention which may be used to assist in assessing joint function.
Figure 60:
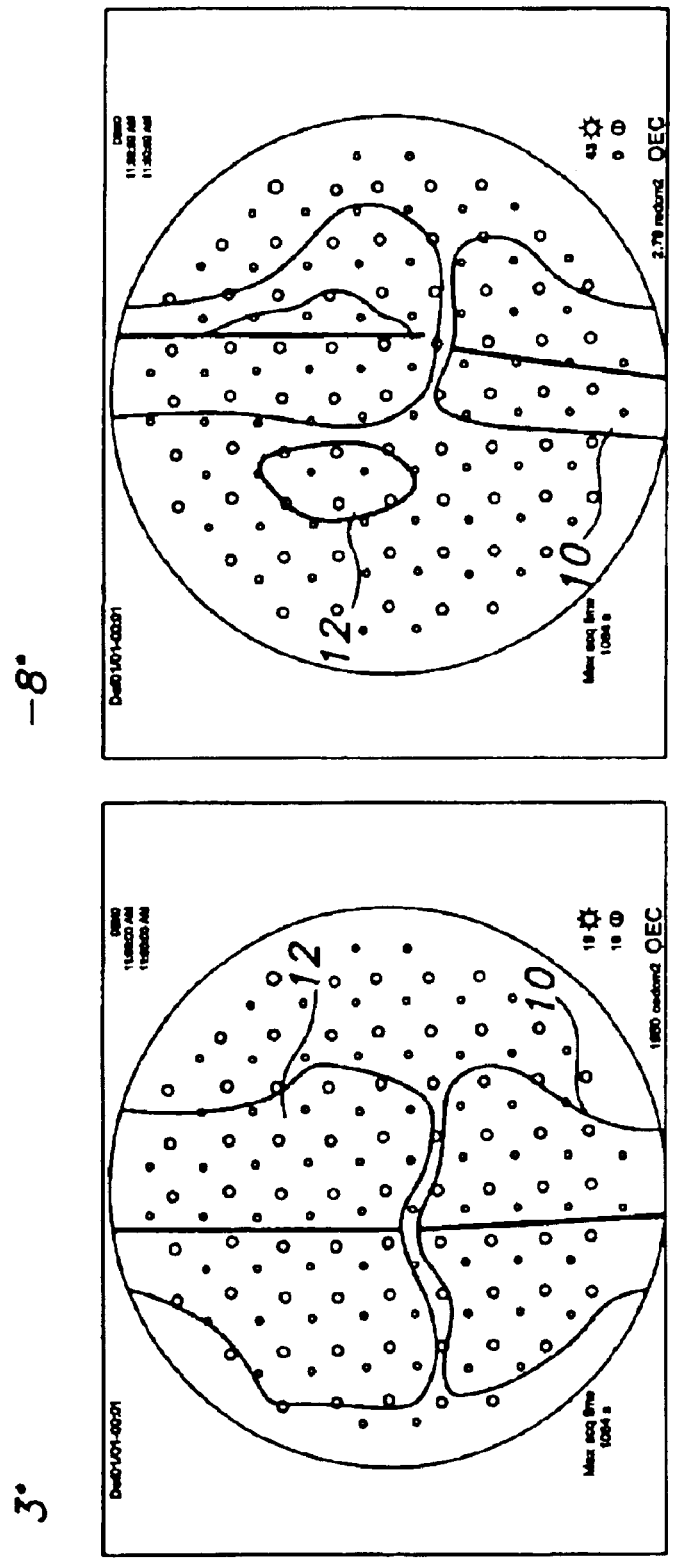
FIG. 60 is a screen face according to one embodiment of the present invention which contains images and textural suggestions for assisting in assessing performance and making adjustments to improve performance of a joint in accordance with one aspect of the invention.
Figure 61:
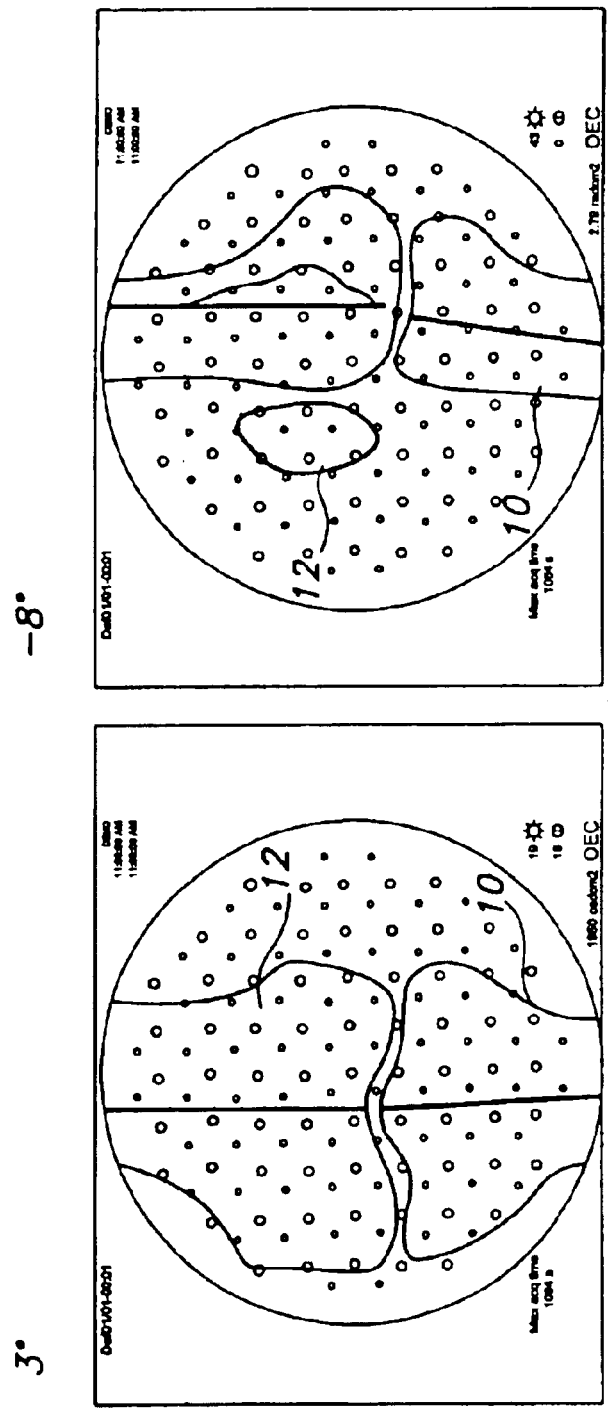
FIG. 61 is a screen face according to one embodiment of the present invention which contains images and textural suggestions for assisting in assessing performance and making adjustments to improve performance of a joint in accordance with one aspect of the invention.
Figure 62:
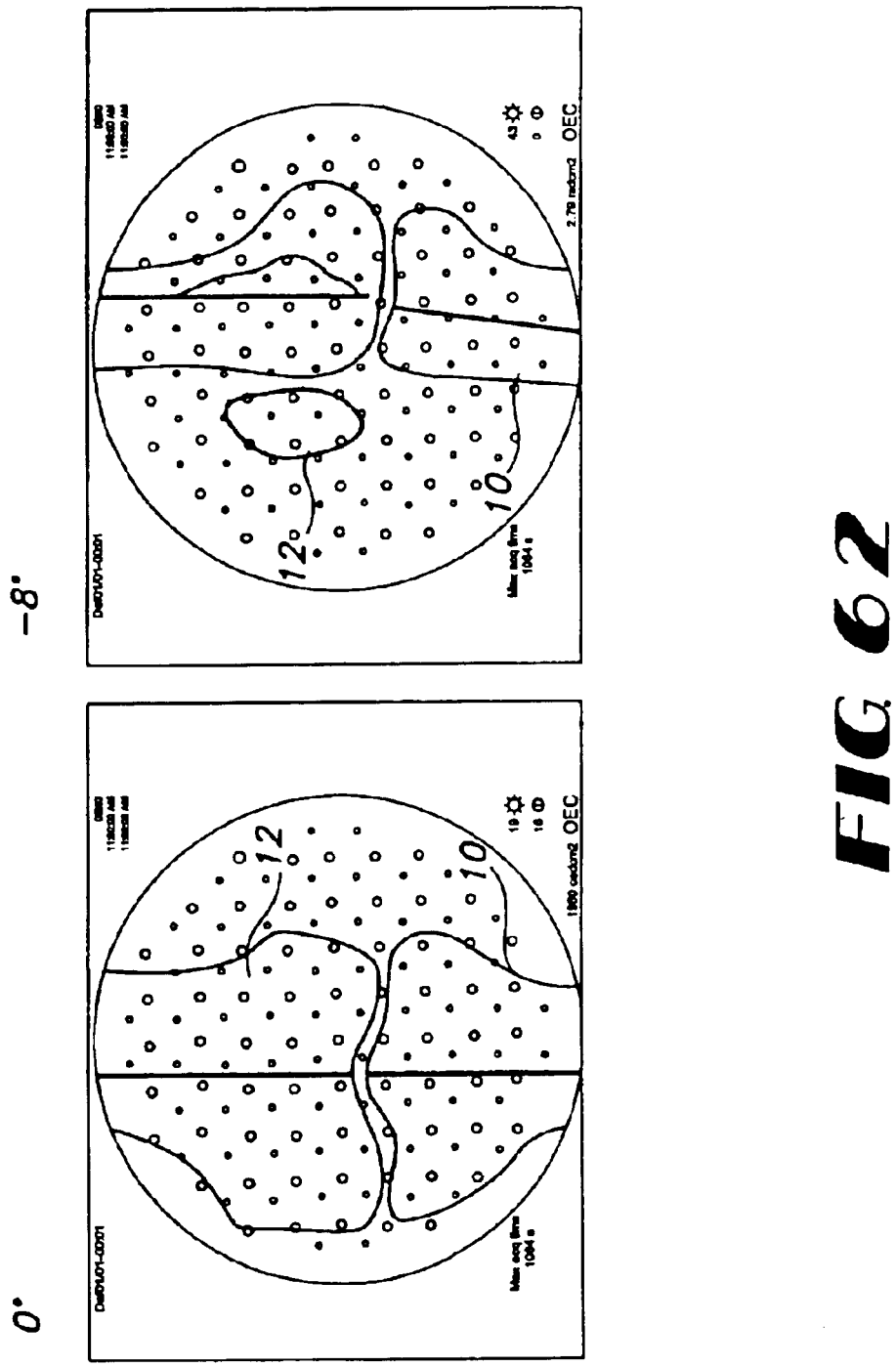
FIG. 62 is a screen face according to one embodiment of the present invention which contains images and textural suggestions for assisting in assessing performance and making adjustments to improve performance of a joint in accordance with one aspect of the invention.
Figure 63:
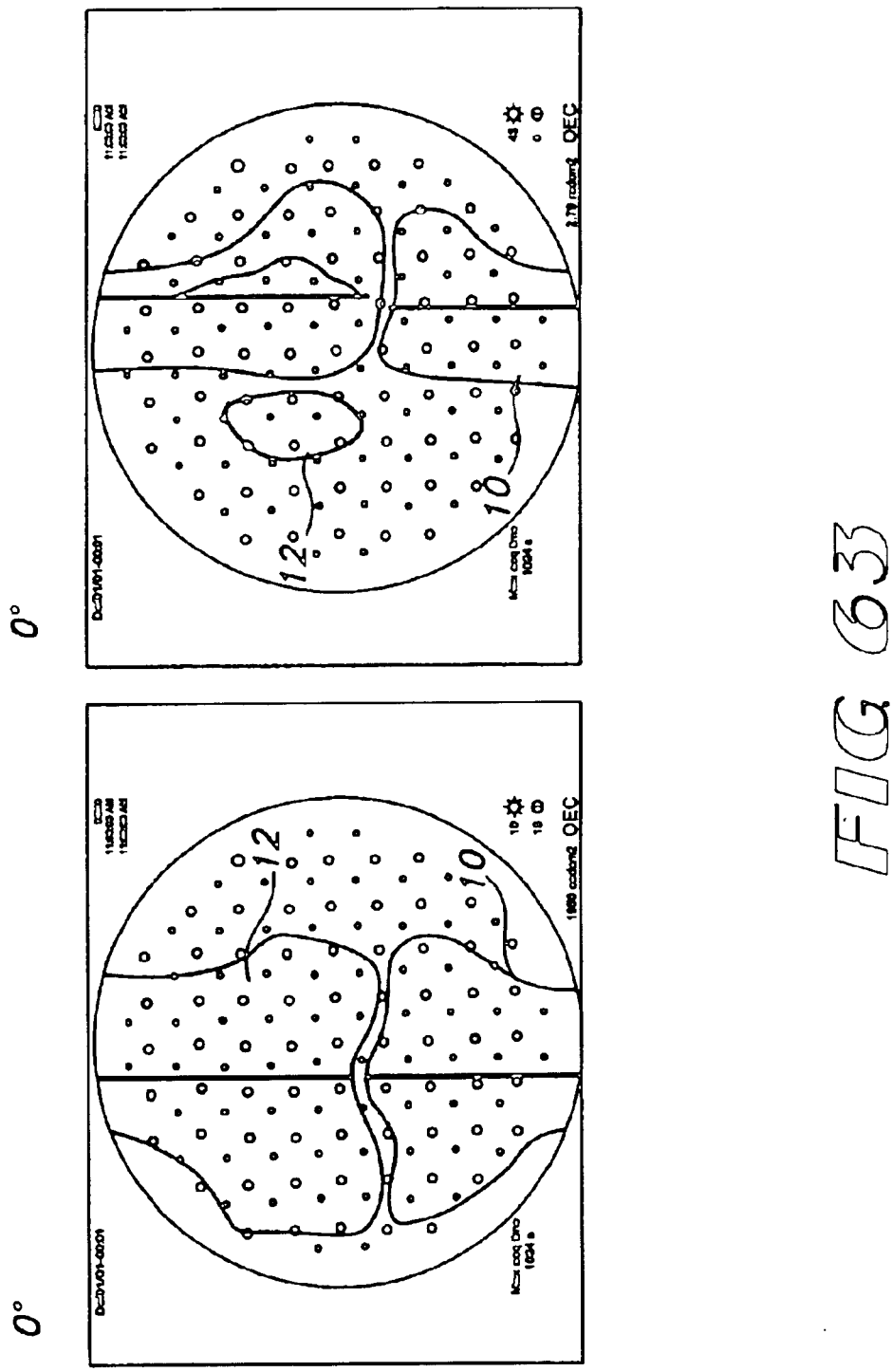
FIG. 63 is a screen face according to one embodiment of the present invention which contains images and textural suggestions for assisting in assessing performance and making adjustments to improve performance of a joint in accordance with one aspect of the invention.

FIG. 56 shows the surgeon articulating the knee as he monitors the screen which is presenting images such as those shown in FIGS. 57–59 which not only show movement of the trial components relative to each other, but also orientation, flexion, and varus/valgus. During this assessment, the surgeon may conduct certain assessment processes such as external/internal rotation or rotary laxity testing, varus/valgus tests, and anterior-posterior drawer at 0 and 90 degrees and mid range. Thus, in the AP drawer test, the surgeon can position the tibia at the first location and press the foot pedal. He then positions the tibia at the second location and once again presses the foot pedal so that the computer has registered and stored two locations in order to calculate and display the drawer and whether it is acceptable for the patient and the product involved. If not, the computer can apply rules in order to generate and display suggestions for releasing ligaments or other tissue, or using other component sizes or types, such as shown, for example, in FIGS. 60–63. Once the proper tissue releases have been made, if necessary, and alignment and stability are acceptable as noted quantitatively on screen about all axes, the trial components may be removed and actual components navigated, installed, and assessed in performance in a manner similar to that in which the trial components were navigated, installed, and assessed.

FIG. 64 is another computer generated 3-dimensional image of the trial components as tracked by the system during trialing.

At the end of the case, all alignment information can be saved for the patient file. This is of great assistance to the surgeon due to the fact that the outcome of implant positioning can be seen before any resectioning has been done on the bone. The system is also capable of tracking the patella and resulting placement of cutting guides and the patellar trial position. The system then tracks alignment of the patella with the patellar femoral groove and will give feedback on issues, such as, patellar tilt.

The tracking and image information provided by systems and processes according to the present invention facilitate telemedical techniques, because they provide useful images for distribution to distant geographic locations where expert surgical or medical specialists may collaborate during surgery. Thus, systems and processes according to the present invention can be used in connection with computing functionality 18 which is networked or otherwise in communication with computing functionality in other locations, whether by PSTN, information exchange infrastructures such as packet switched networks including the Internet, or as otherwise desire. Such remote imaging may occur on computers, wireless devices, videoconferencing devices or in any other mode or on any other platform which is now or may in the future be capable of rending images or parts of them produced in accordance with the present invention. Parallel communication links such as switched or unswitched telephone call connections may also accompany or form part of such telemedical techniques. Distant databases such as online catalogs of implant suppliers or prosthetics buyers or distributors may form part of or be networked with functionality 18 to give the surgeon in real time access to additional options for implants which could be procured and used during the surgical operation.

What is claimed is:

1. A process for performing total knee arthroplasty surgical operations on portions of a knee joint comprising:
   (a) obtaining data corresponding to the structure of a body part forming a portion of said joint with a locator, wherein the body part and the locator are each attached to a fiducial capable of being tracked by at least one position sensor;
   (b) registering a total knee arthroplasty trial component attached at least indirectly to a fiducial capable of being tracked by at least one position sensor;
   (c) using a computer which receives signals from the at least one sensor, tracking position and orientation of the trial component relative to the body part; and
   (d) generating and displaying on a monitor associated with the computer a visual image of the trial component properly positioned and oriented relative to the body part.

2. A process for performing total knee arthroplasty surgical operations on portions of a knee joint, comprising:
   (a) obtaining data corresponding to structure of a body part forming a portion of said joint with a locator, wherein the body part and part of the locator are each attached to a fiducial capable of being tracked by at least one position sensor;
   (b) registering a total knee arthroplasty surgical instrument attached to a fiducial capable of being tracked by at least one position sensor;
   (c) using a computer which receives signals from the at least one sensor, tracking position and orientation of the total knee arthroplasty surgical instrument relative to the body part;
   (d) generating and displaying on a monitor associated with the computer a visual image of the total knee arthroplasty surgical instrument properly positioned and oriented relative to the body part;
   (e) navigating the total knee arthroplasty surgical instrument relative to the body part and attaching the total knee arthroplasty surgical instrument to the body part according to the image;
   (f) modifying the body part using the total knee arthroplasty surgical instrument attached to the body part; and (g) assessing performance of the joint using images displayed on said monitor.

3. The process of claim 2, further comprising registering a body part by intraoperatively designating at least one point on the body part with a probe, wherein the probe is attached to a fiducial capable of being tracked by said at least one position sensor.

4. The process of claim 2, wherein the body part comprises one of a femur, a tibia and a patella.

5. The process of claim 2, wherein the locator comprises one of a C-arm fluoroscope, a CT scanner, MRI equipment, ultrasound equipment, laser scanning equipment and a probe.

6. The process of claim 2, wherein the fiducials comprise one of active fiducials, passive fiducials and hybrid active/passive fiducials.

7. The process of claim 2, wherein the position tracking sensors comprise one of infrared sensors, electromagnetic sensors, electrostatic sensors, light sensors, sound sensors, and radiofrequency sensors.

8. The process of claim 2, wherein the total knee arthroplasty surgical instrument comprises a rod and a cutting block.

9. A process for performing total knee arthroplasty surgical operations on portions of a knee joint comprising:
   (a) obtaining data corresponding to structure of a body part forming a portion of said joint with a locator, wherein the body part and the locator are each attached to a fiducial capable of being tracked by at least one position sensor;
   (b) registering a total knee arthroplasty surgical instrument attached to a fiducial capable of being tracked by at least one position sensor;
   (c) using a computer which receives signals from the at least one sensor, tracking position and orientation of the total knee arthroplasty surgical instrument relative to the body part;
   (d) generating and displaying on a monitor associated with the computer a visual image of the total knee arthroplasty surgical instrument properly positioned and oriented relative to the body part;
   (e) navigating the total knee arthroplasty surgical instrument relative to the body part and attaching the total knee arthroplasty surgical instrument to the body part according to the image;
   (f) modifying the body part using the total knee arthroplasty surgical instrument attached to the body part;
   (g) removing the total knee arthroplasty surgical instrument from the body part;
   (h) registering a trial component attached to a fiducial capable of being tracked by at least one position sensor;
   (i) tracking position and orientation of the trial component relative to the body part;
   (j) generating and displaying on the monitor a visual image of the trial component properly positioned and oriented relative to the body part;
   (k) navigating and installing the trial component on the body part according to the image; and
   (l) assessing performance of the knee joint using images displayed on the monitor.

10. The process of claim 9, further comprising:
   (a) discontinuing tracking of the trial component using the fiducial attached to the trial component; and
   (b) initiating tracking of the trial component using the fiducial attached to the body part on which the trial component is installed.

11. The process of claim 9, wherein the body part comprises one of a femur, a tibia and a patella.

12. The process of claim 9, wherein the locator comprises one of a C-arm fluoroscope, a CT scanner, MRI equipment, ultrasound equipment, laser scanning equipment and a probe.

13. The process of claim 9, wherein the fiducials comprise one of active fiducials, passive fiducials and hybrid active/passive fiducials.

14. The process of claim 9, wherein the position/orientation tracking sensors comprise at least one of infrared sensors, electromagnetic sensors, electrostatic sensors, light sensors, sound sensors, and radiofrequency sensors.

15. The process of claim 9, wherein the trial component comprises a femoral component.

16. The process of claim 9, further comprising:
   (a) performing soft tissue balancing tests while the computer continues to track the fiducials;
   (b) using data generated by the computer, including information related to at least one of release points and amounts, to assess alignment and stability of the trial component and the knee joint; and
   (c) releasing soft tissue to adjust alignment and stability of the knee joint.

17. A process for performing total knee arthroplasty surgical operations on portions of a knee joint comprising:
   (a) obtaining data corresponding to structure of a body part forming a portion of said joint with a locator, wherein the body part and the locator are each attached to a fiducial capable of being tracked by at least one position sensor;
   (b) registering a total knee arthroplasty implant trial component attached at least indirectly to a fiducial capable of being tracked by at least one position sensor;
   (c) using a computer which receives signals from the at least one sensor, tracking position and orientation of the trial component relative to the body part;
   (d) generating and displaying on a monitor associated with the computer a visual image of the trial component properly positioned and oriented relative to the body part;
   (e) navigating the trial component relative to the body part and attaching the trial component to the body part according to the image;
   (f) performing soft tissue balancing tests while the computer continues to track the fiducials;
   (g) using data generated by the computer to assess alignment and stability of the joint with the trial component attached; and
   (h) releasing soft tissue to adjust alignment and stability.

18. A process for performing total knee arthroplasty surgical operations on portions of a knee joint comprising:
   (a) obtaining data corresponding to structure of a body part forming a portion of said joint with a locator, wherein the body part and the locator are each attached to a fiducial capable of being tracked by at least one position sensor;
   (b) registering a total knee arthroplasty implant component attached at least indirectly to a fiducial capable of being tracked by at least one position sensor;
   (c) using a computer which receives signals from the at least one position sensor, tracking position and orientation of the implant component relative to the body part;
   (d) generating and displaying on a monitor associated with the computer a visual image of the implant component properly positioned and oriented relative to the knee joint; and (e) navigating the implant component relative to the body part and attaching the implant component to the body part according to the image.

19. The process of claim 18, further comprising performing soft tissue balancing tests on the joint with implant component installed while the computer continues to track the fiducials.

20. A process for performing total knee arthroplasty surgical operations on portion of a knee joint comprising:

(a) obtaining data corresponding to structure of a body part forming a portion of said joint with a locator, wherein the body part and the locator are each attached to a fiducial capable of being tracked by at least one position sensor;

(b) registering a total knee arthroplasty implant component attached to a tool to which is attached a fiducial capable of being tracked by at least one position sensor;

(c) using a computer which receives signals from the at least one sensor, tracking position and orientation of the implant component relative to the body part;

(d) generating and displaying on a monitor associated with the computer a visual image of the implant component properly positioned and oriented relative to the body part;

(e) navigating the implant component relative to the body part and attaching the implant component to the body part according to the image;

(f) discontinuing tracking of the implant component using the fiducial attached to the tool;

(g) initiating tracking of the implant component using the fiducial attached to the body part on which the implant component is attached;

(h) performing soft tissue balancing tests while the computer continues to track the fiducials; and (i) using data generated by the computer to assess alignment and stability of the joint with the implant installed.

* * * * *